US012133722B2

(12) United States Patent
Iwade et al.

(10) Patent No.: US 12,133,722 B2
(45) Date of Patent: Nov. 5, 2024

(54) BIOLOGICAL INFORMATION MEASUREMENT APPARATUS, METHOD, AND PROGRAM

(71) Applicants: OMRON Corporation, Kyoto (JP); OMRON HEALTHCARE CO., LTD., Muko (JP)

(72) Inventors: Ayaka Iwade, Nara (JP); Keigo Kamada, Tokyo (JP); Satoshi Yase, Nara (JP); Hisashi Ozawa, Kyoto (JP); Masayuki Sugano, Uji (JP); Keisuke Saito, Suita (JP); Yasuhiro Kawabata, Kyoto (JP)

(73) Assignees: OMRON Corporation, Kyoto (JP); OMRON HEALTHCARE CO., LTD, Muko (JP)

( * ) Notice: Subject to any disclaimer, the term of this patent is extended or adjusted under 35 U.S.C. 154(b) by 1036 days.

(21) Appl. No.: 17/041,017

(22) PCT Filed: Apr. 2, 2019

(86) PCT No.: PCT/JP2019/014627
§ 371 (c)(1),
(2) Date: Sep. 24, 2020

(87) PCT Pub. No.: WO2019/198567
PCT Pub. Date: Oct. 17, 2019

(65) Prior Publication Data
US 2021/0022639 A1    Jan. 28, 2021

(30) Foreign Application Priority Data

Apr. 12, 2018  (JP) ................ 2018-076707

(51) Int. Cl.
*A61B 5/05* (2021.01)
*A61B 5/00* (2006.01)
*A61B 5/021* (2006.01)

(52) U.S. Cl.
CPC ............ *A61B 5/05* (2013.01); *A61B 5/7405* (2013.01); *A61B 5/742* (2013.01); *A61B 5/7455* (2013.01); *A61B 5/021* (2013.01); *A61B 5/681* (2013.01)

(58) Field of Classification Search
CPC ...................................................... A61B 5/05
See application file for complete search history.

(56) References Cited

U.S. PATENT DOCUMENTS

| | | |
|---|---|---|
| 2005/0004473 A1 | 1/2005 | Fujita et al. |
| 2010/0305460 A1 | 12/2010 | Pinter et al. |

(Continued)

FOREIGN PATENT DOCUMENTS

| | | |
|---|---|---|
| CN | 101150977 A | 3/2008 |
| CN | 103079463 A | 5/2013 |

(Continued)

OTHER PUBLICATIONS

Chinese Office Action issued on Apr. 28, 2023 in a counterpart Chinese patent application.

(Continued)

*Primary Examiner* — Jason M Ip
(74) *Attorney, Agent, or Firm* — METROLEX IP LAW GROUP, PLLC; Robert L. Scott, Esq.

(57) ABSTRACT

In an apparatus for measuring biological information using a radio wave, a technique for acquiring an index related to a setting position of the apparatus with respect to a measurement site is provided. A biological information measurement apparatus (1) according to an aspect of the present disclosure includes a transmitter (3) configured to transmit a (Continued)

radio wave toward a measurement site of a living body; a receiver (4) configured to receive a reflected wave of the radio wave reflected by the measurement site and output a waveform signal of the reflected wave; a feature extraction unit (121) configured to extract information indicative of a feature of a waveform from the waveform signal; a determination unit (122) configured to determine whether a setting position of the biological information measurement apparatus with respect to the measurement site satisfies a condition corresponding to a preset reference position based on the extracted information indicative of the feature of the waveform; and an output unit (5) configured to output information indicative of a determination result determined by the determination unit.

19 Claims, 28 Drawing Sheets

(56) References Cited

U.S. PATENT DOCUMENTS

| | | | |
|---|---|---|---|
| 2013/0165800 | A1 | 6/2013 | Shimizu et al. |
| 2014/0058253 | A1* | 2/2014 | Prough ............. A61M 16/0488 600/424 |
| 2014/0152491 | A1 | 6/2014 | Lee et al. |
| 2014/0343393 | A1 | 11/2014 | Lee et al. |
| 2016/0198977 | A1* | 7/2016 | Eom ................... A61B 5/02416 600/300 |
| 2017/0119318 | A1* | 5/2017 | Shay .................... A61B 5/7225 |
| 2020/0305759 | A1* | 10/2020 | Barash ................ A61B 5/0816 |

FOREIGN PATENT DOCUMENTS

| | | |
|---|---|---|
| JP | 2010-69158 A | 4/2010 |
| JP | 2011-507583 A | 3/2011 |
| JP | 2012-157435 A | 8/2012 |
| JP | 2013-000177 A | 1/2013 |
| JP | 2013-042840 A | 3/2013 |
| JP | 2015-077395 A | 4/2015 |
| JP | 5879407 B2 | 3/2016 |
| WO | 2012/033232 A1 | 3/2012 |

OTHER PUBLICATIONS

The Notification of Transmittal of Copies of Translation of the International Preliminary Report on Patentability ("IPRP") of the international application PCT/JP2019/014627 mailed on Oct. 22, 2020.
The English translation of the Written Opinion ("WO") of the international application PCT/JP2019/014627 mailed on Jul. 2, 2019.
Japanese Office Action issued on Mar. 8, 2022 in a counterpart Japanese patent application.
International Search Report ("ISR") of the international application PCT/JP2019/014627 mailed on July 2. 2019.
Written Opinion ("WO") of the international application PCT/JP2019/014627 mailed on Jul. 2, 2019.

* cited by examiner

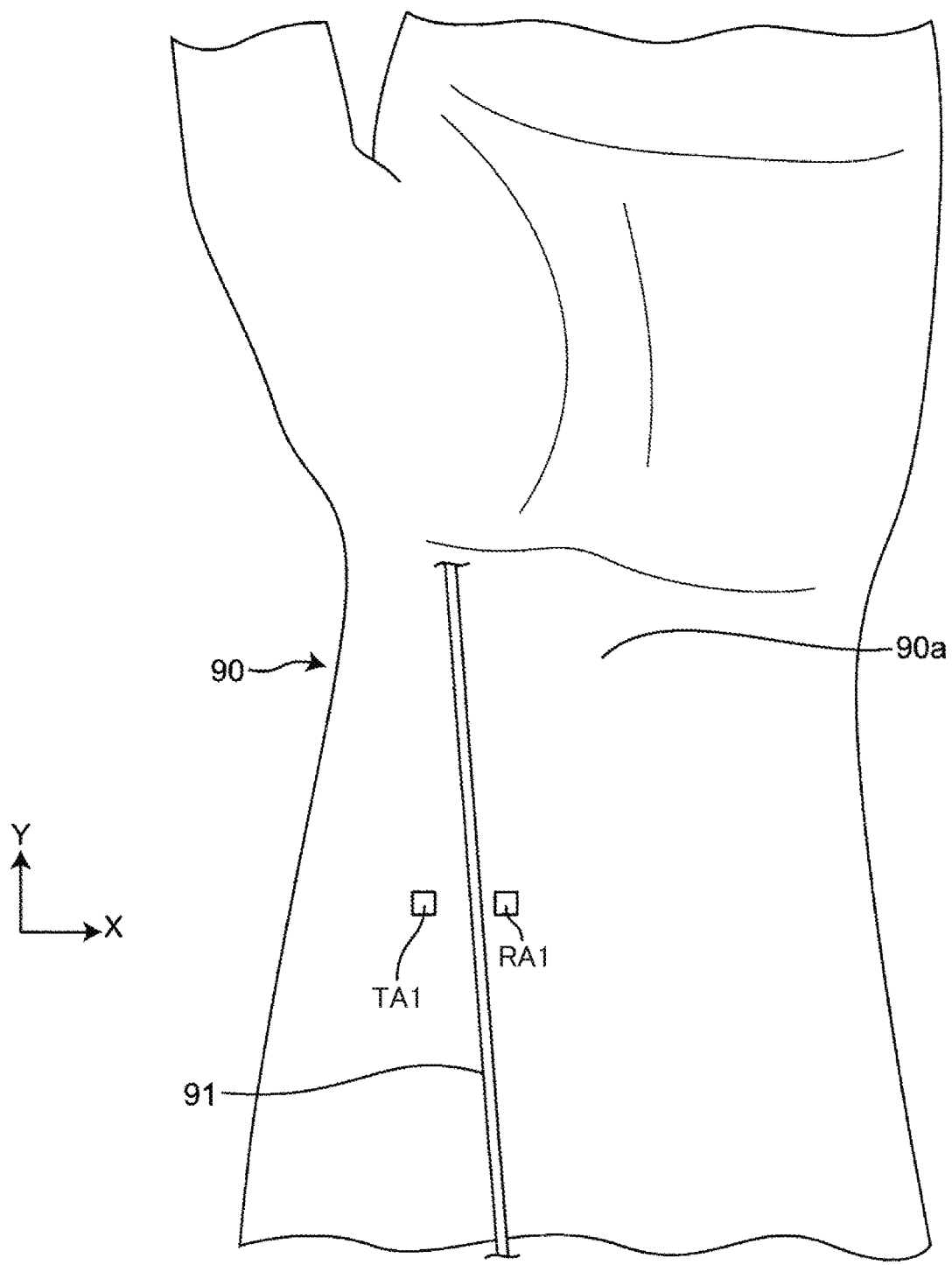
F I G. 4

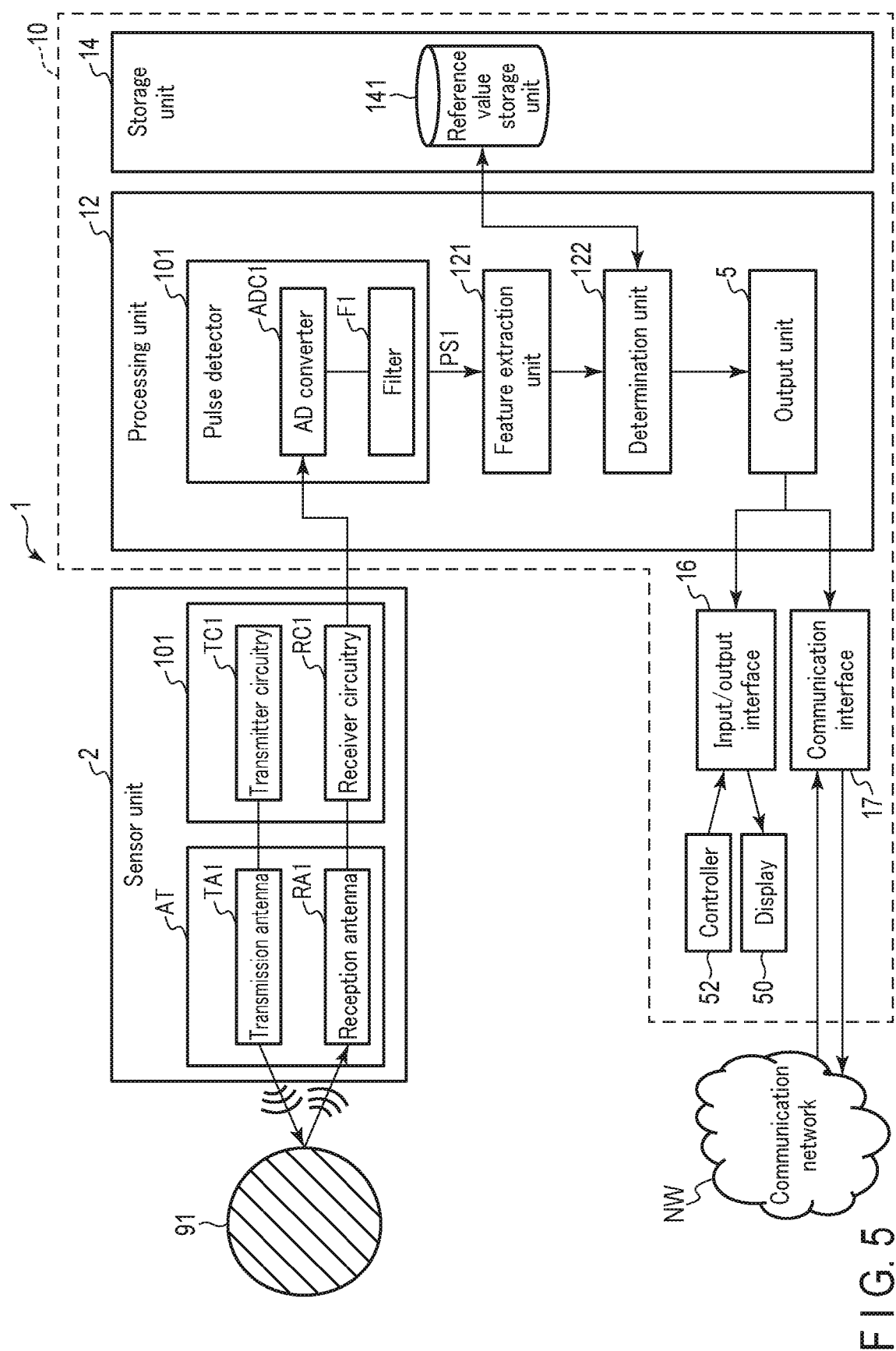
F I G. 5

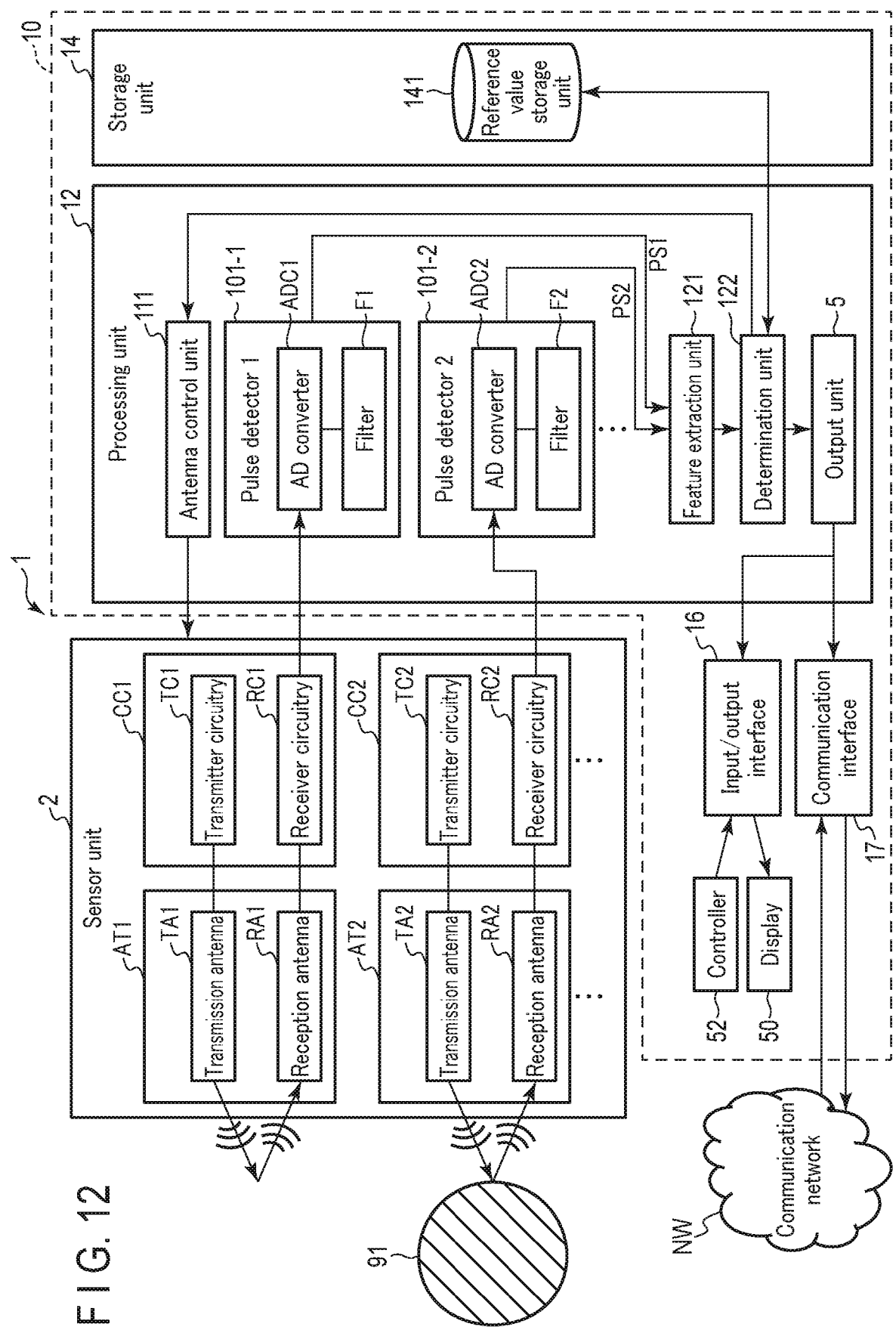
F I G. 12

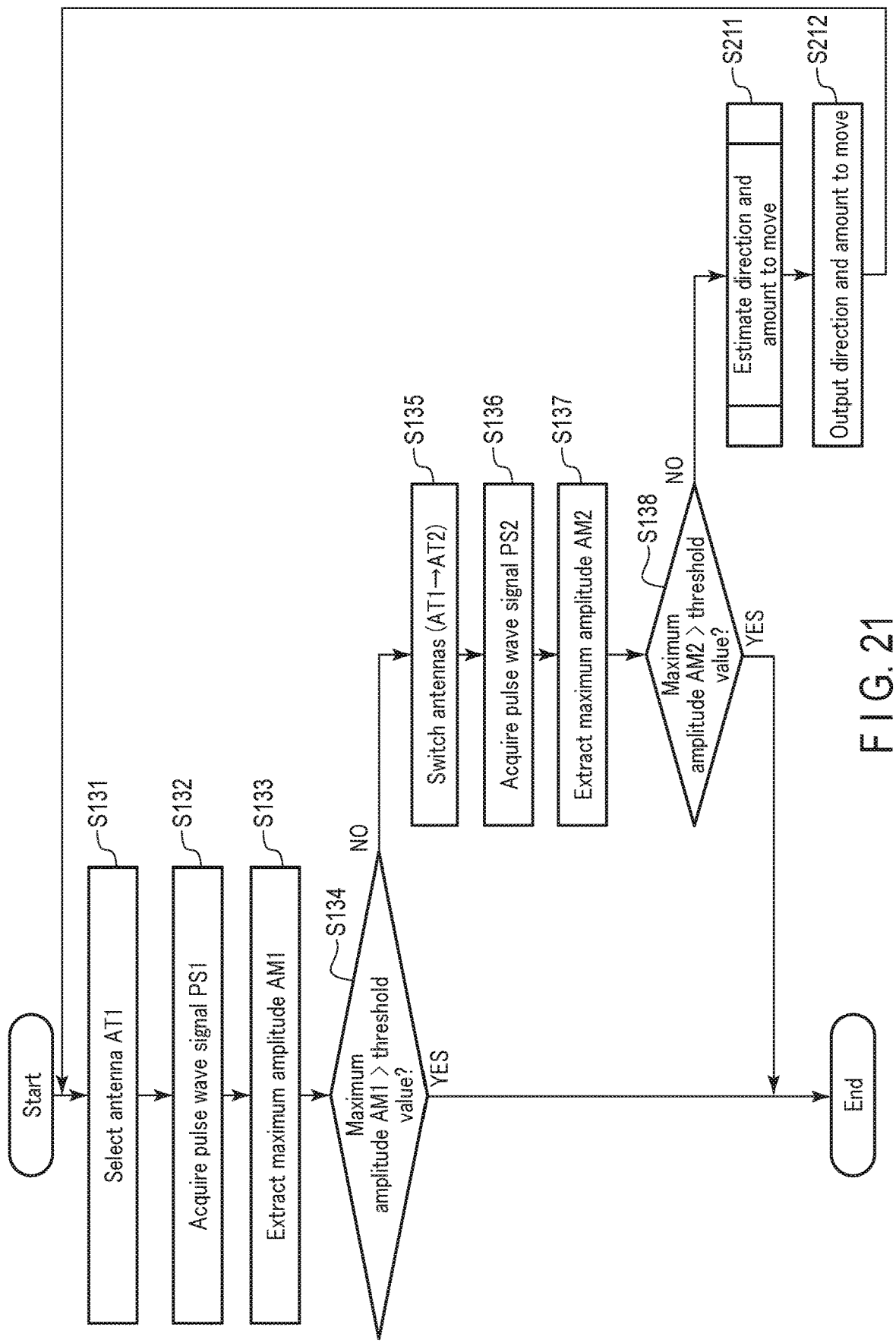
F I G. 21

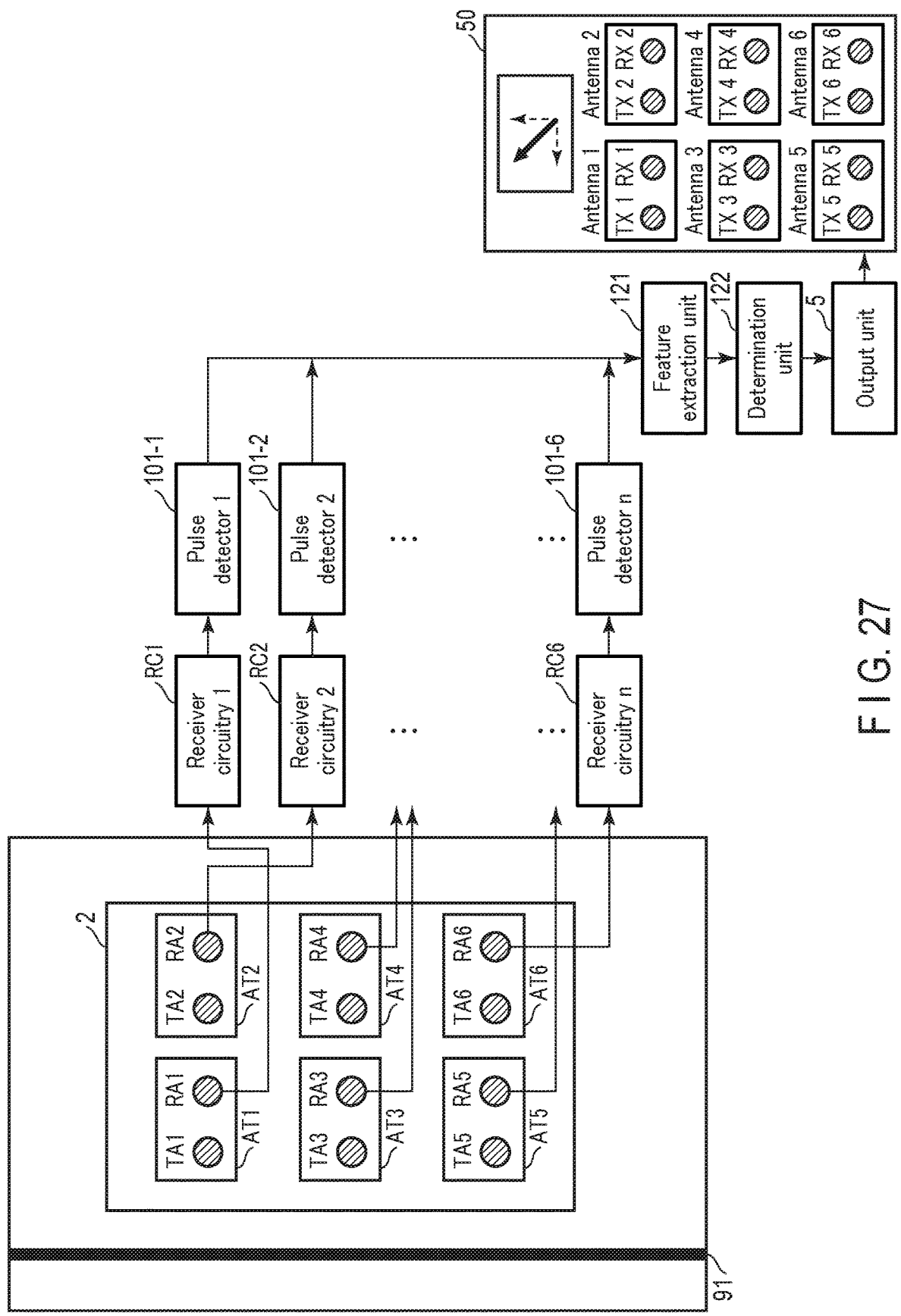
F I G. 27

BIOLOGICAL INFORMATION MEASUREMENT APPARATUS, METHOD, AND PROGRAM

CROSS REFERENCE

The present application is a U. S. national phase application under 35 USC § 371 of International Application PCT/JP2019/014627 (not published in English), filed Apr. 2, 2019.

FIELD

The present invention relates to a biological information measurement apparatus, method, and program for measuring biological information using radio waves.

BACKGROUND

Conventionally, an apparatus for measuring biological information using radio waves is known, which includes a transmission antenna and a reception antenna disposed to face a measurement site (target object), transmits radio waves (measurement signals) from the transmission antenna toward the measurement site, receives reflected waves (reflected signals) of the transmitted radio waves reflected by the measurement site, and measures biological information (for example, see Patent Literature 1).

CITATION LIST

Patent Literature

Patent Literature 1: Japanese Patent No. 5879407

SUMMARY

Technical Problem

In the case of measuring, for example, a pulse wave (or a signal related to a pulse wave) as biological information, a measurement site is generally a wrist or an upper arm. For example, in a case where measurement is performed with a wearable device worn on a wrist, it is assumed that a transmission antenna and a reception antenna (collectively referred to as a "transmission/reception antenna pair" or simply as an "antenna" as appropriate) are disposed on a wrist-worn strap of the device, and a pulse wave signal is measured by the transmission/reception antenna pair. In this case, when the wearable device is worn on the body, the transmission/reception antenna pair needs to appropriately face the measurement site. However, this type of conventional apparatus has no index for easily determining whether or not the wearing position of the apparatus with respect to the measurement site is appropriate.

In one aspect of the invention, to solve the above problem, the present invention is to provide a biological information measurement apparatus, method, and program capable of acquiring an index related to a setting position of the biological information measurement apparatus with respect to a measurement site and having a simple and inexpensive configuration, without separately providing a device necessary for alignment.

Solution to Problem

To solve the above problem, according to a first aspect of the present invention, a biological information measurement apparatus for measuring biological information of a user, comprises: a transmitter configured to transmit a radio wave to a measurement site of the user; a receiver configured to receive a reflected wave of the radio wave reflected by the measurement site and output a waveform signal of the reflected wave; a feature extraction unit configured to extract information indicative of a feature of a waveform from the waveform signal; a first determination unit configured to determine whether a setting position of the biological information measurement apparatus with respect to the measurement site satisfies a condition corresponding to a preset reference position based on the extracted information indicative of the feature of the waveform; and an output unit configured to output information indicative of a determination result determined by the first determination unit.

According to the first aspect of the present invention, the information indicative of the feature of the waveform is extracted from the waveform signal obtained by transmission and reception of radio waves to and from the measurement site. Based on the information, it is determined whether or not the setting position of the biological information measurement apparatus with respect to the measurement site satisfies a predetermined condition corresponding to the reference position, and a determination result is output. Therefore, it is possible to obtain an index relating to the setting position of the apparatus with respect to the measurement site without separately providing a device necessary for alignment. Therefore, the apparatus can be provided with a simple configuration at low cost. In addition, the user can confirm the index related to the setting position based on the information indicative of the output determination result, and can appropriately adjust the setting position of the apparatus with respect to the measurement site based on the index, for example.

According to a second aspect of the present invention, in the first aspect, the feature extraction unit extracts information on an amplitude of the waveform signal as the feature of the waveform of the waveform signal, and the first determination unit determines whether the amplitude of the waveform signal is within a preset first amplitude range corresponding to the reference position based on the extracted information on the amplitude of the waveform signal.

According to the second aspect of the present invention, the information on the amplitude of the waveform signal is extracted as the feature of the waveform signal, and it is determined whether or not the amplitude of the waveform signal is within a predetermined amplitude range corresponding to the reference position. Therefore, it is possible to obtain an index relating to the setting position of the apparatus with respect to the measurement site based on simple determination focusing only on the amplitude of the waveform signal.

According to a third aspect of the present invention, in the first aspect, the feature extraction unit extracts information on a shape of a waveform for each repetition section of the waveform signal as the feature of the waveform of the waveform signal, and the first determination unit calculates a correlation value between the extracted shape of the waveform and a shape of a preset reference waveform corresponding to the reference position based on the extracted information on the shape of the waveform, and determines whether the correlation value is within a preset first correlation value range.

According to the third aspect of the present invention, information relating to the shape of the waveform for each repetition section of the waveform is extracted as a feature of the waveform signal, and based on this information, it is determined whether or not the correlation value between the shape of the extracted waveform and the shape of a predetermined reference waveform corresponding to the reference position is within a predetermined range corresponding to the reference position. Therefore, it is possible to obtain an index relating to the setting position of the apparatus with respect to the measurement site based on simple determination focusing only on the shape of the waveform for each repetition section of the waveform signal.

According to a fourth aspect of the present invention, in any one of the first to third aspects, the biological information measurement apparatus further comprises a first control unit configured to control a series of operations by the transmitter, the receiver, the feature extraction unit, the first determination unit, and the output unit, wherein the first control unit causes the series of operations to be performed at a first time, and if it is determined that the setting position of the biological information measurement apparatus fails to satisfy the condition through the series of operations at the time, the first control unit causes the series of operations to be performed at a second time.

According to the fourth aspect of the present invention, in a series of operations including transmission and reception of the radio wave, extraction of the feature of the waveform, determination regarding a setting position, and output of a determination result, if it is determined that the setting position fails to satisfy the predetermined condition, the series of operations is repeatedly executed. Therefore, if it is determined that the setting position of the apparatus with respect to the measurement site is not appropriate, the processing is not immediately terminated and the series of operations repeated, so that the reliability of the determination result can be improved.

According to a fifth aspect of the present invention, in the fourth aspect, if it is determined that the setting position of the biological information measurement apparatus fails to satisfy the condition through the series of operations at the first time, the first control unfit causes the series of operations to be performed at a second time in response to any one of an elapse of a predetermined time after the determination, an input of a measurement instruction by the user, and a change in the setting position of the biological information measurement apparatus by a predetermined amount or more.

According to the fifth aspect of the present invention, even if it is determined in the series of operations that the setting position of the apparatus with respect to the measurement site is not appropriate, the series of operations is repeated when any one of the elapse of time, the input by the user, and the change in the position of the apparatus is detected. Therefore, the processing is not immediately terminated if it is determined that the setting position of the apparatus is not appropriate, but the determination of whether or not the setting position of the apparatus satisfies the condition is performed again automatically after waiting for a predetermined time, or in response to the input of the instruction by the user, or when the change in the position of the apparatus is detected.

According to a sixth aspect of the present invention, in any one of the first to third aspects, the biological information measurement apparatus further comprises a second control unit configured to control a series of operations by the transmitter, the receiver, the feature extraction unit, and the first determination unit, wherein the transmitter and the receiver include a first antenna and a second antenna dispersedly arranged on a surface opposable to the measurement site, and transmit the radio wave and receive the reflected wave through the first and second antennas; the second control unit selects the first antenna and causes the series of operations to be performed at a first time, and if it is determined that the setting position of the biological information measurement apparatus fails to satisfy the condition through the series of operations at the first time, the second control unit selects the second antenna and causes the series of operations to be performed at a second time.

According to the sixth aspect of the present invention, in a state in which the first antenna is selected, a series of operations including transmission and reception of a radio wave, extraction of a feature of a waveform, and determination relating to a setting position are executed, and if it is determined in the series of operations that the setting position fails to satisfy a condition, the second antenna is selected and the series of operations is repeatedly executed. Therefore, the processing is not immediately terminated even if it is determined that the setting position of the biological information measurement apparatus with respect to the measurement site is not appropriate, but a series of operations is repeated by switching the antennas, so that it is possible to perform the determination twice using different antennas dispersedly arranged without altering the wearing position of the apparatus, and to reduce complexity related to alignment of the apparatus.

According to a seventh aspect of the present invention, in any one of the first to third aspects, the biological information measurement apparatus further comprises a second control unit configured to control a series of operations by the transmitter, the receiver, the feature extraction unit, and the first determination unit, wherein the transmitter and the receiver include a first transmission antenna and first and second reception antennas dispersedly arranged on a surface opposable to the measurement site, and transmit radio waves and receive reflected waves through the first transmission antenna and the first and second reception antennas; the second control unit selects the first transmission antenna and the first reception antenna, and causes the series of operations to be performed at a first time, and if it is determined that the setting position of the biological information measurement apparatus fails to satisfy the condition through the series of operations at the first time, the second control unit selects the first reception antenna and the second reception antenna and causes the series of operations to be performed at a second time.

According to the seventh aspect of the present invention, in a state in which the first transmission antenna and the first reception antenna are selected, a series of operations including transmission and reception of the radio wave, extraction of the feature of the waveform, and determination regarding a setting position are executed, and if it is determined in the series of operations that the setting position fails to satisfy a condition, the second reception antenna is selected and the series of operations is repeatedly executed. Therefore, even if it is determined that the setting position of the biological information measurement apparatus with respect to the measurement site is not appropriate, the processing is not immediately terminated, but a series of operations is repeated by switching at least the reception antenna. Thus, it is possible to perform determination twice using different antennas dispersedly arranged without altering the wearing position of the apparatus, and to reduce complexity related to alignment of the apparatus.

According to an eighth aspect of the present invention, a biological information measurement apparatus fog measuring biological information of a user comprises: a transmitter configured to transmit a radio wave to a measurement site of the user; a receiver configured to receive a reflected wave of the radio wave reflected by the measurement site and output a waveform signal of the reflected wave; a feature extraction unit configured to extract information indicative of a feature of a waveform from the waveform signal; a second determination unit configured to compare information indicative of a feature of a first waveform extracted by the feature extraction unit in a transmission operation of the radio wave and a reception operation of the reflected wave at a first time with information indicative of a feature cif a second waveform extracted by the feature extraction unit in a transmission operation of the radio wave and a reception operation of the reflected wave at a second time, and determine a correction direction of a setting position of the biological information measurement apparatus with respect to the measurement site based on the comparison result; and an output unit configured to output information indicative of the determined correction direction.

According to the eighth aspect of the present invention, the transmission and reception of the radio wave to and from the measurement site and the extraction of information indicative of the feature of the waveform from, the waveform signal obtained thereby are performed twice, and the information indicative of the feature of the first waveform extracted at the first time is compared with the information indicative of the feature of the second waveform extracted at the second time to determine the direction in which the setting position of the biological information measurement apparatus with respect to the measurement site should be corrected, and the result is output. Therefore, it is possible to obtain an index indicating the direction in which the biological information measurement apparatus should be moved with respect to the measurement site with a simple and inexpensive configuration, and without separately providing a complicated evaluation device. Since the user can adjust the position of the apparatus with respect to the measurement site after confirming the direction in which the apparatus should be moved based on the output determination result, the apparatus can be efficiently aligned, and the convenience of the user can be improved.

According to a ninth aspect of the present invention, in the eighth aspect, the second determination unit compares information indicative of a feature of a first waveform extracted by the feature extraction unit in a transmission operation of the radio wave and a reception operation of the reflected wave at a first time and a second reception operation of the reflected wave with information indicative of a feature of a second waveform extracted by the feature extraction unit in a transmission operation of the radio wave and a reception operation of the reflected wave at a second time, and further calculates a correction amount of the setting position of the biological information measurement apparatus with respect to the measurement site based on the comparison result; and the output unit outputs information indicative of the determined correction direction and the calculated correction amount.

According to the ninth aspect of the present invention, the information indicative of the feature of the first waveform extracted at the first time is compared with the information indicative of the feature of the second waveform extracted at the second time, so that in addition to the direction in which the setting position of the biological information measurement apparatus with respect to the measurement site is to be corrected, the amount to be corrected is calculated and the result is output. Therefore, without separately providing a complicated evaluation device, it is possible to obtain, with a simple and inexpensive configuration, an index indicating the direction and extent to which the biological information measurement apparatus should be moved with respect to the measurement site based on the results of the measurements of two times. Since the user can adjust the position of the apparatus with respect to the measurement site after confirming the direction and extent to which the apparatus should be moved based on the output determination result, it is possible to more efficiently align the apparatus, and user convenience can be further improved.

According to a tenth aspect of the present invention, the biological information measurement apparatus for measuring biological information of a user comprises: a transmission/reception unit including first and second antennas dispersedly arranged on a surface opposable to a measurement site of the user, and configured to transmit radio waves toward the measurement site and receive reflected waves of the radio waves reflected by the measurement site through the first and second antennas, and output waveform signals of the reflected waves; a feature extraction unit configured to extract information indicative of a feature of a waveform from the waveform signal; a second determination unit configured to compare information indicative of a feature of a first waveform extracted by the feature extraction unit in a transmission operation of the radio wave and a reception operation of the reflected wave through the first antenna and a second reception operation of the reflected wave with information indicative of a feature of a second waveform extracted by the feature extraction unit in a transmission operation of the radio wave and a reception operation of the reflected wave through the second antenna, and to determine a correction direction of a setting position of the biological information measurement apparatus with respect to the measurement site based on the comparison result; and an output unit configured to output information indicative of the determined correction direction.

According to the tenth aspect of the present invention, the transmission and reception of radio waves to and from the measurement site and the extraction of information indicative of the feature of the waveform from the waveform signal obtained by the transmission and reception are performed using the first and second antennas, respectively, and the information indicative of the feature of the first waveform extracted when the first antenna is used is compared with the information indicative of the features of the second waveform extracted: when the second antenna is used, thereby determining the direction in which the setting position of the biological information measurement apparatus with respect to the measurement site is to be corrected, and the result is output. Therefore, without separately providing a complicated evaluation device, it is possible to obtain, with a simple and inexpensive configuration, an index indicating the direction in which the biological information measurement apparatus should be moved with respect to the measurement site, based on the results of the measurements using a plurality of antennas without altering the setting position of the apparatus. Since the user can adjust the setting position with respect to the measurement site after confirming the direction in which the apparatus should be moved based on the output determination result, the apparatus can be efficiently aligned, and user convenience can be improved.

According to an eleventh aspect of the present invention, the biological information measurement apparatus for measuring biological information of a user comprises: a transmission/reception unit including a first transmission antenna and first and second reception antennas dispersedly arranged on a surface opposable to a measurement site of the user, and configured to transmit radio waves toward the measurement site and receive reflected waves of the radio waves reflected by the measurement site through the first transmission antennas and the first and second reception antennas, and output waveform signals of the reflected waves; a feature extraction unit configured to extract information indicative of a feature of a waveform from the waveform signal; a second determination unit configured to compare information indicative of a feature of a first waveform extracted by the feature extraction unit in a transmission operation of the radio wave through the first transmission antenna and a reception operation of the reflected wave through the first reception antenna with information indicative of a feature of a second waveform extracted by the feature extraction unit in a transmission operation of the radio wave through the first transmission antenna and a reception operation of the reflected wave through the second reception antenna, and determine a correction direction of a setting position of the biological information measurement apparatus with respect to the measurement site based on the comparison result; and an output unit configured to output information indicative of the determined correction direction.

According to the eleventh aspect of the present invention, the information indicative of the feature of the first waveform of the waveform signal obtained by transmitting and receiving the radio wave to and from the measurement site using the first transmission antenna and the first reception antenna is compared with the information indicative of the feature of the second waveform of the waveform signal obtained by using the first transmission antenna and the second reception antenna, thereby determining the direction in which the setting position of the biological information measurement apparatus with respect to the measurement site is to be corrected, and the result is output. Therefore, without separately providing a complicated evaluation device, it is possible to obtain, with a simple and inexpensive configuration, an index indicating the direction in which the biological information measurement apparatus should be moved with respect the measurement site based on the results of the measurements using different reception antennas without altering the setting position of the apparatus. Also, since the user can adjust the setting position of the apparatus with respect to the measurement site after confirming the direction in which the apparatus should be moved based on the output determination result, the apparatus can be efficiently aligned and user convenience can be improved.

According to a twelfth aspect of the present invention, in the tenth or eleventh aspect, the second determination unit compares the information indicative of the feature of the first waveform with the information indicative of the feature of the second waveform, and further calculates a correction amount of the setting position of the biological information measurement apparatus with respect to the measurement site based on the comparison result; and the output unit outputs information indicative of the determined correction direction and the calculated correction amount.

According to the twelfth aspect of the present invention, the information indicative of the feature of the first waveform extracted when using the first antenna (pair) is compared with the information indicative of the feature of the second waveform extracted when using the second antenna (pair), so that in addition to the direction in which the setting position of the biological information measurement apparatus with respect to the measurement site is to be corrected, the amount to be corrected is calculated and the result is output. Therefore, without separately providing a complicated evaluation device, it is possible to obtain an index indicating the direction and extent to which the biological information measurement apparatus should be moved with respect to the measurement based on the results of the measurements using a plurality of antennas. Further, since the correction amount can be calculated from results of measurements of two times using two antennas whose relative positions can be known in advance without altering the position of the apparatus, a more reliable determination result can be obtained. Since the user can adjust the position of the apparatus with respect to the measurement site after confirming the direction and extent to which the apparatus should be moved based on the output determination result, it is possible to more efficiently align the apparatus and improve user convenience.

According to a thirteenth aspect of the present invention, in the ninth or twelfth aspect, the second determination unit calculates the correction amount by linear approximation based on the information indicative of the feature of the first waveform and the information indicative of the feature of the second waveform.

According to the thirteenth aspect of the present invention, the distance to the reference position is estimated by obtaining an approximation function on the assumption that the information indicative of the features of the two waveforms obtained by the two measurements has a linear relationship. Therefore, it is possible to estimate the amount to be corrected through simple calculation from the obtained measurement result without separately providing a complicated evaluation device.

According to a fourteenth aspect of the present invention, in the ninth or twelfth aspect, the second determination unit calculates the correction amount by nonlinear approximation based on the information indicative of the feature of the first waveform and the information indicative of the feature of the second waveform.

According to the fourteenth aspect of the present invention, the distance to the reference position is estimated by obtaining an approximation function on the assumption that the information indicative of the features of the two waveforms obtained by the two measurements has a nonlinear relationship. Therefore, it is possible to easily estimate the amount by which the setting position is to be corrected from the obtained measurement result by using an arbitrary approximate curve according to the designer's preference, and without separately providing a complicated evaluation device.

According to a fifteenth aspect of the present invention, in any one of the first to fourteenth aspects, the output unit notifies the user of the information indicative of the determination result through the first determination unit or the correction direction and correction amount determined by the second determination unit by at least one of text, an image, sound, vibration, and lighting or blinking of light.

According to the fifteenth aspect of the present invention, the user is notified of the determination result indicating whether or not the setting position of the biological information measurement device is appropriate, or the direction in which the setting position is to be corrected, or the amount by which the setting position is to be corrected, by at least one of text, an image, sound, vibration, and lighting or blinking of light. Therefore, the user can adjust the setting position while easily determining whether the setting position is appropriate in the process of aligning the apparatus. In addition, it is possible to clearly instruct even a user who is unfamiliar with the use of the apparatus about an operation to be performed when the setting position of the apparatus is inappropriate, while coping with a variety of operation environments or users by various notification methods. As a result, user convenience is improved.

Advantageous Effects of Invention

According to each aspect of the present invention, it is possible to provide a biological information measurement apparatus, method, and program capable of acquiring an index related to a setting position of the biological information measurement apparatus with respect to a measurement site with a simple and inexpensive configuration, and without separately providing a device necessary for alignment.

BRIEF DESCRIPTION OF THE DRAWINGS

FIG. 4 is a diagram illustrating a planar layout of an antenna in a state where the blood pressure monitor illustrated in FIG. 3 is worn on a left wrist.

FIG. 5 is a block diagram illustrating an example of a functional configuration of the biological information measurement apparatus according to the embodiment of the present disclosure.

FIG. 12 is a block diagram illustrating an example of a functional configuration of the biological information measurement apparatus according to the embodiment of the present disclosure.

FIG. 21 is a flowchart illustrating another example of the processing procedure of the biological information measurement apparatus illustrated in FIG. 18.

FIG. 25B is a diagram illustrating another example of the regression curve in the estimation procedure illustrated in FIG. 25.

FIG. 27 is a schematic diagram illustrating a part of a functional configuration of a biological information measurement apparatus according to another embodiment of the present disclosure and a relative positional relationship between an artery and an antenna.

DETAILED DESCRIPTION

Hereinafter, an embodiment according to one aspect of the present invention will be described with reference to the drawings.

Application Example (Configuration)

First, an example of a scene to which the present invention is applied will be described.

Figure 1:
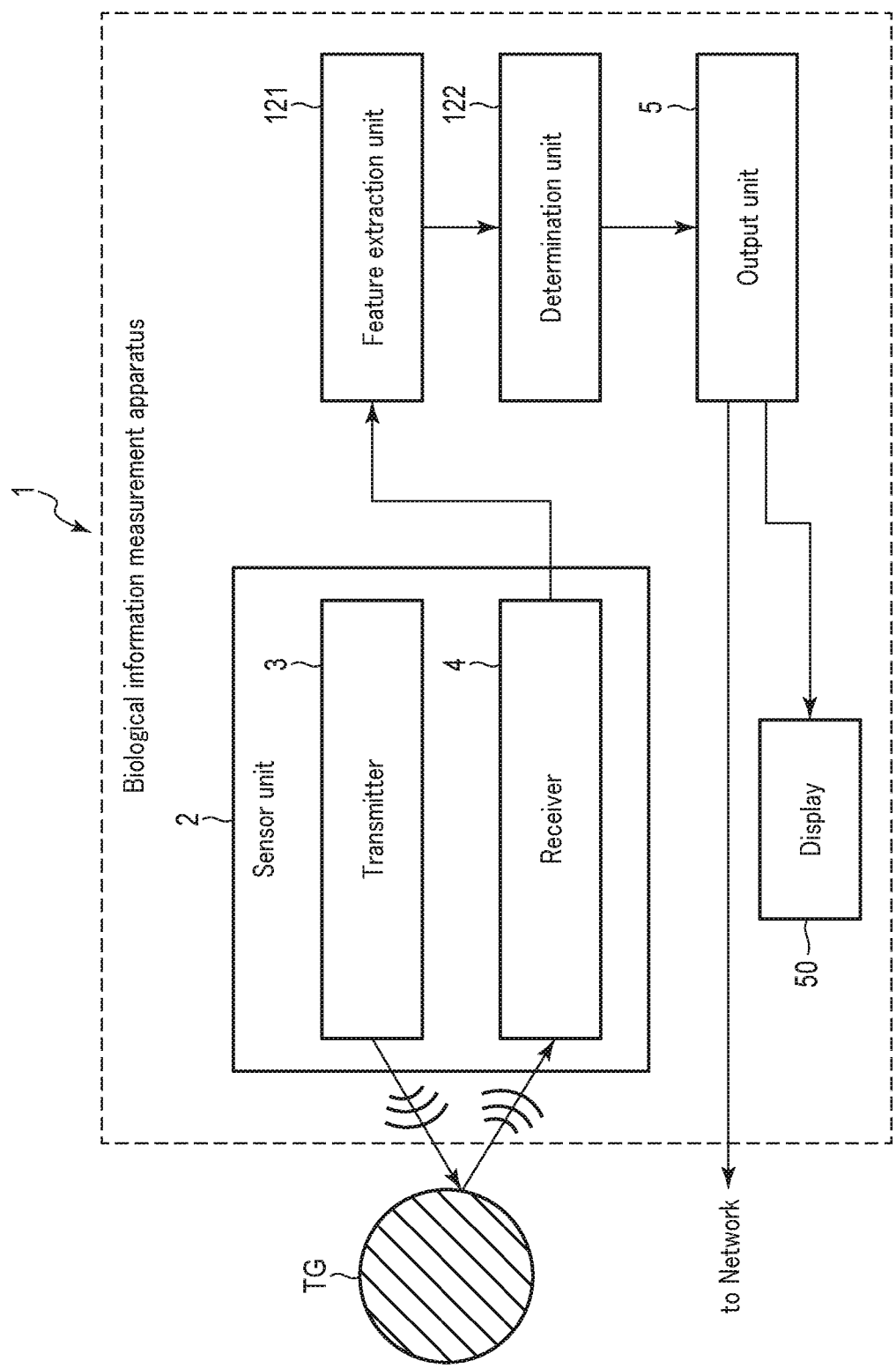
FIG. 1 is a block diagram for explaining an application example of a biological information measurement apparatus according to an embodiment of the present disclosure.

FIG. 1 schematically shows an application example of a biological information measurement apparatus according to an embodiment of the present invention.

In the example of FIG. 1, the biological information measurement apparatus 1 includes a sensor unit 2, a feature extraction unit 121, a determination unit 122, an output unit 5, and a display 50. The biological information measurement apparatus 1 is disposed such that the sensor unit 2 faces a measurement site of a living body.

The measurement site TG is, for example, a portion including a radial artery of a human wrist. The biological information measurement apparatus 1 is, for example, a wristwatch-type wearable device, and is disposed such that the sensor unit 2 faces a palm-side surface of a wrist when worn. For example, pulse waves (or signals related to pulse waves) are measured as biological information.

The sensor unit 2 is a pulse sensor that measures pulse waves in, for example, the radial artery of the user, and includes a transmitter 3 and a receiver 4.

The transmitter 3 includes a transmission antenna element and transmitter circuitry, and transmits a radio wave as a measurement signal toward the measurement site.

The receiver 4 includes a reception antenna element and receiver circuitry, receives a reflected wave of the radio wave reflected by the measurement site TG, and outputs a waveform signal of the reflected wave.

The feature extraction unit 121 receives the waveform signal output from the receiver 4, generates a pulse wave signal based on the waveform signal, and then extracts information indicative of the feature of the waveform from the pulse wave signal.

The determination unit 122 determines whether or not the setting position of the biological information measurement apparatus 1 with respect to the measurement site TG satisfies a condition corresponding to a preset reference position, based on the information indicative of the feature of the waveform of the pulse wave signal extracted by the feature extraction unit 121. In this example, the setting position (also referred to as the "wearing position") indicates the position of the sensor unit 2 with respect to the radial artery as the measurement site TG, in particular, the relative position of the transmission/reception antenna pair with respect to the radial artery in this example, the reference position refers to an ideal setting position with respect to the radial artery that is suitable for acquisition of pulse waves by the sensor unit 2. However, the reference position may be appropriately set by a designer. In this example, the condition corresponding to the reference position represents features (an amplitude value, periodicity, spectrum intensity, an ratio, and the like) of a waveform related to an ideal pulse wave acquired at the reference position (ideal position). It is possible to determine whether or not the setting position of the apparatus is appropriate by determining whether or not the measurement value is within an allowable range with respect to these features.

The output unit 5 outputs a determination result through the determination unit 122. For example, the output unit 5 can output information indicating that the setting position of the biological information measurement apparatus 1 satisfies a preset condition, that is, information indicating that the biological information measurement apparatus 1 is located at an appropriate setting position with respect to the measurement site, thereby prompting the user to start measurement. Alternatively, the output unit 5 can output information indicating that the setting position of the biological information measurement apparatus 1 does not satisfy a preset condition, that is, information indicating that the biological information measurement apparatus 1 is not at an appropriate setting position with respect to the measurement site, and can thus notify the user that the position of the device needs to be adjusted before the start of measurement. Alternatively, the output unit 5 may generate a message for warning that the setting position of the apparatus is inappropriate or for prompting correction of the position, and output the message to the display 50.

The display 50 includes, for example, a display and/or a speaker provided in the biological information measurement apparatus 1, and visually or auditorily presents the message output from the output unit 5 to the user. Alternatively, the display 50 may notify the user of the detection result by a vibration. The display 50 may also notify the user by lighting or blinking light using a light source such as a light-emitting diode (LED). The display 50 may be provided separately from the biological information measurement apparatus 1 or may be omitted.

(Operation)

Figure 2:
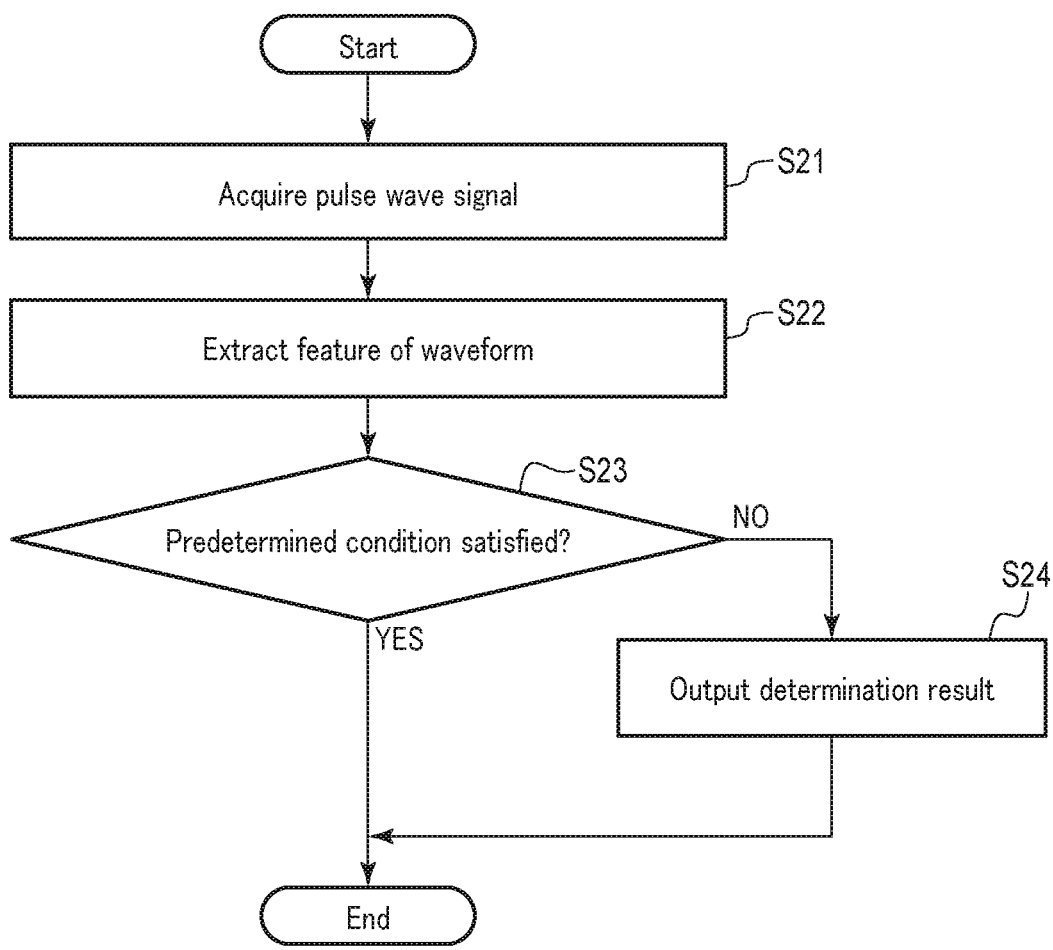
FIG. 2 is a flowchart illustrating an example of a processing procedure of the biological information measurement apparatus illustrated in FIG. 1.

Next, an operation of the biological information measurement apparatus 1 according to the application example will be described. FIG. 2 is a flowchart illustrating an example of a processing procedure of the biological information measurement apparatus 1 illustrated in FIG. 1.

The biological information measurement apparatus 1 transmits a radio wave as a measurement signal to the measurement site TG at a fixed cycle by the transmitter 3. Then, the reflected wave of the radio wave reflected by the measurement site TG is received by the receiver 4 in the fixed cycle. In the receiver 4, a waveform signal of the reflected wave is generated and output to the feature extraction unit 121. The radio waves transmitted by the transmitter 3 may be transmitted continuously or intermittently.

In step S21, the biological information measurement apparatus 1 first converts the waveform signal output from the receiver 4 into a digital signal, and then performs filtering processing for removing unnecessary wave components, such as noise components, to acquire a pulse wave signal. The pulse wave signal is a waveform signal representing the pulsation of the radial artery passing through the measurement site TG.

In step S22, the biological information measurement apparatus 1 extracts a feature of the waveform from the pulse wave signal under the control of the feature extraction unit 121. For example, the feature extraction unit 121 extracts an amplitude value from the waveform of the pulse wave signal. The feature of the waveform is not limited to the amplitude value, and the periodicity of the waveform, the spectral intensity of a predetermined frequency band of the waveform, the shape of the waveform, or the like may be extracted. The feature extraction unit 121 outputs information indicative of the extracted feature of the waveform to the determination unit 122.

Next, in step S23, under the control of the determination unit 122, the biological information measurement apparatus 1 determines whether or not the setting position of the biological information measurement apparatus 1 with respect to the measurement site TG satisfies a condition corresponding to a preset reference position, based on the information indicative of the feature of the waveform output from the feature extraction unit 121. For example, the determination unit 122 determines whether the amplitude value of the waveform signal is within a preset first amplitude range corresponding to the reference position. Thus, when the amplitude value of the waveform signal is within the first amplitude range, the sensor unit 2 is determined to be positioned at a position suitable for measurement, and when the amplitude value of the waveform signal is not within the first range, the sensor unit 2 is determined not to be positioned at a position suitable for measurement.

The method of determining whether or not the condition corresponding to the preset reference position is satisfied is not limited to the above-described, and the determination may be made by comparing the correlation value between the shape of the waveform divided into time intervals and the shape of the reference waveform, the repetition cycle of the waveform signal, or the maximum value of the signal intensity with a threshold value. The determination unit 122 may determine the direction in which the setting position should be corrected by determining which measurement result is closest to the predetermined condition based on the results of a plurality of measurements. Further, the determination unit 122 may estimate the distance from the reference position, that is, the amount by which the setting position is to be corrected, based on the results of a plurality of measurements.

If it is determined in step S23 that the information indicative of the feature of the waveform does not satisfy the predetermined condition, the process proceeds to step S24. In step S24, the biological information measurement apparatus 1 outputs the determination result. For example, the biological information measurement apparatus 1 can generate a message notifying that the apparatus is not located at an appropriate setting position with respect to the measurement site and output the message to the display 50. This allows the user to confirm that the position of the apparatus 1 is not appropriate and to realign the apparatus 1. If it is determined in step S23 that the information indicative of the feature of the waveform satisfies the predetermined condition, the operation ends. However, also in this case, it is possible to generate message notifying that the apparatus is at an appropriate setting position and output the message to the display 50. Accordingly, the user can start the measurement process of the biological information by, for example, pressing a measurement start button shown) provided in the apparatus 1.

(Effect)

As described above, according to the application example, the feature extraction unit 121 extracts the feature of the waveform, for example, the amplitude value from the pulse wave signal obtained by transmission and reception of radio waves to and from the measurement site TG, and the determination unit 122 determines whether or not the condition corresponding to the preset reference position is satisfied based on the extracted feature of the waveform, thereby determining whether or not the setting position of the biological information measurement apparatus 1 with respect to the measurement site TG is within the allowable range with respect to the preset reference position. Therefore, it is possible to obtain an index for determining whether or not the setting position of the apparatus 1 is appropriate with a simple and inexpensive configuration, and without separately providing a position detection device such as an acceleration sensor.

Furthermore, the output unit 5 generates a display message indicating whether or not it is necessary to move the position of the apparatus, for example, based on the result of the determination, and the message is displayed, on the display 50. As a result, the user can confirm from the display message that the attachment of the apparatus is not appropriate, and can appropriately adjust the position of the apparatus. In addition, the user can start the measurement of the biological information by determining that the measurement is ready based on the display message.

First Embodiment

Example 1-1

Configuration Example (1) Structure of Wearable Device

Figure 3:
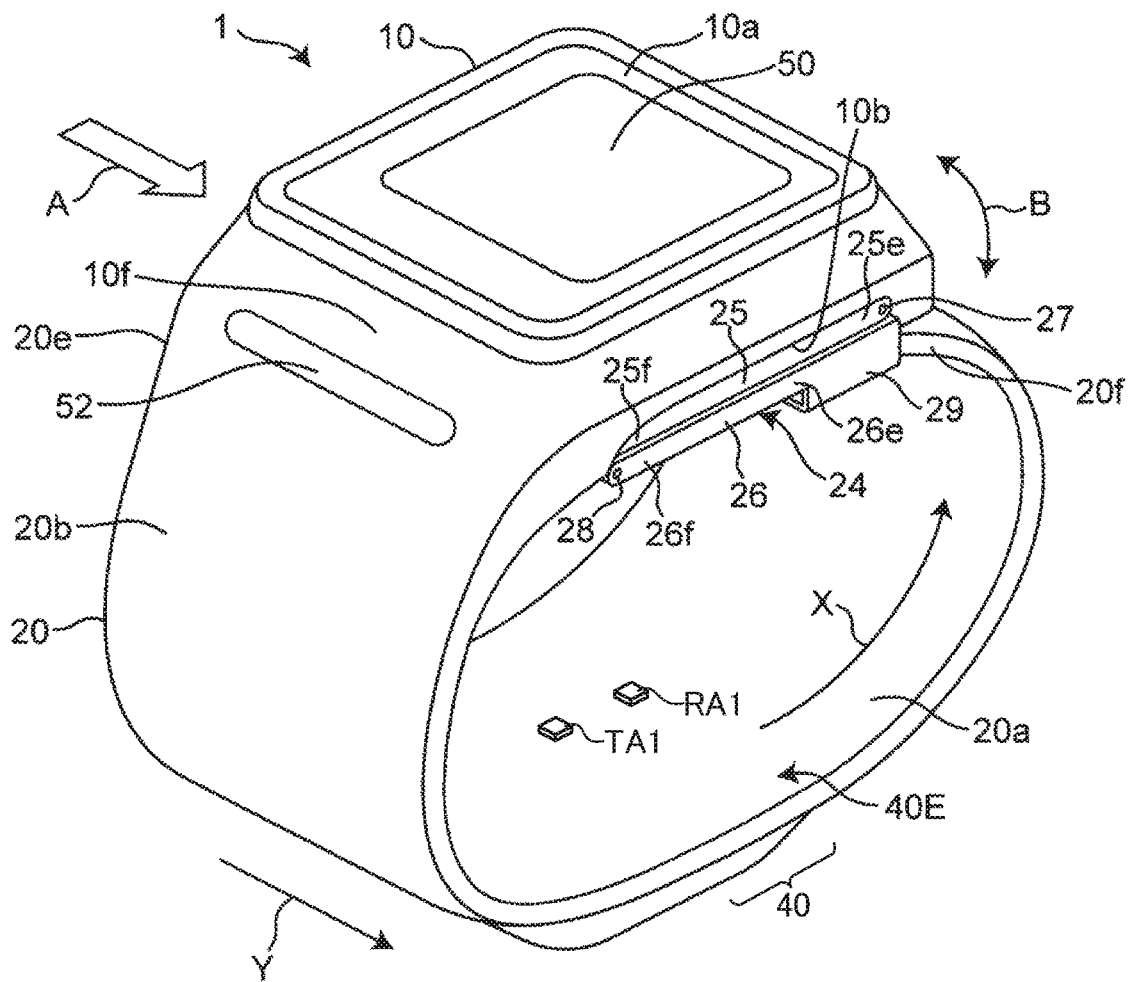
FIG. 3 is a perspective view illustrating an external appearance of a wrist-type blood pressure monitor according to the embodiment of the biological information measurement apparatus illustrated in FIG. 1.

FIG. 3 is a perspective view illustrating an external appearance of a wearable device (the entirety of which is denoted by a reference numeral 1) as a biological information measurement apparatus according to the first embodiment of the present invention. Here, a wrist-type blood pressure monitor including a radio-type pulse sensor will be described as an example of the wearable device 1. FIG. 4 is a plan view schematically illustrating attachment positions of antenna elements TA1 and RA1 of the pulse sensor in a state in which the blood pressure monitor 1 is attached to a left wrist 90 as a measurement site (hereinafter referred to as "an attached state"). In FIG. 4, 90a indicates the palm-side surface of the left wrist 90, and 91 indicates the position of the radial artery 91.

As shown in FIG. 3 and FIG. 4, the blood pressure monitor 1 includes, broadly, a strap 20 to be worn around the left wrist 90 of the user and a main body 10 integrally attached to the strap 20. The blood pressure monitor 1 corresponds to a blood pressure measurement apparatus including a pair of pulse sensors. In these figures, a pulse sensor is formed of a transmission antenna element TA1 and a reception antenna element RA1 that are paired and spaced apart from each other so as to straddle the radial artery 91.

As shown in FIG. 3, the strap 20 has an elongated band-like shape so as to surround the left wrist 90 along the circumferential direction, and includes an inner peripheral surface 20a in contact with the left wrist 90, and an outer peripheral surface 20b opposite the inner peripheral surface 20a. The dimension (width dimension) of the strap 20 in a width direction Y is set to about 30 mm in this example.

The main body 10 is integrally provided at one end 20e of the strap 20 in the circumferential direction by integral molding in this example. The strap 20 and the main body 10 may be separately formed, and the main body 10 may be integrally attached to the strap 20 via an engaging member (for example, a hinge). In this example, the portion where the main body 10 is disposed is intended to correspond to the back side surface (surface on the back side of the hand) of the left wrist 90 in the attached state.

As can be seen in FIG. 3, the main body 10 has a three-dimensional shape having a thickness in a direction perpendicular to the outer peripheral surface 20*b* of the strap 20. The main body 10 is formed to be small and thin so as not to interfere with daily activities of the user. In this example, the main body 10 has a contour of a truncated quadrangular pyramid shape protruding outward from the strap 20.

The display 50 forming a display screen is provided on a top surface 10*a* (a surface farthest from the measurement site) of the main body 10. In this example, the display 50 is an organic electro-luminescence (EL) display, and displays information on blood pressure measurement, such as a blood pressure measurement result, and other information in accordance with a control signal from a control unit (not shown). The display 50 is not limited to the organic EL display, and may be another type of display such as a liquid crystal display (LCD).

Further, a controller 52 for inputting an instruction from the user is provided on a side surface 10*f* (a side surface on the left front side in FIG. 2) of the main body 10. In this example, the controller 52 is composed of a push switch, to which an operation signal corresponding to an instruction to start or stop blood pressure measurement is input by the user. The controller 52 is not limited to the push switch, and may be, for example, a pressure-sensitive (resistance-type) or proximity (electrostatic capacitance-type) touch panel switch. Further, a microphone (not shown) may be provided to input an instruction to start blood pressure measurement with a user's voice.

A transmission/reception unit 40 constituting the pulse sensor is provided at a portion of the strap 20 between one end 20*e* and the other end 20*f* in the circumferential direction. A transmission/reception antenna unit 40E is mounted as the sensor unit 2, including the antenna elements TA1 and RA1 on the inner peripheral surface 20*a* of a portion of the strap 20 where the transmission/reception unit 40 is disposed. In this example, the range occupied by the transmission/reception antenna unit 40E in a longitudinal direction X of the strap 20 is intended to correspond to the radial artery 91 of the left wrist 90 in the attached state (see FIG. 4).

As shown in FIG. 3, a bottom surface 10*b* (surface closest to the measurement site) of the main body 10 and an end portion 20*f* of the strap 20 are connected by a threefold buckle 24. The buckle 24 includes a first plate member 25 disposed on the outer peripheral side and a second plate member 26 disposed on the inner peripheral side. One end portion 25*e* of the first plate member 25 is rotatably attached to the main body 10 via a connecting rod 27 extending along the width direction Y. The other end portion 25*f* of the first plate member 25 is rotatably attached to one end portion 26*e* of the second plate member 26 via a connecting rod 28 extending along the width direction Y. The other end portion 26*f* of the second plate member 26 is fixed near the end portion 20*f* of the strap 20 by a fixing unit 29. The mounting position of the fixing unit 29 in the longitudinal direction X of the strap 20 (which corresponds to the circumferential direction of the left wrist 90 in the attached state) is variably set in advance in accordance with the circumferential length of the left wrist 90 of the user. Thus, the blood pressure monitor 1 (the strap 20) is formed in a substantially annular shape as a whole, and the bottom surface 10*b* of the main body 10 and the end portion 20*f* of the strap 20 can be opened and closed in the direction of the arrow B by the buckle 24.

When the blood pressure monitor 1 is to be worn on the left wrist 90, the buckle 24 is opened to increase the diameter of the loop of the strap 20. In this state, the user passes the left hand through the strap 20 in the direction indicated by the arrow A in FIG. 2. The user then adjusts the angular position of the strap 20 around the left wrist 90 to position the transmission reception unit 40 of the strap 20 over the radial artery 91 passing through the left wrist 90. As a result, the transmission/reception antenna unit 40E of the transmission/reception unit 40 comes into contact with the palm-side surface 90*a* of the left wrist 90 corresponding to the radial artery 91. In this state, the user closes and fixes the buckle 24. In this way, the user wears the blood pressure monitor 1 (strap 20) on the left wrist 90.

As shown in FIG. 4, in the attached state, the transmission/reception antenna unit 40E of the transmission/reception unit 40 includes the transmission antenna element TA1 and the reception antenna element RA1 corresponding to the radial artery 91 of the left wrist 90.

In this example, the transmission antenna element TA1 or the reception antenna element RA1 has a square-shaped pattern of about 3 mm in length and width in a planar direction (which means the direction of the paper surface in FIG. 3) so as to be able to emit or receive radio waves of frequencies in a 24 GHz band.

The antenna element TA1 has a conductive layer (not shown) to emit radio waves. A dielectric layer is attached along a surface of the conductive layer facing the left wrist 90 (the same configuration is applied to the reception antenna element RA1). In the attached state, the conductive layer faces the palm-side surface 90*a* of the left wrist 90, and the dielectric layer serves as a spacer to keep the distance between the palm-side surface 90*a* of the left wrist 90 and the conductive layer constant. This makes it possible to accurately measure biological information from the left wrist 90.

The conductive layer is made for example, a metal (copper or the like). The dielectric layer is made of, for example, polycarbonate, so that the relative permittivity of the dielectric layer is uniformly set to $\varepsilon\ \Gamma \approx 3.0$. The relative permittivity means a relative permittivity at a frequency in the 24 GHz band of radio waves used for transmission and reception.

The transmission/reception antenna unit 40E can be configured to be flat along a surface direction. Therefore, in this blood pressure monitor 1, the entirety of the strap 20 can be made thin.

Although FIG. 3 and FIG. 4 show the blood pressure monitor 1 including a pair of antennas as the pulse sensor, the number of antennas is not limited thereto. For example, more antenna pairs may be provided so that pulse wave sensing can be performed at multiple points. Further, it is not always necessary to use an antenna pair including a transmission antenna and a reception antenna; that is, an antenna for both transmission and reception may be used. Further, the pair of the transmission antenna and the reception antenna need not be fixed: a plurality of reception antennas may be provided for one transmission antenna, and the antennas used for wave reception may be freely switched to perform transmission and reception of radio waves; or a plurality of transmission antennas may be provided for one reception antenna and the antennas used for wave transmission may be freely switched. The blood pressure measurement method of the blood pressure monitor 1 may be a method using a pulse sensor or a method not using a pulse sensor, and various methods such as a pulse transit time (PTT) method and an oscillometric method are applicable.

(2) Functional Configuration of Wearable Device

FIG. 5 is a block diagram illustrating an example of a functional configuration of the blood pressure monitor 1 according to the first embodiment of the present invention. The blood pressure monitor 1 includes the sensor unit 2, a processing unit 12, a storage unit 14, an input/output interface 16, a communication interface 17, the display 50, and the controller 52. Of these elements, the processing unit 12, the storage unit 14, the input/output interface 16, the communication interface 17, the display 50, and the display controller 52 are provided in the main body 10.

The input/output interface 16 has, for example, function of receiving an instruction input by the user via the controller 52 and outputting display information generated by the processing unit 12 to the display 50.

The communication interface 17 has, for example, a wired or wireless interface, and enables transmission and reception of information to and from a terminal carried by the user, a server (not shown) arranged on a cloud, or the like via a communication network NW. In this embodiment, the network NW is the Internet, but is not limited thereto, and may be another type of network such as an in-hospital local area network (LAN). Alternatively, one-to-one communication may be performed using a USB cable or the like. The communication interface 17 may be an interface for a micro USE connector.

The storage unit 14 includes a non-volatile memory capable of writing and reading data at any time, such as a hard disk drive (HDD) or a solid state drive (SDD), and a volatile memory, such as an RAM, and also includes a program storing unit (not shown) and a reference value storage unit 141 as storage areas necessary for implementing the present embodiment.

The reference value storage unit 141 stores a reference waveform corresponding to the reference position (ideal position) or information indicative of the feature of the reference waveform. The reference waveform represents an ideal waveform of a pulse wave that is expected to be acquired when the pulse sensor of the blood pressure monitor 1 is set on the reference position. The reference waveform may be a user-specific waveform extracted from actual measurement data (for example, calculated by statistical processing from actual measurement data acquired in a predetermined period), or may be a waveform calculated as a pulse wave of an average adult.

The sensor unit 2 includes an antenna pair AT (hereinafter simply referred to as "antenna AT") as the pulse sensor and a control circuit CC connected to the antenna AT. The antenna. AT includes the transmission antenna element TA1 and the reception antenna element RA1 which are paired. The control circuit CC includes transmitter circuitry TC1 and receiver circuitry RC1 respectively connected to the transmission antenna element TA1 and the reception antenna element RA1. Both the transmission antenna element TA1 and the reception antenna element RA1 have directivity in the direction toward the measurement site including the radial artery 91. The transmitter circuitry TC1 supplies the measurement signal to the transmission antenna element TA1 at a fixed cycle, thereby transmitting the radio wave of the measurement signal from the transmission antenna element TA1 to the measurement site. The reception antenna element RA1 receives a reflected wave of the radio wave of the measurement signal reflected by the radial artery 91. The receiver circuitry RC1 generates a waveform signal corresponding to the reflected wave received by the reception antenna element RA1 and outputs the waveform signal to the processing unit 12.

The processing unit 12 includes, for example, a hardware processor such as a central processing unit (CPU) and a work memory, and also includes a pulse detector 101, the feature extraction unit 121, the determination unit 122, and the output unit 5 as processing function units according to an embodiment. These processing function units are realized by causing the hardware processor to execute a program stored in a storage unit (not shown).

The pulse detector 101 includes, for example, an AD converter ADC1 and a filter F1. The AD converter ADC1 converts the waveform signal output from the receiver circuitry RC1 into a digital signal. The filter F1 performs filtering processing on the waveform signal converted into the digital signal to remove, for example, a noise component, thereby generating a pulse wave signal PS1, and outputs it to the feature extraction unit 121. The pulse wave signal represents the pulsation of the radial artery 91 passing through the left wrist 90 at the position where the antenna AT is located.

The feature extraction unit 121 receives the pulse wave signal PS1 output from the pulse detector 101, and extracts a feature of the waveform (for example, an amplitude, a shape of the waveform, a peak voltage, and the like) from the pulse wave signal PS1.

The determination unit 122 receives information indicative of the feature of the waveform extracted by the feature extraction unit 121, and determines whether or not the setting position of the blood pressure monitor 1 with respect to the artery 91 as the measurement site satisfies the predetermined condition. This determination method will be described in detail later.

Operation Example

Figure 6:
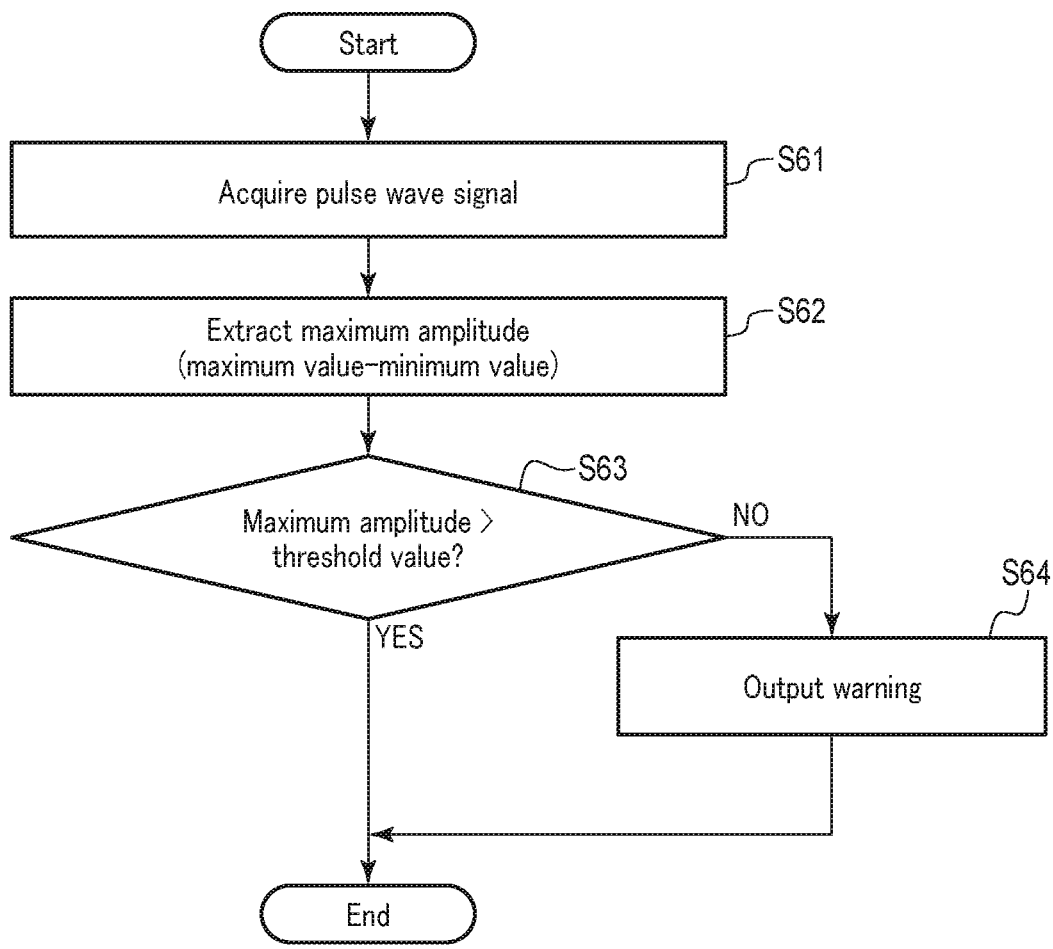
FIG. 6 is a flowchart illustrating an example of the processing procedure of the biological information measurement apparatus illustrated in FIG. 5.

Next, an operation example of the blood pressure monitor 1 configured as described above will be described. FIG. 6 is a flowchart illustrating an example of a processing procedure and processing contents of the blood pressure monitor 1 shown in FIG. 5.

The blood pressure monitor 1 starts operating in response to reception of a measurement start signal input by the user through the controller 52 after being worn around the wrist, for example. In the blood pressure monitor 1, the sensor unit 2 transmits radio waves as measurement signals from the transmitter circuitry TC1 at a fixed cycle to a plurality of different positions of the measurement site, including the radial artery 91, via the transmission antenna TA1. Then, reflected waves of the radio waves reflected by the measurement site are received by the reception antenna RA1, and waveform signals respectively corresponding to the reflected waves are generated by the receiver circuitry RC1. These waveform signals are input to the pulse detector 101 of the processing unit 12.

In step S61, the blood pressure monitor 1 performs AD conversion, filtering processing, and the like on the waveform signals output from the receiver circuitry RC by the pulse detector 101 of the processing unit 12, thereby acquiring a pulse wave signal PS1. The pulse wave signal PS1 is input to the feature extraction unit 121.

In step S62, the blood pressure monitor 1 obtains, at a fixed repetition cycle, a maximum amplitude (a maximum amplitude value—a minimum amplitude value) as a feature of the waveform through the feature extraction unit 121 from the input pulse wave signal PS1. The maximum amplitude can be calculated, for example, with a sampling interval of 1 millisecond (msec) and a cycle of 1 second.

Figure 7A:
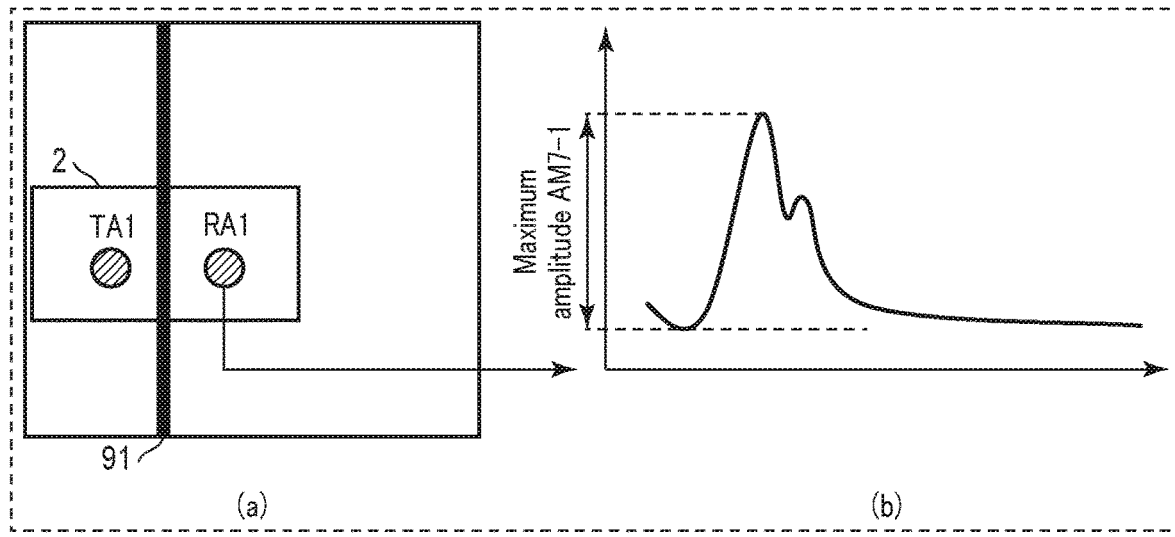
FIG. 7A is a schematic diagram illustrating an example of the relative positional relationship between an artery and an antenna, and a pulse wave signal obtained therefrom, which is assumed in the processing procedure illustrated in FIG. 6.
Figure 7B:
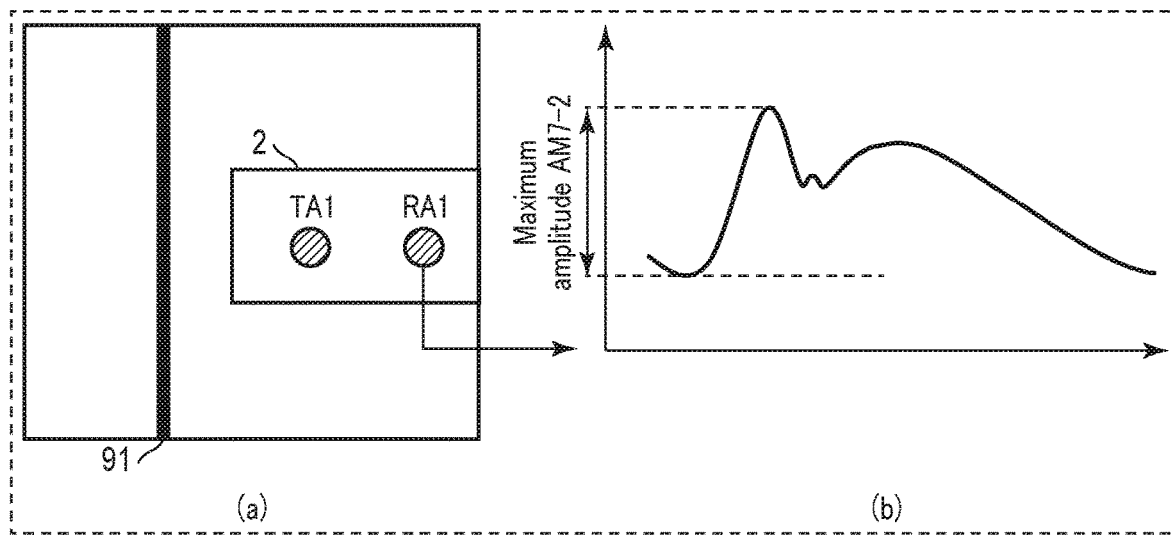
FIG. 7B is a schematic diagram illustrating another example of the relative positional relationship between an artery and an antenna, and a pulse wave signal obtained therefrom, which is assumed in the processing procedure illustrated in FIG. 6.

FIGS. 7A and 7B explain the processing operation illustrated in FIG. 6, in which (a) shows the assumed position of the antennas with respect to the radial artery 91, and (b) shows an example of the obtained pulse wave signal. The pulse wave signal is detected as a change in voltage value with respect to a time axis. However, the pulse wave signals shown in (b) of FIG. 7A and FIG. 7B are merely examples for convenience in explaining the determination method according to the first embodiment, and are not limited thereto. The same applies to the subsequent drawings.

As shown in (a) of FIG. 7A, when the transmission antenna element TA1 and the reception antenna element RA1 are arranged at symmetrical positions on both sides of the radial artery 91 in a state where the blood pressure monitor 1 is worn on the left wrist, the sensor unit 2 can obtain an ideal waveform with relatively little noise and mainly representing arterial pulsation. At this time, it is considered that the maximum amplitude AM7-1 takes the largest value in comparison with the other setting positions.

On the other hand, as shown in (a) of FIG. 7B, when the sensor unit 2 is at a position away from the radial artery 91, noise components are superimposed on the obtained pulse wave signal. In this case, it may be difficult to specify a pulsation. The noise components may be derived from the pulse wave from the ulnar artery or the movement of other body tissues. At this time, a maximum amplitude AM7-2 is expected to be smaller than the maximum amplitude AM7-1. The relationship between the arrangement position shown in (a) and the waveform image of the pulse wave shown in (b) in FIG. 7A and FIG. 7B is merely an example for description, and the arrangement position shown in FIG. 7A (a) does not necessarily correspond to the reference position (ideal position). The same applies the subsequent drawings.

In step S63, the blood pressure monitor 1 determines, under the control of the determination unit 122, whether the obtained maximum amplitude is greater than a threshold value set in advance. The threshold value may be a fixed value or may be dynamically adjusted. The threshold value can be freely set based on past measurement results, measurement accuracy, and the like.

If it is determined in step S63 that the maximum amplitude of the acquired pulse wave signal is equal to or smaller than the threshold value, the blood pressure monitor 1 proceeds to step S64, and a notification for warning that the setting position is inappropriate can be output by the output unit 5 based on the determination result. For example, the output unit 5 may generate and output a warning message to prompt the user to move the location of the device. This message is sent to the display 50 via the input/output interface 16, for example. The display by the display 50 may be maintained for several seconds, for example. The message may be in any form, such as a language, image, sound, blinking light, or vibration. The user recognizes that the setting position of the blood pressure monitor 1 is not appropriate from the message, and can rotate the blood pressure monitor 1 in the circumferential direction of the wrist or retighten the strap 20 of the blood pressure monitor 1.

If it is determined in step S63 that the maximum amplitude of the acquired pulse wave signal is greater than the threshold value, the process ends. The blood pressure monitor 1 can then proceed to any subsequent operation, such as measurement of biological information. However, also in this case, output processing can be performed to notify the user that the setting position is appropriate or to prompt the user to input a measurement start instruction through the controller 52.

Example 1-2

Figure 8:
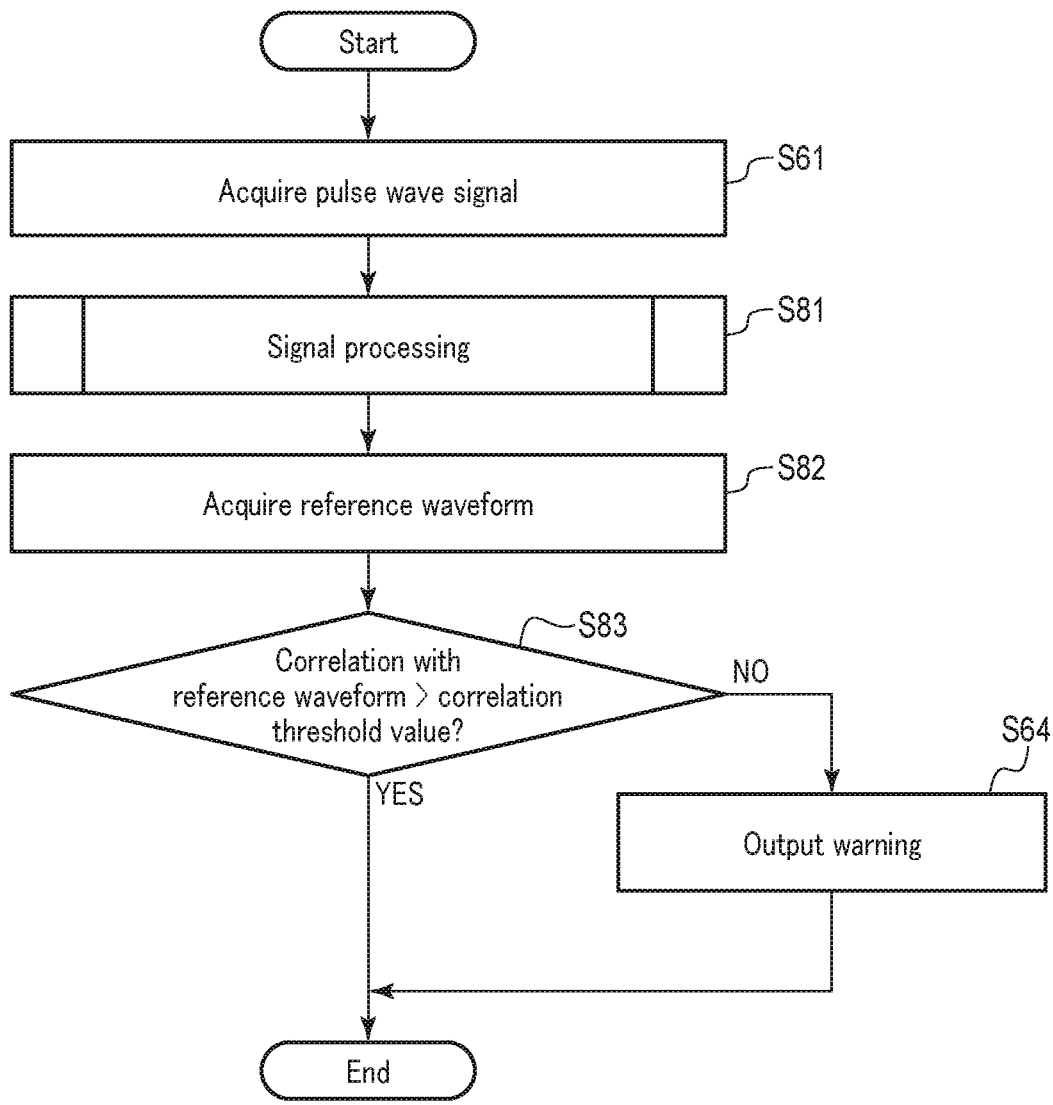
FIG. 8 is a flowchart illustrating another example of the processing procedure of the biological information measurement apparatus illustrated in FIG. 5.

FIG. 8 is a flowchart illustrating another example of the blood pressure monitor 1 according to the first embodiment. In FIG. 8, the same components as those in FIG. 6 are denoted by the same reference numerals, and a detailed description thereof will be omitted.

As explained above for Example 1-1, the blood pressure monitor 1 starts operating in response to reception of a measurement start signal input by the user through the controller 52. First, the blood pressure monitor 1 acquires a pulse wave signal in step S61. Next, in step S81, the blood pressure monitor 1 performs processing to extract a pulse-wave-derived component from the pulse wave signal under the control of the feature extraction unit 121.

Figure 9:
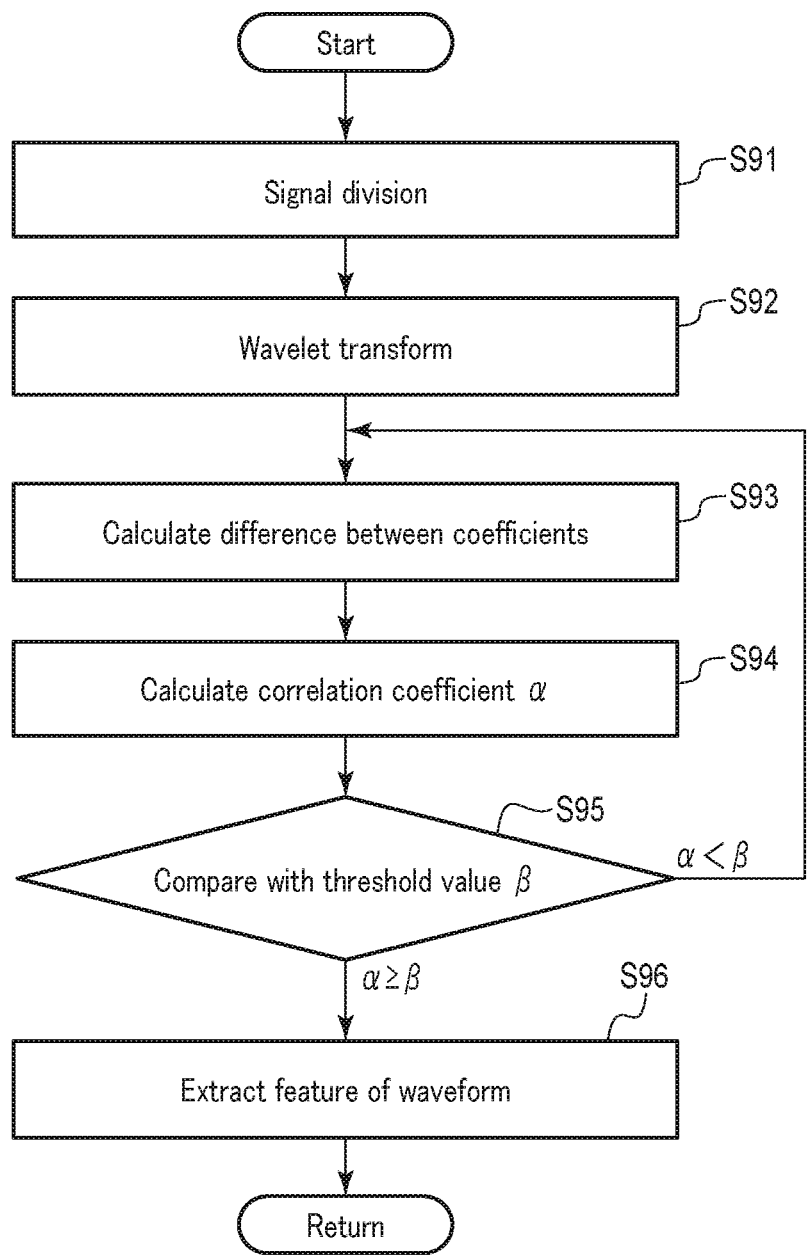
FIG. 9 is a flowchart illustrating an example of a method for extracting a waveform signal derived from a pulse wave from an acquired signal, which can be used in the processing procedure illustrated in FIG. 8.

FIG. 9 is a flowchart illustrating an example of the signal processing that can be adopted in step S81.

The acquired pulse wave signal is a mixture of various signals, and there are cases where a feature of the signal derived from the pulse wave cannot be sufficiently extracted. Thus, a feature can be extracted using, for example, wavelet transform. An example thereof will be briefly described below.

In step S91, the feature extraction unit 121 divides the pulse wave signal in time intervals (for example, time blocks in units of second). In general, it is known that when the pulse wave of the radial artery 91 is measured, the cycle is about 1 second. The time division can be performed by any known method.

In step S92, the feature extraction unit 121 applies wavelet transform to the divided pulse wave signals to obtain a wavelet coefficient. The wavelet transform is a method for analyzing a waveform by scaling, translating, and adding small waves (wavelets). A basic reference wave called a mother wavelet is:

$$\psi(t) \quad \text{[Formula 1]}$$

A reference wave obtained by scaling and translating the basic reference wave is:

$$\psi_{a,b}(t) = \frac{1}{\sqrt{a}} \psi\left(\frac{(t-b)}{a}\right) \quad \text{[Formula 2]}$$

A plurality of reference waves are prepared and a relationship of the reference waves to a pattern is examined. The symbol "a" represents a decompression parameter (scale) and the symbol "b" represents a translation parameter (translation). The wavelet transform is expressed by the following formula, and the result obtained by the transform is called a wavelet coefficient.

$$W_\psi(t)(a, b) \stackrel{def}{=} \frac{1}{\sqrt{a}} \int_{-\infty}^{\infty} h(t)\psi\left(\frac{t-b}{a}\right) dt \quad \text{[Formula 3]}$$

In step S93, the feature extraction unit 121 compares the obtained wavelet coefficient with a coefficient obtained from a preset comparison waveform, and calculates a difference therebetween. The comparison waveform is an arbitrary waveform for use in extracting a pulse wave component, and having periodicity that can be divided into time intervals in advance. For example, a waveform that has been set based on an ideal pulse wave may be used as the comparison waveform. Alternatively, a simple waveform such as a sine wave may, be used as the comparison waveform. This processing removes the frequency band caused by the non-pulse wave component.

Next, in step S94, the feature extraction unit 121 calculates a correlation coefficient α for correlation with the comparison waveform.

In step S95, the feature extraction unit 121 compares the correlation coefficient α with a threshold value β, and repeats the processing from step S93 to step S95 until the correlation coefficient reaches the threshold value. If the correlation coefficient α reaches the threshold value β, it is determined that a desired signal has been extracted, and the process proceeds to step S96. The feature extraction unit 121 extracts the feature of the waveform in step S96 and ends the processing.

Next, in step S82, the blood pressure monitor 1 acquires a reference waveform for correlation with the pulse wave signal from the reference value storage unit 141. This reference waveform may be different from the basic reference waveform or the comparison waveform described in FIG. 9.

Next, in step S83, the blood pressure monitor 1 calculates the cross-correlation between the waveform extracted from the pulse wave signal and the reference waveform for the corresponding arbitrary time interval, and determines whether the obtained correlation value is larger than a preset correlation threshold value (for example, 0.7). Since the method of obtaining the correlation value is generally known, it will not be described in detail here.

If it is determined in step S83 that the correlation value is larger than the threshold value, it is determined that the condition corresponding to the reference position is satisfied, and the processing ends. If it is determined in step S63 that the correlation value is equal to or smaller than the threshold value, it is determined that the condition corresronding to the reference position is not satisfied, and the processing proceeds to step S64 to output a warning.

Example 1-3

Figure 10:
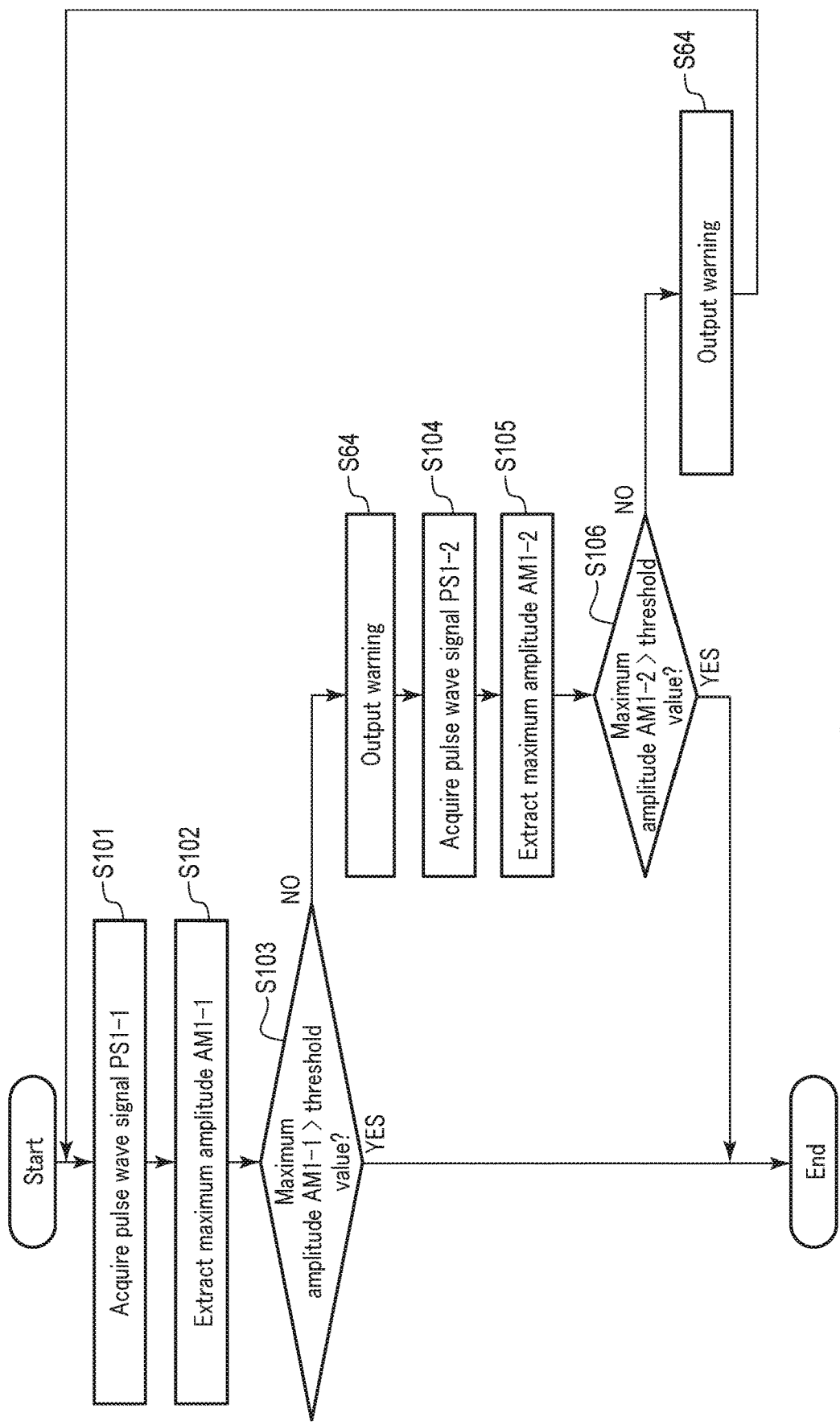
FIG. 10 is a flowchart illustrating another example of the processing procedure of the biological information measurement apparatus illustrated in FIG. 5.

FIG. 10 is a flowchart illustrating another example of the processing procedure of the blood pressure monitor 1 illustrated in FIG. 5. In FIG. 10, the same components as those in FIG. 8 are denoted by the same reference numerals, and detailed description of the same or similar processing will be omitted.

As explained above for Example 1-1, the blood pressure monitor 1 starts operating in response to reception of a measurement signal input by the user through the controller 52. In step S101, the pulse detector 101 acquires the pulse wave signal PS1. In step S102, the feature extraction unit 121 extracts a maximum amplitude AM1-1 from the pulse wave signal PS1-1.

Next, in step S103, the blood pressure monitor 1 determines, under the control of the determination unit 122, whether the extracted maximum amplitude AM1-1 satisfies a predetermined condition, in this example, whether the maximum amplitude AM1-1 is greater than the threshold value set in advance. However, in step S103, it is also possible to determine whether the predetermined condition is satisfied by taking the correlation with the reference waveform in the same manner as in Example 1-2 described above, and it is also possible to perform the determination based on, other features of the waveform such as the cycle or the spectrum intensity. If it is determined in step S103 that the maximum amplitude AM1-1 is greater than the threshold value, it is determined that the setting position of the blood pressure monitor 1 is appropriate; and the processing ends.

In step S103, if it is determined that the maximum amplitude AM1-1 is equal to or smaller than the threshold value, the blood pressure monitor 1 proceeds to step S64, and information indicative of the determination result is output by the output unit 5. For example, the output unit 5 generates a warning message for notifying the user that the setting position is inappropriate, and outputs the warning message to the display 50.

Figure 11A:
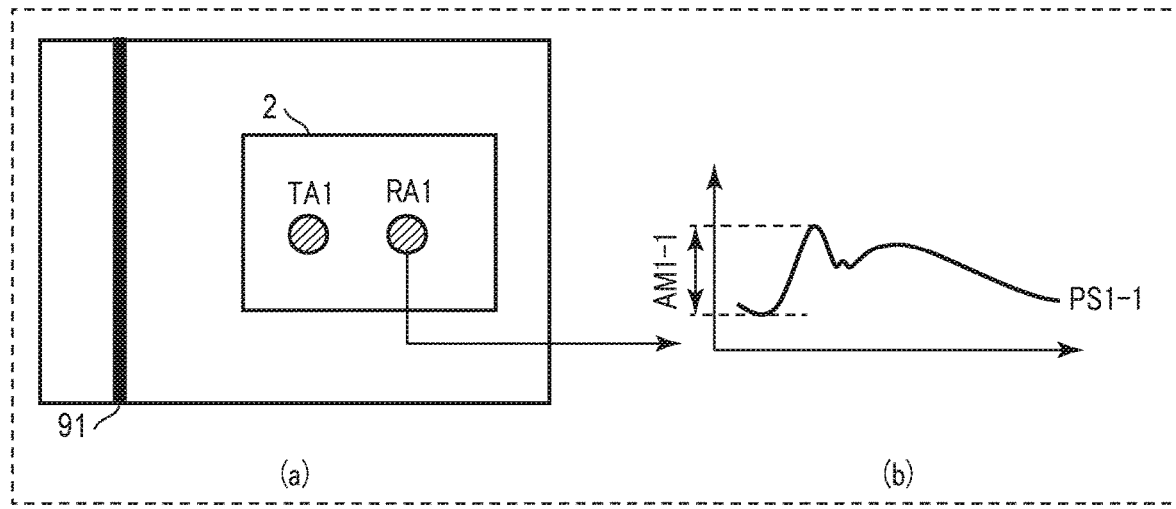
FIG. 11A is a schematic diagram illustrating an example of the relative positional relationship between an artery and an antenna, and a pulse wave signal obtained therefrom, which is assumed in the processing procedure illustrated in FIG. 10.
Figure 11B:
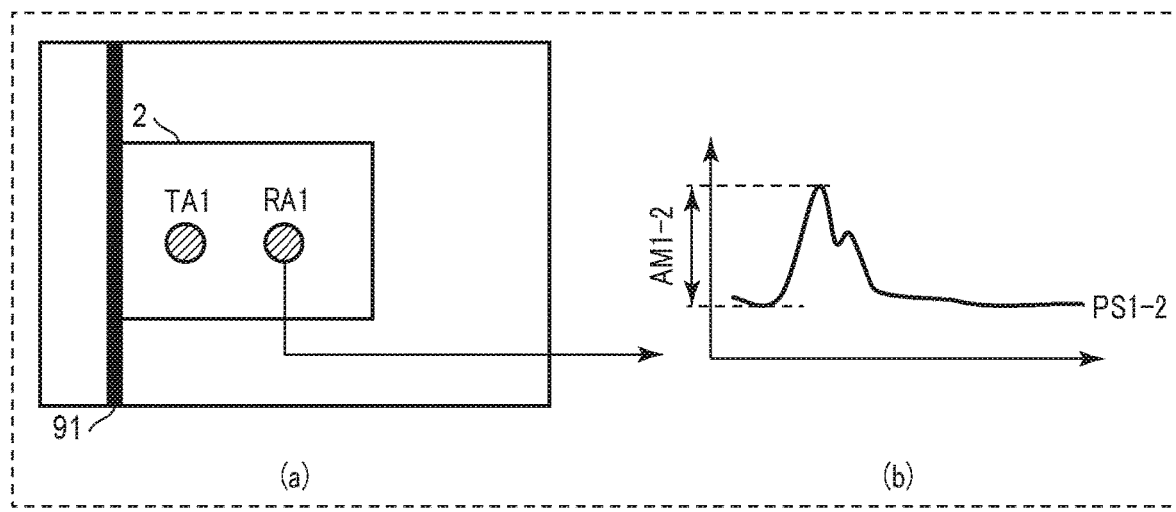
FIG. 11B is a schematic diagram illustrating another example of the relative positional relationship between an artery and an antenna, and a pulse wave signal obtained therefrom, which is assumed in the processing procedure illustrated in FIG. 10.

FIGS. 11A and 11B explain the processing operation illustrated in FIG. 10, in which (a) shows the position of the antenna with respect to the radial artery 91, and (b) shows an example of the obtained pulse wave signal. For example, when the sensor unit 2 is located at the pdsition shown in (a) of FIG. 11A, since the antenna is positioned away from the radial artery 91, the obtained pulse wave signal does not satisfy the condition corresponding to the reference position; the setting position of the blood pressure monitor 1 is thus determined to be inappropriate, and a warning is output. In this example, the blood pressure monitor 1 does not immediately end the operation after outputting the warning, but enters a standby state until the predetermined condition is satisfied. In the meantime, the user who receives the notification can adjust the setting position by rotating the blood pressure monitor 1 around the wrist, or retighten the strap 20 so that the transmission/reception antenna unit 40E is in close contact with the skin, or the like. However, the following processing does not necessarily require the user adjust the position.

When the predetermined condition is satisfied, for example, when a predetermined time has elapsed, when an input operation from the user is received, or when movement of the blood pressure monitor 1 is detected by an accelerometer (not shown) included in the blood pressure monitor 1, the blood pressure monitor 1 in the standby state may proceed to step S104 to perform the processing at a second time. Specifically, in step S104, the blood pressure monitor 1 again acquires a pulse wave signal PS1-2, extracts a maximum amplitude AM1-2 in step S105, and determines in step S106 whether the maximum amplitude AM1-2 satisfies a predetermined condition, in this example, whether the maximum amplitude AM1-2 is greater than the threshold value set in advance. At this time, the position of the sensor unit 2 may remain unchanged at the position shown in (a) of FIG. 11A, or may have moved to the position shown in (a) of FIG. 11B, but this detection is not always necessary in this example.

If it is determined in step S106 that the extracted maximum amplitude AM1-2 is greater than the threshold value set in advance, it is estimated that the setting position of the blood pressure monitor 1 is appropriate, and the processing ends. On the other hand, if it is determined in step S106 that the maximum value AM1-2 is equal to or smaller than the threshold value, the process proceeds to step S64, and the blood pressure monitor 1 outputs a warning again as a determination result through the output unit 5. Whether or not the condition corresponding to the reference position is satisfied when the antenna is at the position shown in (a) of FIG. 11B depends on the setting of the threshold. In addition, in the method described for FIG. 10, the measurement is performed at least twice until the condition is satisfied in the alignment process; however, it is also possible to set up further performances of the measurement more times until the condition is satisfied in the alignment process.

In the above example, the method of comparing the maximum amplitude with the preset threshold value has been described as the method of determining whether the condition corresponding to the reference position is satisfied. However, the method of comparing the correlation value with respect to the reference waveform with the threshold value as in Example 1-2 may be used, or a determination method based on another feature of the waveform, such as the cycle or the spectral intensity, may be used. The operations of steps S104 to S106 may be the same as or different from those of steps S101 to S103. For example, the threshold value used in step S103 and the threshold value used in step S106 may be the same or different. In addition, different determination methods may be used in step S103 and step S106; for example, the maximum amplitude may be compared with the threshold value in step S103 and the correlation value with respect to the reference waveform may be used in step S106.

Example 1-4

FIG. 12 is a block diagram illustrating another example of the functional configuration of the blood pressure monitor 1 according to the first embodiment of the present invention. In FIG. 12, the same components as those in FIG. 5 are denoted by the same reference numerals, and a detailed description thereof will be omitted.

The blood pressure monitor 1 includes a plurality of antennas AT1, AT2, . . . and a plurality of control circuits CC1, CC2, . . . connected to the respective antennas in a sensor unit 2. Each antenna and each control circuit have the same configurations and functions as those of the antenna AT and the control circuit CC described for FIG. 5.

The processing unit 12 includes a plurality of pulse detectors 101-1, 101-2, . . . . The pulse detectors are respectively connected to the control circuits CC1, CC2, . . . , and generate pulse wave signals PS1, PS2, . . . , respectively from waveform signals output from receiver circuitry RC1, RC2, . . . , similarly to the pulse detector 101 described for FIG. 5.

The processing unit 12 further includes an antenna control unit 111. The antenna control unit 111 can select one or more antennas for use in measurement from among the plurality of antennas AT1, AT2, . . . .

Figure 13:
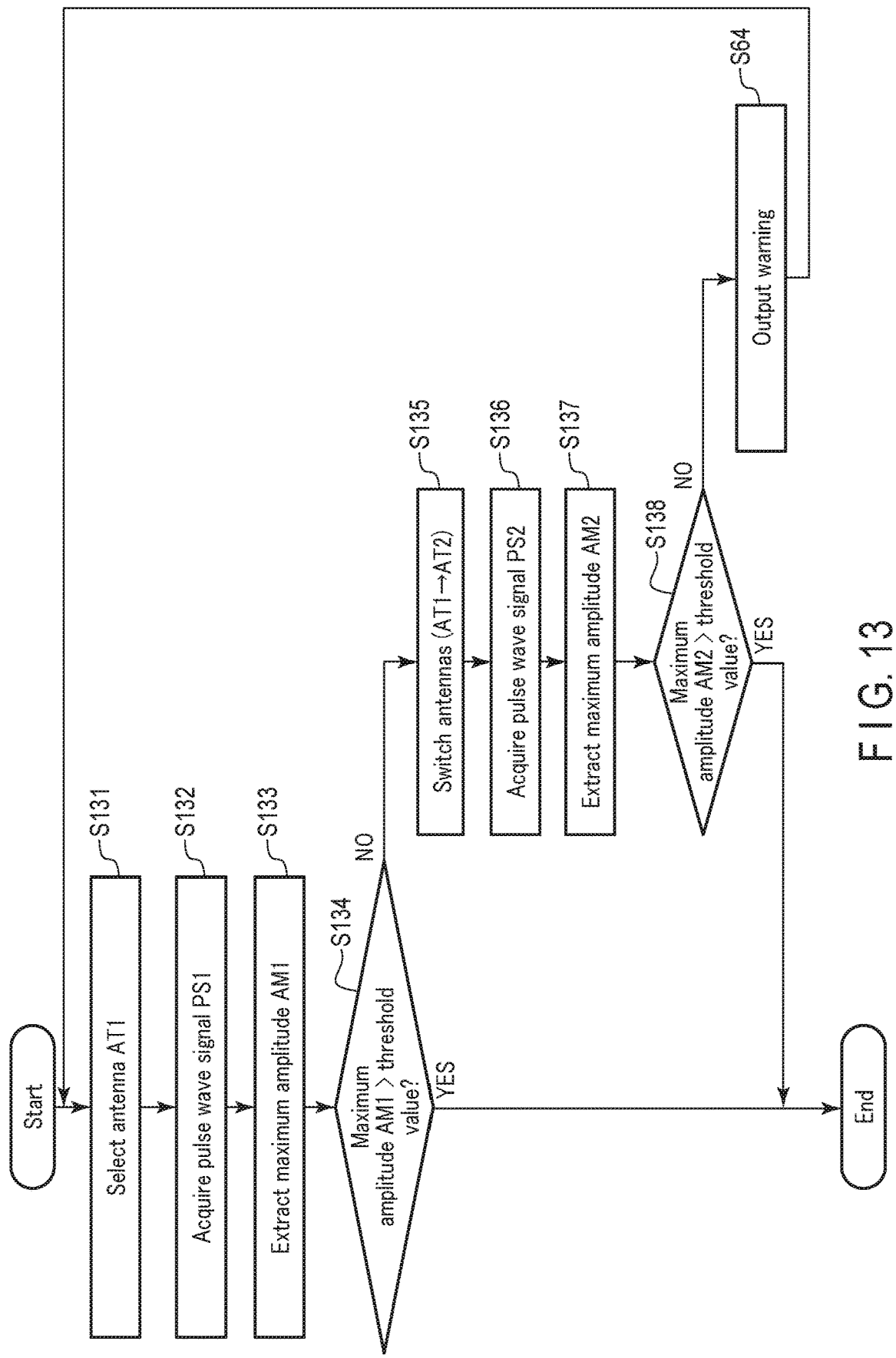
FIG. 13 is a flowchart illustrating an example of the processing procedure of the biological information measurement apparatus illustrated in FIG. 12.

FIG. 13 is a flowchart illustrating an example of the processing procedure of the blood pressure monitor 1 illustrated in FIG. 12. In FIG. 13, the same components as those in FIG. 6 are denoted by the same reference numerals, and a detailed description thereof will be omitted.

As explained above for Example 1-1, the blood pressure monitor 1 starts operating in response to reception of a measurement start sdgnal input by the user through the controller 52. First, in step S131, the blood pressure monitor 1 selects the antenna AT1 as an antenna to be used for measurement. Next, as in Example 1-1, the blood pressure monitor 1 acquires the pulse wave signal PS1 in step S132 through the pulse detector 101, extracts a maximum amplitude AM1 from the pulse wave signal PS1 in step S133 through the feature extraction unit 121, and determines in step S134 whether the maximum-amplitude AM1 is greater than a threshold value set in advance. If it is determined in step S134 that the maximum amplitude AM1 is greater than the threshold value, the process may end.

On the other hand, if it is determined in step S134 that the maximum amplitude AM1 is equal to or smaller than the threshold value, the process proceeds to step S135, and the blood pressure monitor 1 switches the antenna AT1 used for measurement to the antenna AT2 under the control of the antenna control unit 111. Next, similarly to the processing described in steps S132 to S134, the pulse wave signal PS2 is acquired in step S136 using the antenna AT2, a maximum amplitude AM2 is extracted from the pulse wave signal PS2 in step S137, and it is determined in step S138 whether or not the maximum amplitude AM2 is greater than the threshold value.

If it is determined in step S138 that the maximum amplitude AM2 is greater than the threshold value, the process may end. On the other hand, if it is determined in step S138 that the maximum amplitude AM2 is equal to or smaller than the threshold value, the process proceeds to step S64, and a warning indicating the inappropriateness of the setting position is output.

The switching between the antennas in step S135 may be automatically performed under the control of the antenna control unit 111. Alternatively, if it is determined in step S134 that the maximum amplitude AM1 is equal to or smaller than the threshold value, a warning or the like may be output to allow the user to perform antenna switching via the controller 52.

Figure 14:
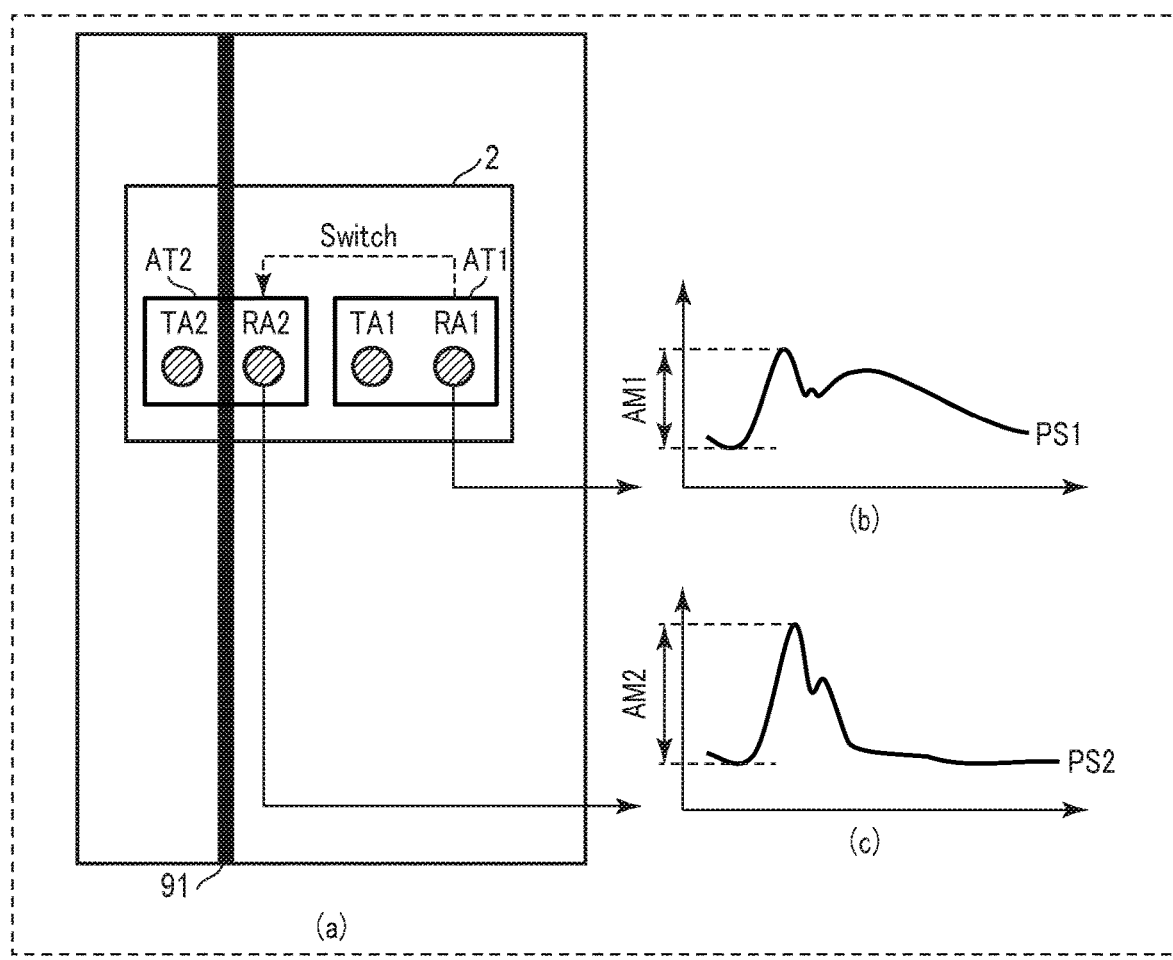
FIG. 14 is a schematic diagram illustrating an example of the relative positional relationship between an artery and an antenna, and a pulse wave signal obtained therefrom, which is assumed in the processing procedure illustrated in FIG. 13.

FIG. 14 explains the processing operation illustrated in FIG. 13, in which (a) shows the positions of the antennas AT1 and AT2 with respect to the radial artery 91, and (b) and (c) show examples of pulse wave signals PS1 and PS2 obtained through the antennas AT1 and AT2, respectively.

First, the antenna AT1 is selected in step S131, and a series of processes of steps S132 to S134 are performed. At the position shown in (a) of FIG. 14, since the antenna AT1 is positioned away from the radial artery 91, it is determined in step S134 that the maximum value AM1 is equal to or smaller than the threshold value. In this case, the blood pressure monitor 1 does not immediately end the operation, but automatically switches between the antennas by the antenna control unit 111 or prompts the user to perform an antenna switching operation, and proceeds with a series of processes (steps S136 to S138) again using the antenna AT2. At the position shown in (a) of FIG. 14, it is expected that a pulse waveform having a greater maximum amplitude is obtained when the antenna AT2 is used than when the antenna AT1 is used. In this way, by switching between the antennas AT1 and AT2, an appropriate antenna position can be evaluated without changing the wearing position of the blood pressure monitor 1, and the adjustment of the setting position becomes easier.

In the above example, the method of comparing the maximum amplitude with the preset threshold value has been described as the method of determining whether the condition corresponding to the reference position is satisfied. However, it is also possible to use the method of comparing the correlation value with respect to the reference waveform with the threshold value as in Example 1-2, or a determination method based on another feature of the waveform, such as the cycle or the spectral intensity. The operations of steps S136 to S138 may be the same as or different from those of steps S132 to S134. For example, the threshold value used in step S134 and the threshold value used in step S138 may be the same or different. In addition, different determination methods may be used in step S134 and Step S134; for example, the maximum amplitude may be compared with the threshold value in step S134 and the correlation value with respect to the reference waveform may be used in step S134.

The method described in the above embodiment can also be applied to a case where the transmission antenna elements TA1 and TA2 and the reception antenna elements RA1 and RA2 are not paired. For example, in a series of operations at a first time (steps S132 to S134), transmission and reception of radio waves may be performed using the first transmission antenna element TA1 and the first reception antenna element RA1, and in a series of operations at a second time (steps S136 to S138), transmission and reception of radio waves may be performed using the first transmission antenna element TA1 and the second reception antenna element RA2. That is, in step S135, a series of operations may be repeated by switching only the antenna element used for reception or only the antenna element used for transmission. Thus, the number of transmission antenna elements and the number of reception antenna elements need not be the same.

(Effects and Advantages of First Embodiment)

As described above in detail, in the first embodiment, the feature extraction unit 121 of the blood pressure monitor 1 extracts the feature of the waveform from the pulse wave signal PS1 output from the pulse detector 101, and then the determination unit 122 of the blood pressure monitor 1 determines whether the setting position, of the antenna AT with respect to the radial artery 91, which is the measurement site, satisfies the condition corresponding to the preset reference position based on the extracted feature of the waveform.

Therefore, it is possible to obtain an index for determining whether or not the setting position of the blood pressure monitor 1 is appropriate with a simple and inexpensive configuration, and without separately providing a position detection sensor such as an acceleration sensor. In addition, it is possible for the user to confirm that the wearing position of the blood pressure monitor 1 is not appropriate and to appropriately adjust the wearing position of the blood pressure monitor 1.

Further, according to the first embodiment, it is possible to simply and easily determine whether or not the setting position is appropriate by extracting the maximum amplitude from the pulse wave signal acquired in the process of aligning and comparing the maximum amplitude with the preset threshold value, or by obtaining the correlation between the acquired pulse wave signal and the reference waveform and comparing the correlation value with the preset threshold value. Accordingly, the convenience of the user is improved.

In addition, since the measurement can be started after confirming that the setting position of the blood pressure monitor 1 is appropriate, improvement in measurement accuracy and reliability can also be expected. Furthermore, since a complicated evaluation device is not required, it is possible to realize simplification, miniaturization, and cost reduction, while improving the robustness of setting the sensor. In addition, through the configurations to perform measurement and determination a plurality of times in the process of alignment, it is possible to increase the reliability of determination by, for example, performing repeated processing at the same setting position; or it is possible to determine appropriateness or inappropriateness of the position while the user freely performs adjustment, for example, by re-measurement after changing the setting position of the blood pressure monitor 1 or after fine adjustment of the area or angle of contact with the skin, thus greatly improving the convenience. Further, in the case of the blood pressure monitor 1 including a plurality of antennas, by switching between the antennas and repeating the measurement, is possible to evaluate a plurality of antenna positions for a single wearing position without changing the wearing position of the blood pressure monitor 1. Accordingly, the setting position can be adjusted more easily.

Second Embodiment

Example 2-1

Figure 15:
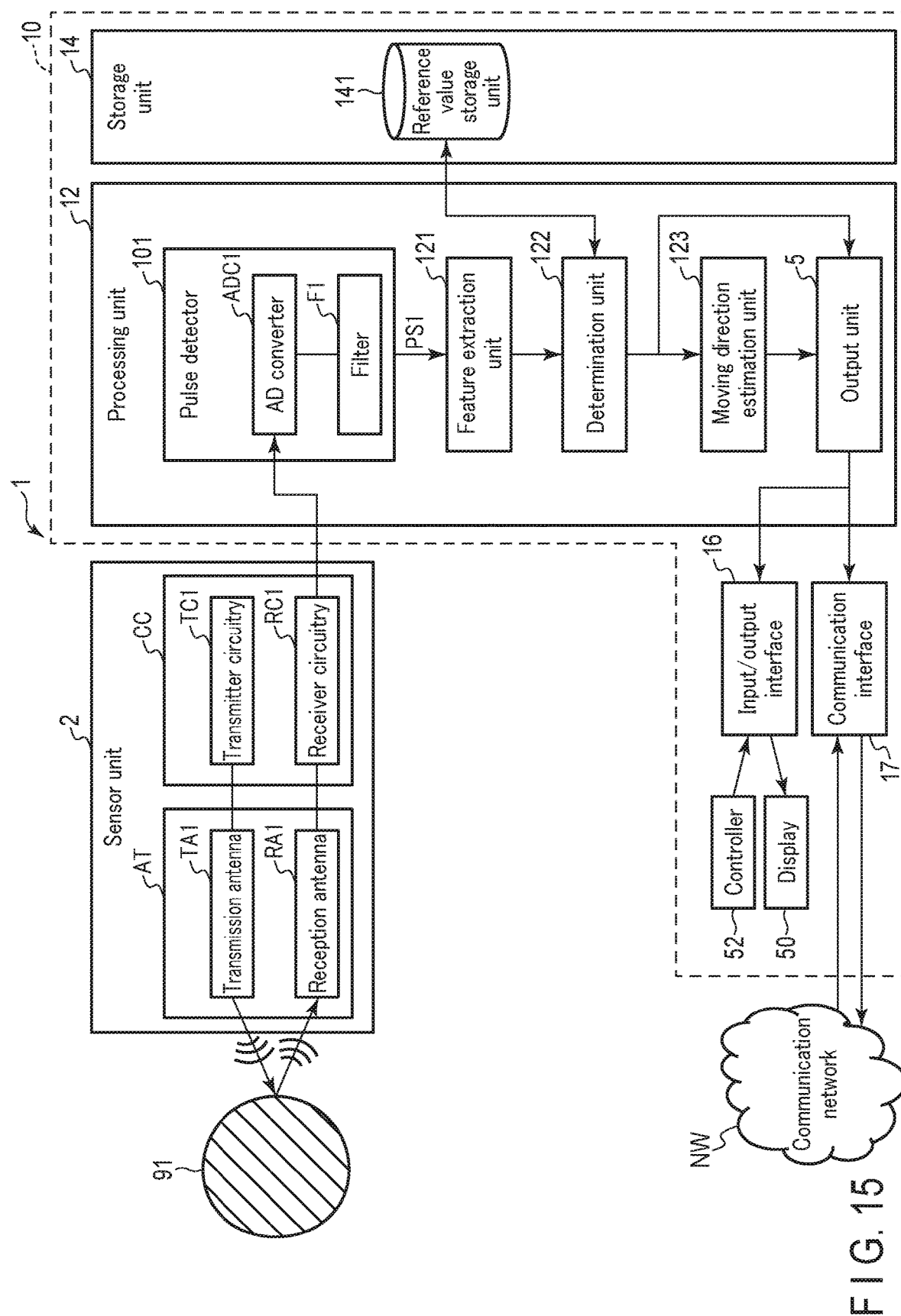
FIG. 15 is a block diagram illustrating an example of a functional configuration of the biological information measurement apparatus according to the embodiment of the present disclosure.

FIG. 15 is a block diagram illustrating a functional configuration of a blood pressure monitor 1 including a pair of antennas AT according to a second embodiment of the present invention. In FIG. 15, the same components as those in FIG. 5 are denoted by the same reference numerals, and a detailed description thereof will be omitted.

The processing unit 12 further includes a moving direction estimation unit 123. The moving direction estimation unit 123 estimates a direction in which the setting position should be moved (corrected) based on a plurality of measurement results.

Figure 16:
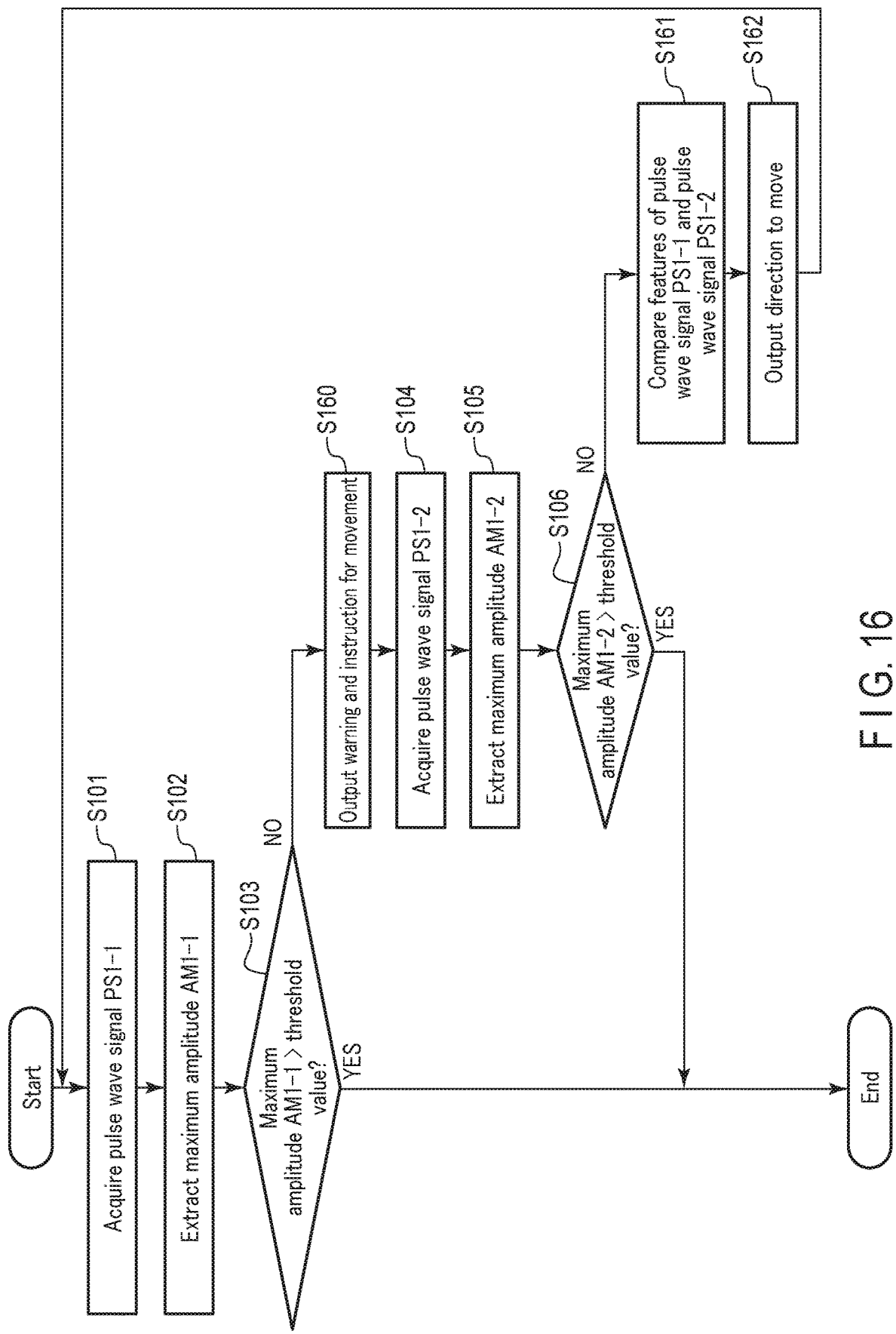
FIG. 16 is a flowchart illustrating an example of the processing procedure of the biological information measurement apparatus illustrated in FIG. 15.

FIG. 16 is a flowchart illustrating an example of the processing procedure of the blood pressure monitor 1 illustrated in FIG. 15. In FIG. 16, the same components as those in FIG. 10 are denoted by the same reference numerals, and a detailed description thereof will be omitted.

As in the first embodiment, the blood pressure monitor 1 starts operating in response to reception of a measurement start signal input by the user through the controller 52. As a series of operations at a time, the blood pressure monitor 1 acquires a pulse wave signal PS1-1 in step S101, extracts a maximum amplitude AM1-1 from the pulse wave signal PS1-1 in step S102, and determines in step S103 whether the maximum amplitude AM1-1 is greater than a threshold value set in advance. If it is determined in step S103 that the maximum amplitude AM1-1 is greater than the threshold value, the process may end.

On the other hand, if it is determined in step S103 that the maximum value AM1-1 is equal to or smaller than the threshold value, the blood pressure monitor 1 proceeds to step S160, and notifies the user that the position of the antenna AT with respect to the radial artery 91 is inappropriate, and prompts the user to correct the setting position. After outputting a warning, the blood pressure monitor 1 enters a standby state.

If a predetermined condition is satisfied (for example, if a certain period of time has elapsed), the blood pressure monitor 1 in the standby state proceeds to step S105 and can perform a series of processes at a second time in the same manner as described with reference to FIG. 10. Specifically, in step S104, the blood pressure monitor 1 acquires a pulse wave signal PS1-2 again, extracts a maximum amplitude AM1-2 in step S105, and determines in step S106 whether the maximum amplitude AM1-2 satisfies a predetermined condition, in this example, whether the maximum amplitude AM1-2 is greater than the threshold value set in advance. If it is determined in step S106 that the maximum amplitude AM1-2 is greater than the threshold value, the process may end.

On the other hand, if it is determined in step S106 that the maximum amplitude AM1-2 is equal to or smaller than the threshold value, the blood pressure monitor 1 proceeds to step S161, and compares the features of the waveforms of the pulse wave signal PS1-1 obtained at the first time and the pulse wave signal PS1-2 obtained at the second time under the control of the moving direction estimation unit 123 to determine which pulse wave signal is closer to the condition corresponding to the reference position. For example, the maximum amplitudes AM1-1 and AM1-2 obtained in steps S102 and S105 are compared with each other, and a pulse wave signal having a greater maximum amplitude can be regarded as the pulse wave signal obtained at a position closer to the reference position.

In step S161, any determination method may be used. For example, the correlation value of the reference waveform and the pulse wave signal PS1-1 acquired in the processing at the first time may be compared with the correlation value of the reference waveform and the pulse wave signal PS1-2 acquired in the processing at the second time. Alternatively, the signal intensities may be simply compared.

Based on the comparison result in step S161, the blood pressure monitor 1 outputs information indicative of a direction in which to move (hereinafter, also referred to as a "correction direction") in step S162 under the control of the output unit 5, and causes the display 50 to display the information. For example, if it is determined that a better result is obtained in the measurement at the second time than at the first time, an arrow can be displayed so as to indicate the same direction as the direction of an actual movement after step S160. The direction of the actual movement can be determined, for example, by detecting the rotation direction with a sensor. As the instruction for movement in step S160, an arrow indicating an arbitrary direction may be displayed on the display 50, and the direction of the actual movement may be estimated at this direction. Since the diameter of the radial artery 91 of an adult is around 3.0 mm, an instruction may be provided to indicate that the adjustment of about several millimeters is preferable, in addition to the instruction of the direction.

Figure 17A:
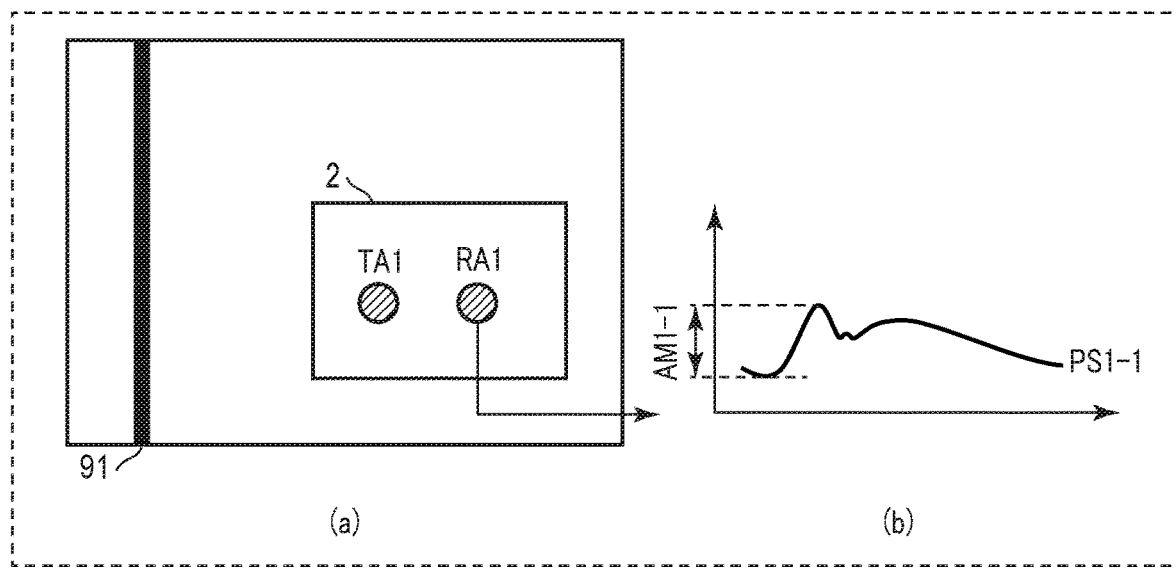
FIG. 17A is a schematic diagram illustrating an example of the relative positional relationship between an artery and an antenna, and a pulse wave signal obtained therefrom, which is assumed in the processing procedure illustrated in FIG. 16.
Figure 17B:
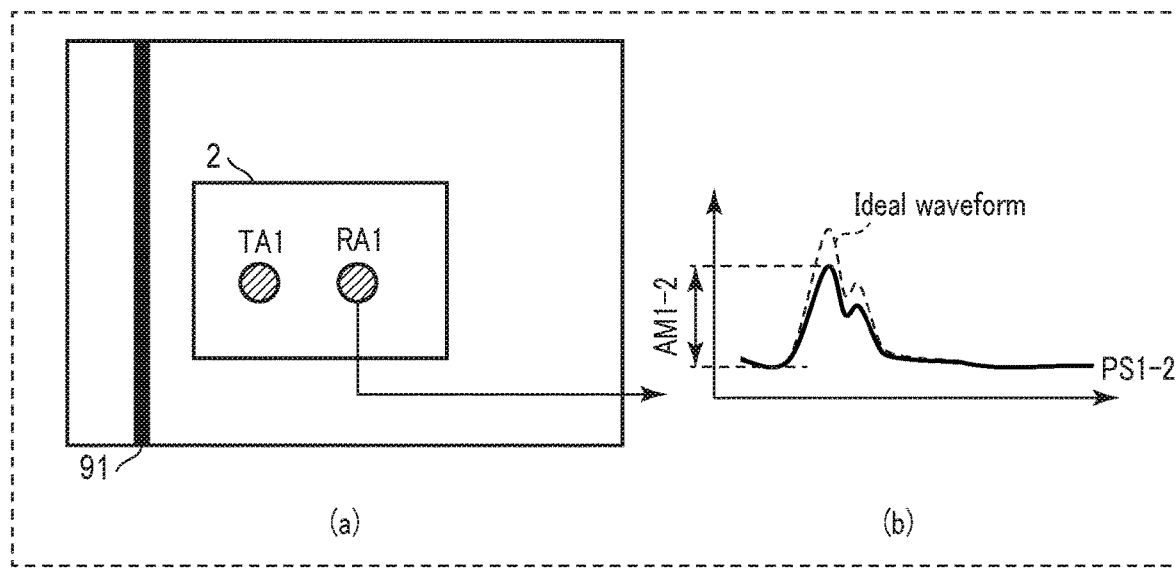
FIG. 17B is a schematic diagram illustrating another example of the relative positional relationship between an artery and an antenna, and a pulse wave signal obtained therefrom, which is assumed in the processing procedure illustrated in FIG. 16.
Figure 17C:
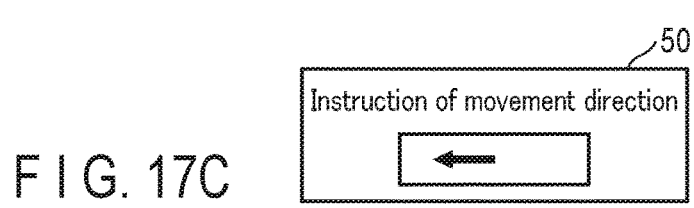
FIG. 17C is a schematic diagram illustrating a notification image displayed on a display.

FIGS. 17A and 17B explain the processing operation illustrated in FIG. 16, in which (a) shows the position of the antenna with respect to the radial artery 91, and (b) shows an example of the obtained pulse wave signal. FIG. 17C shows an example of a notification image displayed on the display 50.

For example, it is assumed that the pulse wave signal PS1-1 is acquired at the position shown in (a) of FIG. 17A in the measurement at the first time, and that the blood pressure monitor 1 is then rotated in the circumferential direction to move the wearing position to the position shown in (a) of FIG. 17B, and thereafter that the measurement at the second time is performed to acquire the pulse wave signal PS1-2.

In this case, for example, neither of the signal levels of the pulse wave signals satisfies the condition corresponding to the reference position; however, the pulse wave signal PS1-2 obtained at the second time has a larger amplitude. Therefore, as shown in FIG. 17C, the display 50 displays an arrow indicating that the blood pressure monitor 1 should be further moved (position adjustment) in the same direction as the moving direction from the position shown in (a) of FIG. 17A to the position shown in (a) of FIG. 17B.

The instruction of the direction to be adjusted may be provided in any other form such as blinking of light or voice. For example, a plurality of LEDs may be provided as the display 50, and the direction may be indicated by sequentially turning on the LEDs. When worn on the wrist 90, the display 50 of the wristwatch-type blood pressure monitor 1 is normally positioned on the back side surface of the wrist 90, while the sensor unit 2 is positioned on the palm-side surface 90a of the wrist 90. When the blood pressure monitor 1 is rotated around the wrist to adjust the position, the direction of the arrow shown on the display 50 corresponds to the movement direction of the sensor unit 2.

As described above, an arbitrary method can be used as a method of determining whether or not the condition corresponding to the reference position is satisfied. The operations of steps S104 to S106 may be the same as or different from those of steps S101 to S103.

Example 2-2

Figure 18:
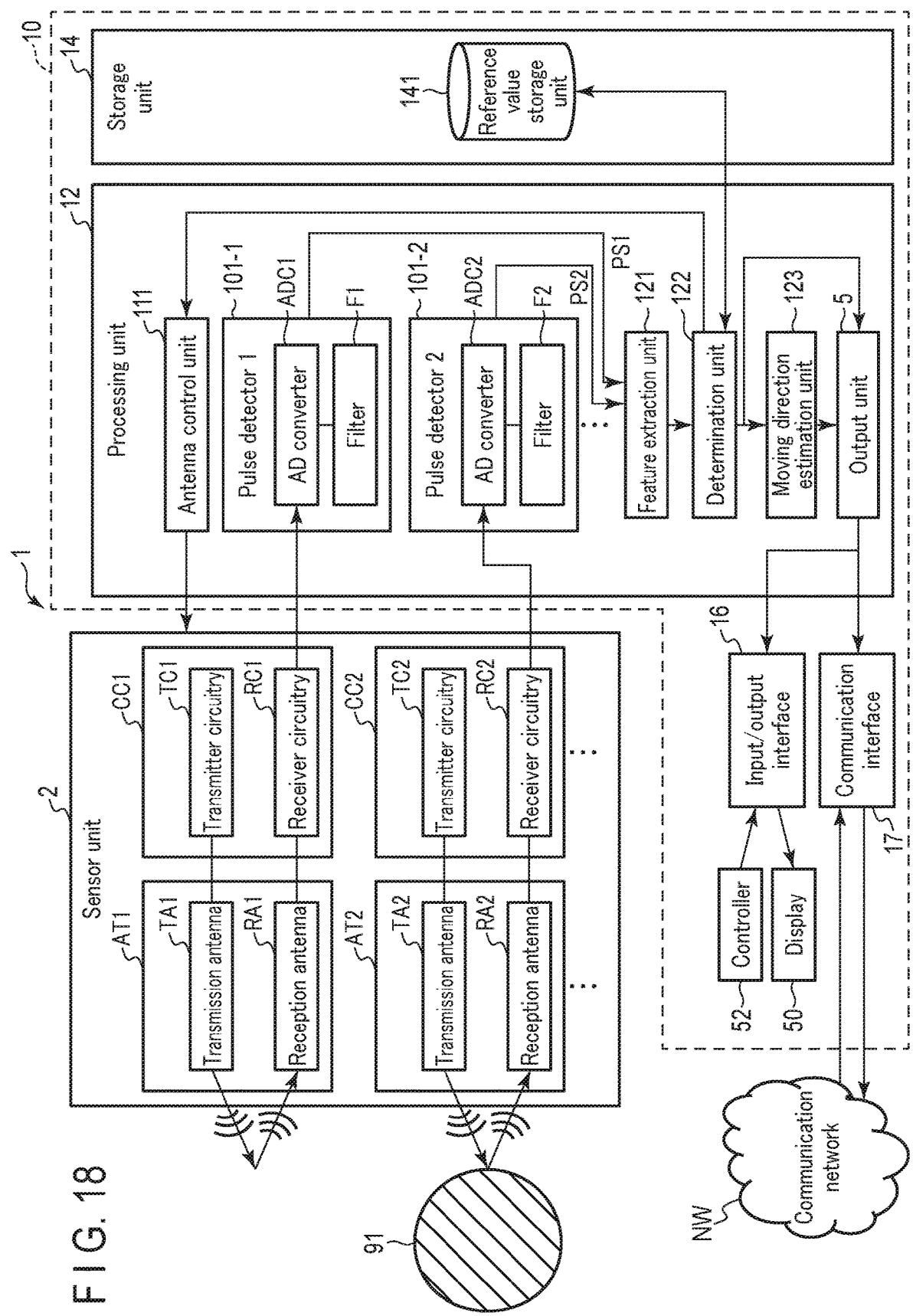
FIG. 18 is a block diagram illustrating an example of a functional configuration of the biological information measurement apparatus according to the embodiment of the present disclosure.

FIG. 18 is a block diagram illustrating another example of the functional configuration of the blood pressure monitor 1 according to the second embodiment. In FIG. 18, the same components as those in FIG. 12 and FIG. 15 are denoted by the same reference numerals, and a detailed description thereof will be omitted.

The blood pressure monitor 1 of FIG. 18 includes a plurality of antennas AT1, AT2, . . . , a plurality of control circuits CC1, CC2, . . . , a plurality of pulse detectors 101-1, 101-2, . . . , and an antenna control unit 111 as in FIG. 12, and further includes a moving direction estimation unit 123 as in FIG. 15.

Figure 19:
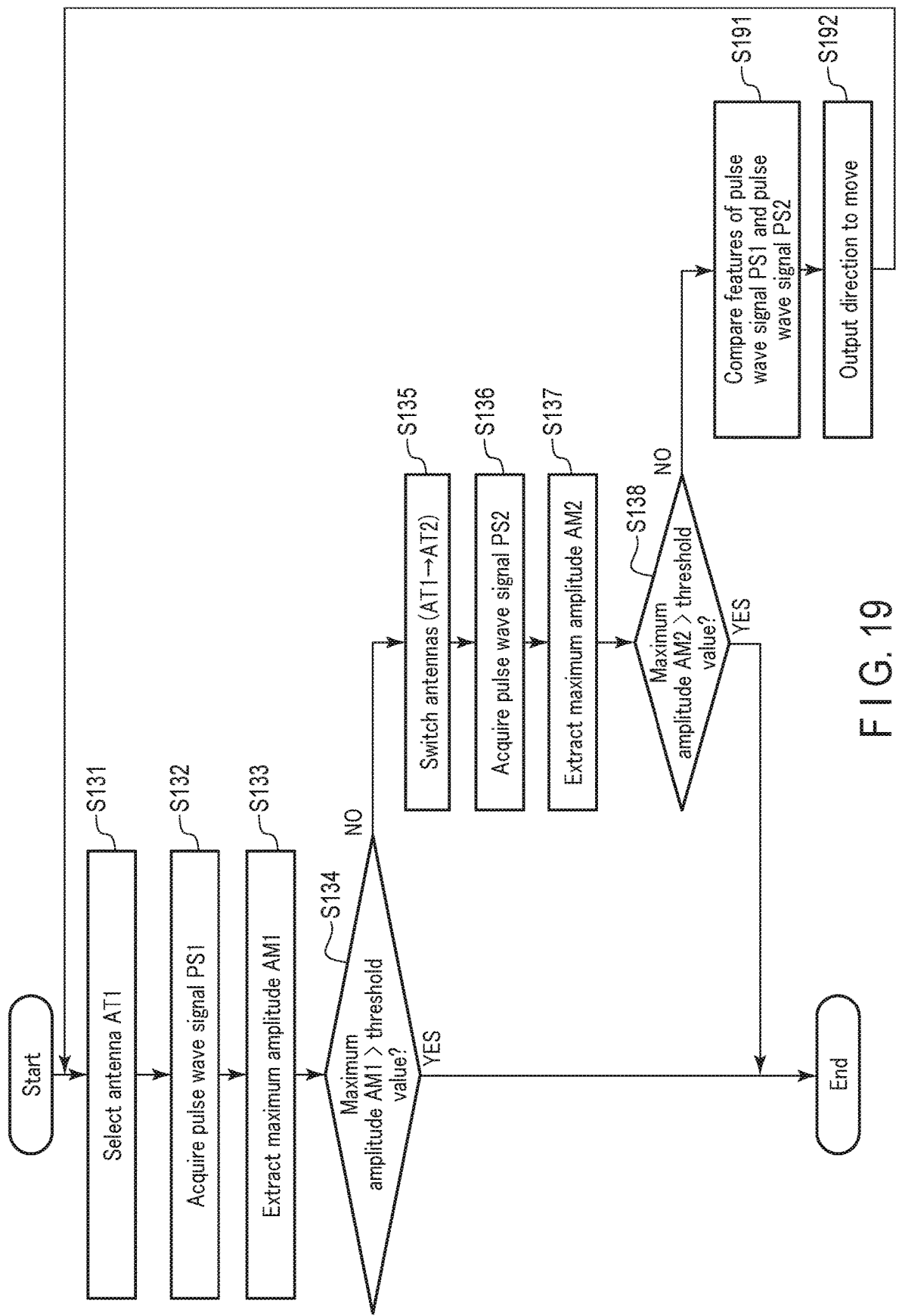
FIG. 19 is a flowchart illustrating an example of the processing procedure of the biological information measurement apparatus illustrated in FIG. 18.

FIG. 19 is a flowchart illustrating an example of the processing procedure of the blood pressure monitor 1 illustrated in FIG. 18. In FIG. 19, the same components as those in FIG. 13 are denoted by the same reference numerals, and a detailed description thereof will be omitted.

When the blood pressure monitor 1 receives a measurement start instruction signal input by the operation of the user from the controller 52, it selects the antenna AT1 in step S131, and executes a series of processing operations in steps S132 to S134 using the antenna AT1 first. For example, a pulse wave signal PS1 received using the antenna AT1 is acquired in step S132, and a maximum amplitude AM1 is extracted from the acquired pulse wave signal PS1 in step S133. In step S134, it is determined whether or not the maximum amplitude AM1 of the pulse wave signal PS1 satisfies a predetermined condition. In this example, the maximum amplitude AM1 is compared with the threshold value set in advance to determine whether the maximum amplitude AM1 is greater than the threshold value. If it is determined in step S134 that the maximum amplitude AM1 is greater than the threshold value, the process may end.

As a result of the determination, if it is determined that the maximum amplitude AM1 is equal to or smaller than the threshold value, the blood pressure monitor 1 proceeds to step S135. Next, the blood pressure monitor 1 switches the antenna AT1 to the antenna AT2 in step S135, and executes a series of pro operations through steps S136 to S138. For example, a pulse wave signal PS2 received using the antenna AT2 is acquired in step S136, and a maximum amplitude AM2 is extracted from the pulse wave signal PS2 in step S137. Then, in step S138, it is determined whether the maximum amplitude AM2 of the pulse wave signal PS2 satisfies a predetermined condition, in this example, whether the maximum amplitude AM2 is greater than the threshold value. If it is determined in step S138 that the maximum amplitude AM2 is greater than the threshold value, the process may end. If it is determined in step 138 that the maximum amplitude AM2 is equal to or smaller than the threshold value, the process proceeds to step S191.

In step S191, the blood pressure monitor 1 compares the features of the waveforms of the pulse wave signal PS1 and the pulse wave signal PS2 under the control of the moving direction estimation unit 123 to determine which pulse wave signal is closer to the condition corresponding to the reference position. For example, the maximum amplitudes AM1 and AM2 are compared with each other, and a pulse wave signal having a greater amplitude value can be regarded as the pulse wave signal obtained by an antenna closer to the reference position.

In step S191, any determination method may be used. For example, instead of comparing the maximum amplitudes, other features of the pulse wave signals, for example, correlation values with reference waveforms, may be compared, or peak intensities of the signals may be compared.

Based on the comparison result in step S191, the blood pressure monitor 1 outputs information indicative of a direction in which to move in step S192 under the control of the output unit 5, and causes the display 50 to display the information. For example, if it is determined that a better result is obtained in the measurement using the antenna AT2 than in the measurement using the antenna AT1, an arrow is displayed so as to indicate the same direction as the vector from the antenna AT1 to the antenna AT2.

Figure 20A:
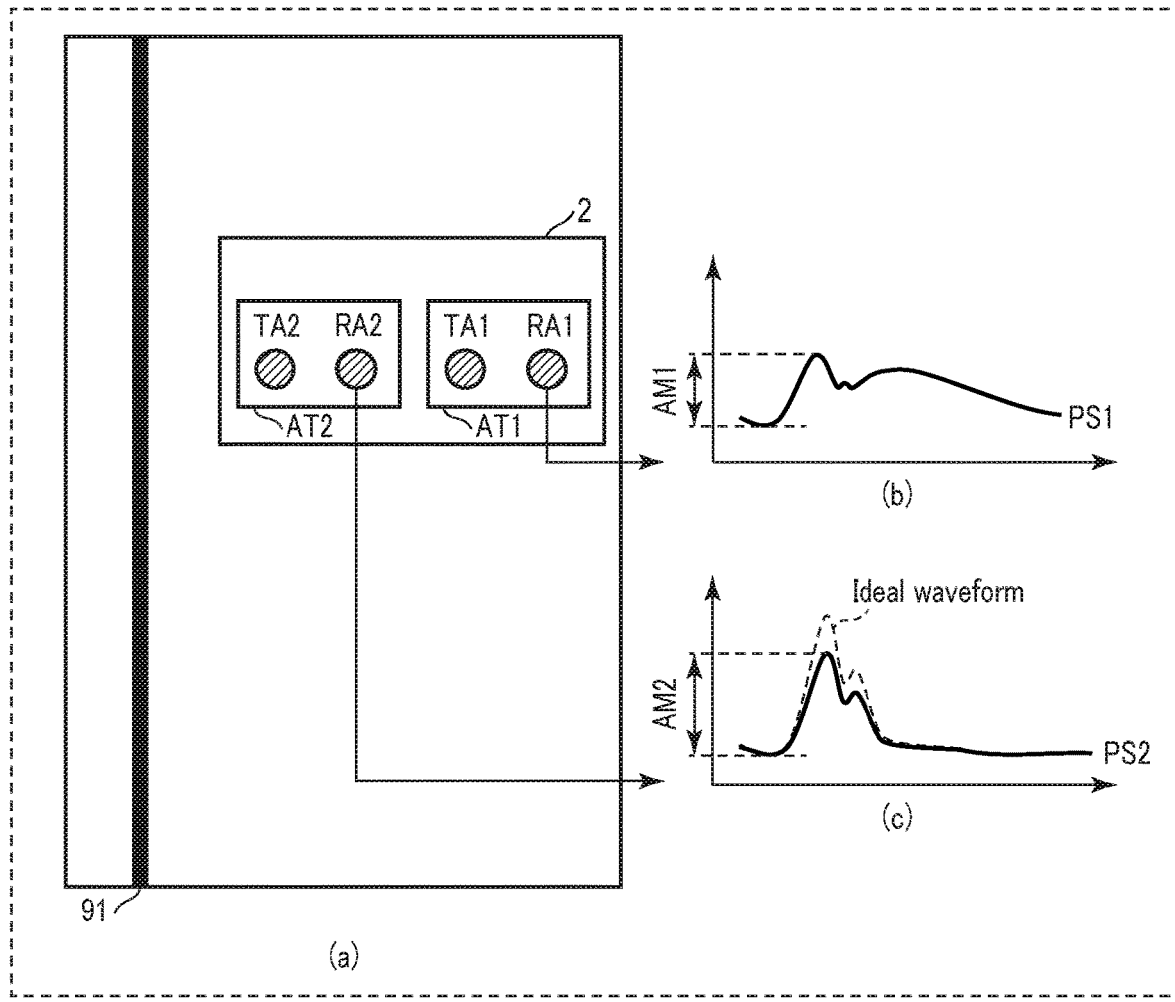
FIG. 20A is a schematic diagram illustrating an example of the relative positional relationship between an artery and an antenna, and a pulse wave signal obtained therefrom, which is assumed in the processing procedure illustrated in FIG. 19.
Figure 20B:
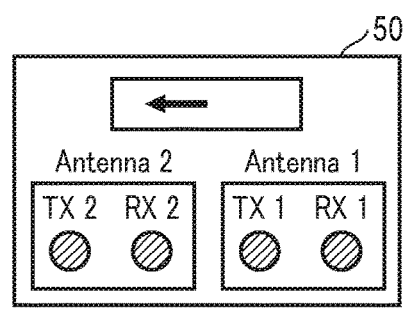
FIG. 20B is a schematic diagram illustrating a notification image displayed on a display.

FIG. 20A explains the processing operation illustrated in FIG. 19, in which (a) shows the positions of the antennas AT1 and AT2 with respect to the radial artery 91, and (b) and (c) show examples of pulse wave signals PS1 and PS2 obtained through the antennas AT1 and AT2, respectively. FIG. 20B shows an example of a notification image displayed on the display 50.

As shown in (a) of FIG. 20A, the sensor unit 2 includes two antennas AT1 and AT2. In the example shown in FIG. 20A, both the antenna AT1 and the antenna AT2 are positioned away from the radial artery 91. Therefore, in steps S134 and S138, it is determined that the maximum amplitude of the pulse wave signal is equal to or smaller than the threshold value. Therefore, the blood pressure monitor 1 shifts from step S138 to step S191 in FIG. 19, and compares the features of the pulse wave signals PS1 and PS2 in step S191.

For example, if it is determined in step S191 that the maximum amplitude AN2 of the pulse wave signal PS2 obtained by using the antenna AT2 is greater, the blood pressure monitor 1 outputs the determination (comparison) result of step S191 from the output unit 5 in step S192, and displays an arrow indicating that further movement should be made in the same direction as the vector from the antenna AT1 to the antenna AT2 on the display 50 as shown in FIG. 20B.

As described above, an arbitrary method can be used as a method of determining whether or not the condition corresponding to the reference position is satisfied. The operations of steps S136 to S138 may be the same as or different from those of steps S132 to S134.

In Example 2-2, the operation of the blood pressure monitor 1 including two pairs of antennas has been described; however, the correction direction may be estimated based on more measurement results obtained by switching the antennas in the blood pressure monitor 1 including more antennas. For example, it is possible to derive the direction of a vector directed from the antenna corresponding to the pulse wave signal with the worst result (for example, the smallest amplitude), among all the pulse wave signals obtained through three or more pairs of antennas, to the antenna corresponding to the pulse wave signal with the best result (for example, the greatest amplitude). Alternatively, the optimum position (reference position) may be estimated by plotting the amplitude values of all pulse wave signals obtained through three or more pairs of antennas based on the relative positions of the antennas and obtaining a regression formula. An example of an estimation method using a regression formula will be described in detail later.

As described above, in step S135, a series of operations may be repeated by switching only the antenna element used for reception or only the antenna element used for transmission. For example, in a series of operations at a first time (steps S132 to S134), transmission and reception of radio waves may be performed using the first transmission antenna element TA1 and the first reception antenna element RA1, and in a series of operations at a second time (steps S136 to S138), transmission and reception of radio waves may be performed using the first transmission antenna element TA1 and the second reception antenna element RA2. Thus, the number of transmission antenna elements and the number of reception antenna elements need not be the same.

(Effects and Advantages of Second Embodiment)

As described above in detail, in the second embodiment, the features extracted from pulse wave signals obtained by a plurality of measurements are compared with each other to calculate and output a direction in which the blood pressure monitor 1 is to be moved so as to be set at an appropriate setting position. Therefore, it is possible to determine whether or not the setting position of the blood pressure monitor 1 is appropriate with a simple and inexpensive configuration, and without separately providing a position detection sensor such as an accelerometer; and if the setting position is not appropriate, it is further possible to obtain an index as to the direction in which the blood pressure monitor 1 should be moved based on a plurality of measurement results.

In addition, the user checks the adjustment direction by, for example, an arrow displayed on the display 50, and then rotates the blood pressure monitor in the circumferential direction of the wrist to search for a position suitable for measurement. Therefore, the blood pressure monitor 1 can be efficiently aligned with respect to the wrist, and the convenience of the user and the robustness of sensor setting are greatly improved.

Third Embodiment

Example 3-1

FIG. 21 is a flowchart illustrating an example of a processing procedure of a blood pressure monitor 1 according to the third embodiment of the present invention. This processing procedure is performed by the blood pressure monitor 1 illustrated in FIG. 18, for example, including a plurality of antennas AT1, AT2, . . . , and the moving direction estimation unit 123 estimates the required amount of movement (hereinafter, also referred to as a "correction amount") in addition to the direction in which to move. In FIG. 21, the same components as those in FIG. 13 are denoted by the same reference numerals, and a detailed description thereof will be omitted.

When the blood pressure monitor 1 receives a measurement start instruction signal input by the operation of the user from the controller 52, it selects the antenna AT1 in step S131, and executes a series of processing operations in steps S132 to S134 using the antenna AT1 first. For example, a pulse wave signal PS1 received using the antenna AT1 is acquired in step S132, and a maximum amplitude AM1 is extracted from the acquired pulse wave signal PS1 in step S133. In step S134, it is determined whether the maximum amplitude AM1 of the pulse wave signal PS1 satisfies a predetermined condition. In this example, the maximum amplitude AM1 is compared with a threshold value set in advance to determine whether the maximum amplitude AM1 is greater than the threshold value. If it is determined in step S134 that the maximum amplitude AM1 is greater than the threshold value, the process may end.

If it is determined in step S134 that the maximum amplitude AM1 is equal to or smaller than the threshold value, the blood pressure monitor 1 proceeds to step S135, switches the antenna AT1 to antenna to AT2 in step S135, and executes a series of processing operations in steps S136 to S138. For example, a pulse wave signal PS2 is acquired in step S136, and a maximum amplitude AM2 is extracted from the pulse wave signal PS2 in step S137. In step S138, it is determined whether the maximum amplitude AM2 of the pulse wave signal PS2 satisfies a predetermined condition. In this example, the maximum magnitude AM2 is compared with the threshold value to determine whether the maximum magnitude AM2 exceeds the threshold value. If it is determined in step S138 that the maximum amplitude AM2 is greater than the threshold value, the process may end. If it is determined in step 138 that the maximum magnitude AM2 is equal to or smaller than the threshold value, the process proceeds to step S211.

Figure 22A:
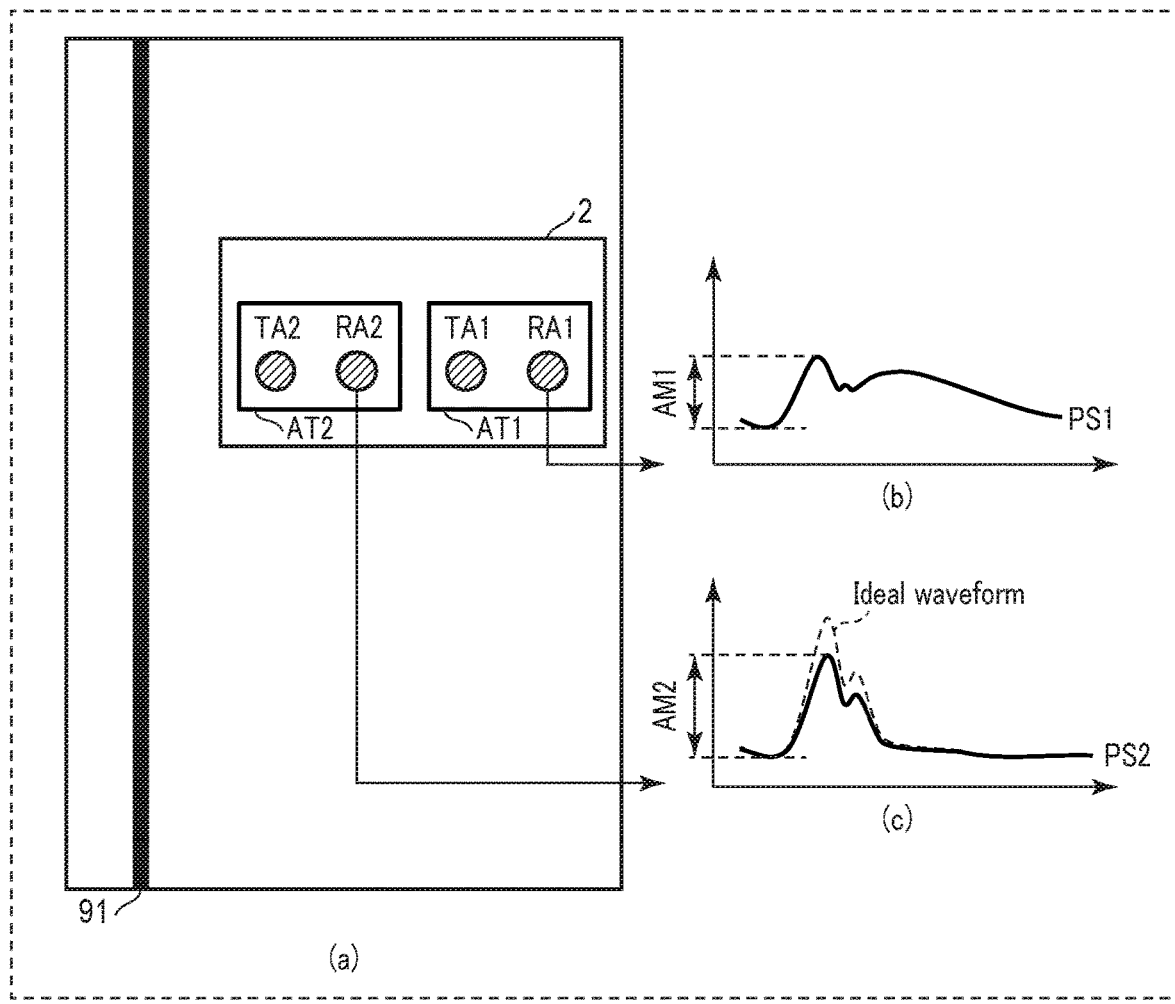
FIG. 22A is a schematic diagram illustrating an example of the relative positional relationship between an artery and an antenna, and a pulse wave signal obtained therefrom, which is assumed in the processing procedure illustrated in FIG. 21.
Figure 22B:
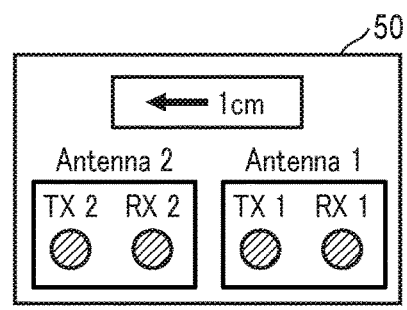
FIG. 22B is a schematic diagram illustrating a notification image displayed on a display.

FIG. 22A explains the processing operation illustrated in FIG. 21, in which (a) shows the positions of the antennas AT1 and AT2 with respect to the radial artery 91, and (b) and (c) show examples of pulse wave signals PS1 and PS2 obtained through the antennas AT1 and AT2, respectively. FIG. 22B shows an example of a notification image displayed on the display 50.

As shown in (a) of FIG. 22A, the sensor unit 2 includes two antennas AT1 and AT2. In the example shown in (a) of FIG. 22A, both the antenna AT1 and the antenna AT2 are positioned away from the radial artery 91. Therefore, in steps S134 and S138, it is determined that the pulse wave signal does not satisfy the predetermined condition. Therefore, the blood pressure monitor 1 shifts from step S138 to step S211 in FIG. 21.

In step S211, under the control of the moving direction estimation unit 123, the blood pressure monitor 1 estimates a direction and a required amount of movement (a correction direction and a correction amount) by comparing the features of the waveforms of the pulse wave signal PS1 obtained using the antenna AT1 and of the pulse wave signal PS2 obtained using the antenna AT2.

Figure 23:
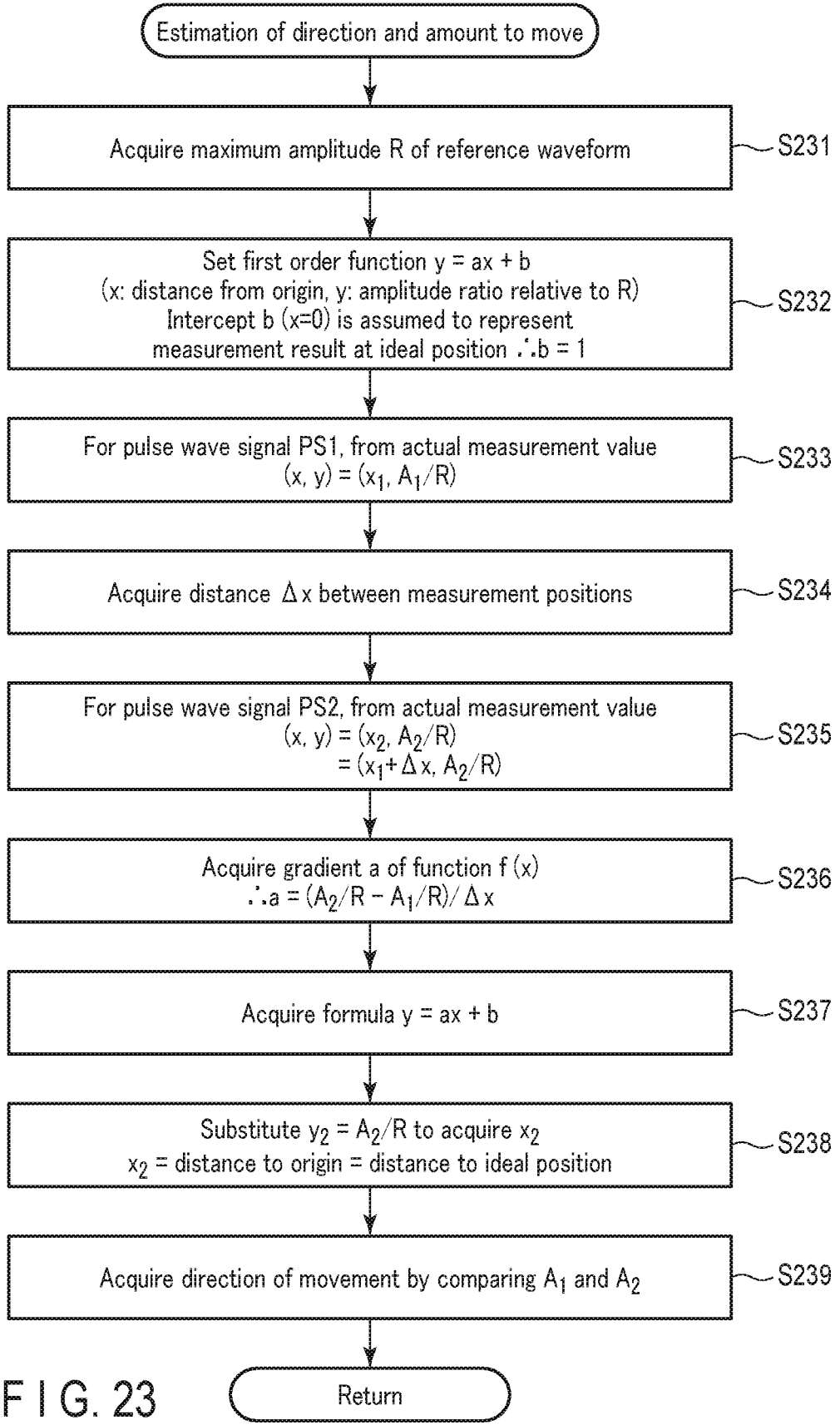
FIG. 23 is a flowchart illustrating an example of a procedure of estimating a direction and an amount to be moved in the processing illustrated in FIG. 21.
Figure 24A:
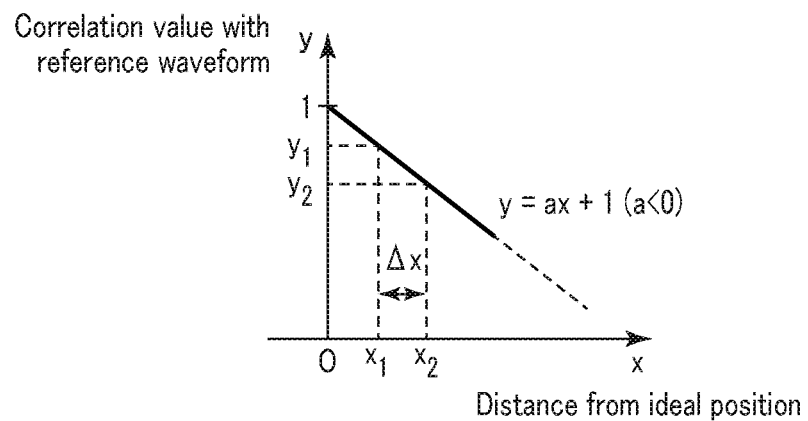
FIG. 24A is a diagram illustrating an example of a regression line in the estimating procedure illustrated in FIG. 23.
Figure 24B:
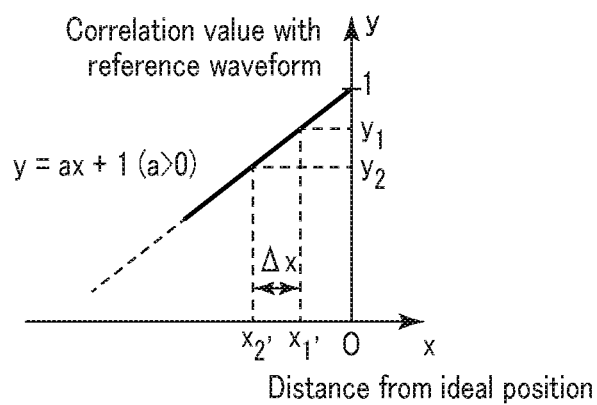
FIG. 24B is a diagram illustrating another example of the regression line in the estimating procedure illustrated in FIG. 23.

FIG. 23 is a flowchart illustrating an example of procedure and processing contents for calculating (estimating) a direction and an amount to move by using linear approximation, which can be adopted in step S211. FIGS. 24A and 24B show outlines of the linear approximation used in FIG. 23.

In FIGS. 24A and 24B, a formula of a first order function $f(x)=y=ax+b$ is defined on the assumption that the correlation value between the waveform of the obtained pulse wave signal and the reference waveform changes linearly according to the distance from the reference position (ideal position). That is, a first order approximation formula (regression formula) is derived based on the distance between the antenna AT1 and the antenna AT2, and on the ratio of the amplitudes of the pulse wave signals and the reference waveform obtained using the antennas, the distance to the reference position at which the reference waveform is expected to be obtained being estimated based on the obtained approximation formula.

To be more specific, in FIGS. 24A and 24B, a first order function $y=ax+b$ is defined, where the reference position (ideal position) is represented as $x=0$, the x-axis represents the distance from the reference position, and the y-axis represents the correlation value with the reference waveform (as the value is closer to 1, the correlation with the reference waveform is higher) (where $a<0$ when $0\leq x$, and $a>0$ when $x<0$). Thus, the function $y=f(x)$ has the maximum value b on the y-axis ($x=0$). Since the intercept b represents the correlation value between the waveform of the pulse wave signal acquired at the reference position and the reference waveform, the intercept b can be approximately regarded as 1. Depending on the positional relationship between the radial artery 91 and the sensor unit 2 (for example, which of the antenna AT1 and the antenna AT2 is closer to the radial artery 91), the x coordinate takes a positive or negative value, as shown in FIG. 24A or 24B.

An example of a method of calculating the correction direction and the correction amount will be described in more detail with reference to FIG. 23.

In step S231, the moving direction estimation unit 123 acquires a maximum amplitude R of the reference waveform from the reference value storage unit 141 or the like. For example, R may be calculated from past measurement results that are actually obtained, or may be an arbitrarily set value.

In step S232, the moving direction estimation unit 123 sets a first order function $f(x)=y=ax+b$. Since the intercept b represents the ratio between the maximum amplitude of the pulse wave signal obtained at the ideal position and the maximum amplitude R of the reference waveform, the intercept b can be approximately 1, and the first order function is expressed as $y=ax+1$.

In step S233, the moving direction estimation unit 123 extracts a maximum amplitudes $A_1$ as a feature of the waveform of the pulse wave signal PS1 acquired using the antenna AT1, and obtains an amplitude ratio $A_1/R$ with respect to the maximum amplitude R of the reference waveform. The data obtained for the antenna AT1 is expressed as $(x,y)=(x_1, y_1)=(x_1, A_1/R)$.

In step S234, the moving direction estimation unit 123 acquires a distance $\Delta x$ between the reception antenna element RA1 of the antenna AT1 and the reception antenna element RA2 of the antenna AT2 from a storing unit (not shown) or the like.

In step S235, the moving direction estimation unit 123 extracts a maximum amplitudes $A_2$ as a feature of the waveform of the pulse wave signal PS2 acquired using the antenna AT2, and obtains the amplitude ratio $A_2/R$. The data obtained from the pulse wave signal PS2 is expressed as $(x,y)=(x_2, y_2)=(x_1\Delta x, A_2/R)$.

In step S236, the moving direction estimation unit 123 acquires the gradient a of the first order function f(x) via the following formula:

$$a=(A_2/R-A_1/R)/\Delta x.$$

Since a and b are calculated as described above, the moving direction estimation unit 123 obtains the formula $y=ax+b$ of the first order function f(x) in step S237.

In step S238, the moving direction estimation unit 123 substitutes the ratio $y_2=A_2/R$ of the amplitude of the antenna AT2 into the formula $y=ax+b$ to obtain the x coordinate ($x_2$). This is the distance from the reception antenna element RA2 of the antenna AT2 to the ideal position (the amount to move, the correction amount).

In step S239, the moving direction estimation unit 123 acquires a direction in which to move (correction direction). For example, the method described above with respect to Example 2-2 can be adopted. Thereafter, the process returns to step S212 in FIG. 21.

In step S212, information indicative of the calculated (estimated) correction direction and the amount of correction is output by the output unit 5 and displayed on the display 50, for example, as shown in FIG. 22B.

Example 3-2

Figure 25:
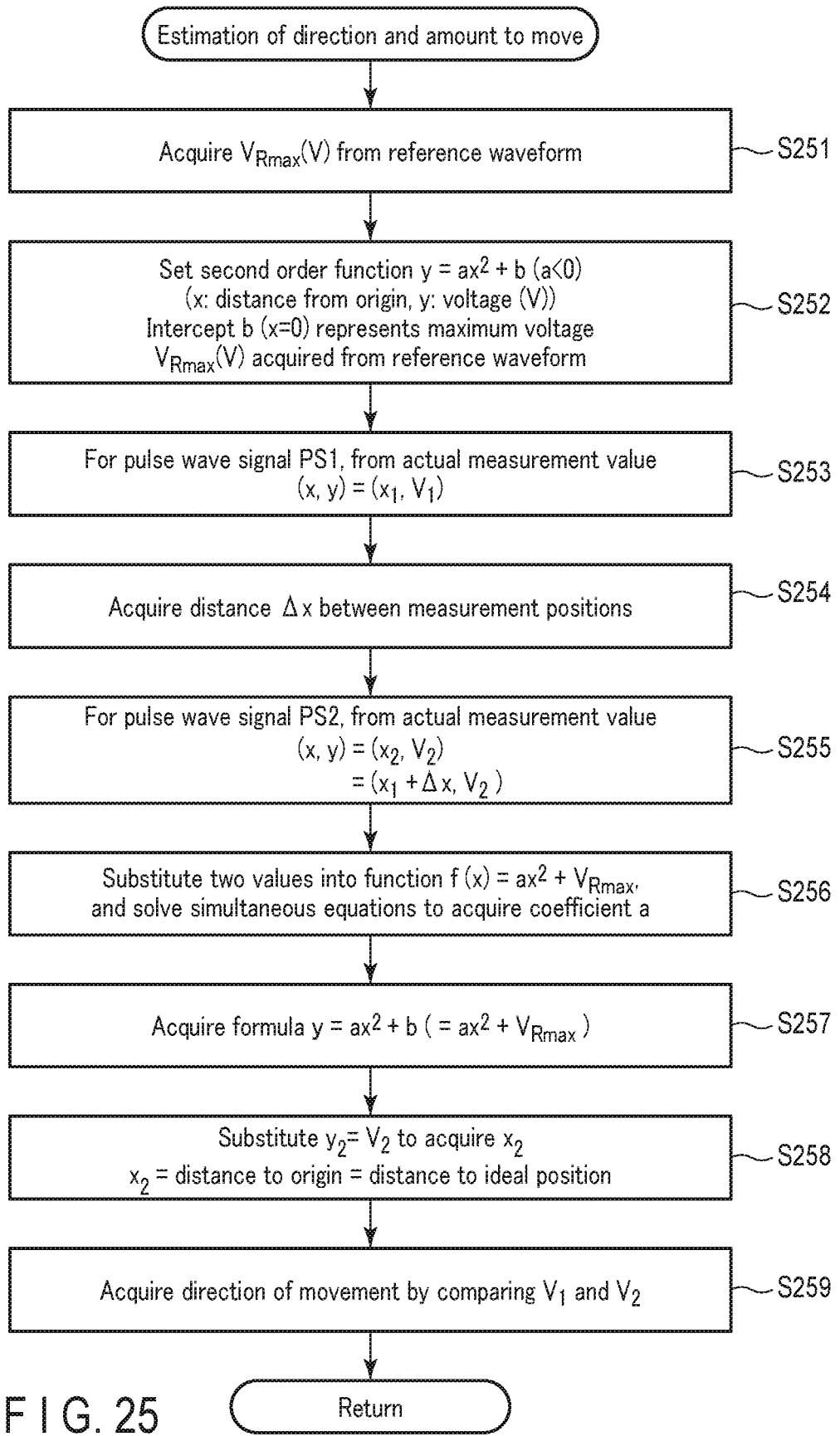
FIG. 25 is a flowchart illustrating another example of a procedure of estimating a direction and an amount to be moved in the processing illustrated in FIG. 21.
Figure 26A:
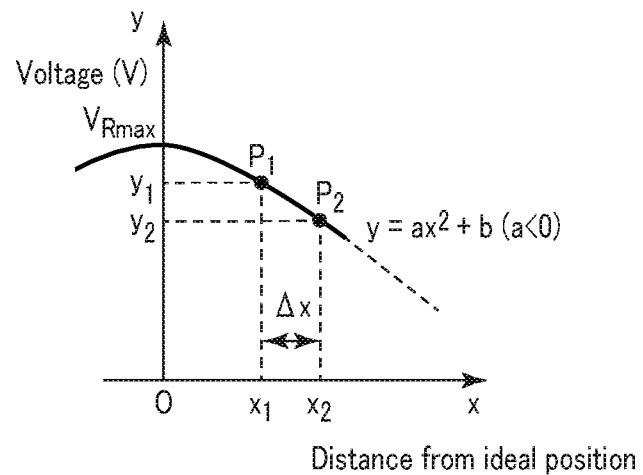
FIG. 26A is a diagram illustrating an example of a regression curve in the estimation procedure illustrated in FIG. 25.
Figure 26B:
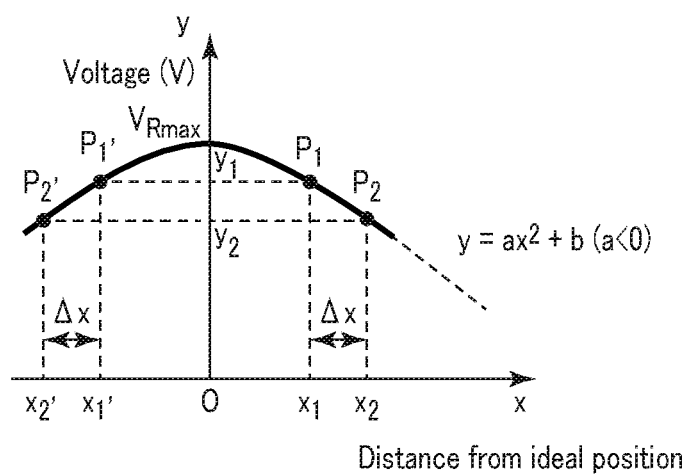

FIG. 25 is a flowchart illustrating another example of a predetermined procedure and processing contents for calculating (estimating) a direction and an amount to move by using nonlinear approximation, which can be adopted in step S211. FIGS. 26A and 26B show outlines of the nonlinear approximation used in FIG. 25.

In FIG. 26A and FIG. 26B, a second order function $f(x)=y=ax^2+b$ is defined on the assumption that the amplitude value (peak voltage (V) in this example) of the obtained pulse wave signal changes in a curved manner according to the distance from the reference position (ideal position). That is, a second order approximation formula (regression formula) is derived based on the distance between the antenna AT1 and the antenna AT2 and the amplitude values of the pulse wave signals obtained using the antennas, and the distance to the reference position at which the reference waveform is expected to be obtained is estimated based on the obtained approximation formula.

To be more specific, in FIGS. 26A and 26B, a simple second order function $f(x)=y=ax^2+b$ (a<0) is defined, where the reference position (ideal position) is represented as x=0, the x-axis represents the distance from the reference position, and the y-axis represents the amplitude value (voltage (V)). Thus, the function y=f(x) is represented as an upwardly convex curve having a vertex on the y-axis (x=0). Since the intercept h represents the amplitude value of the pulse wave signal acquired at the reference position, the intercept b can be acquired as the amplitude value (V) of the reference waveform stored in the reference value storage unit 141 or the like. Depending on the positional relationship between the radial artery 91 and the sensor unit 2 (for example, which of the antenna AT1 and the antenna AT2 is closer to the radial artery 91), the x coordinate takes a positive or negative value, as shown in FIG. 26B.

An example of a method of calculating the correction direction and the correction amount will be described in more detail with reference to FIG. 25.

In step S251, the moving direction estimation unit 123 acquires a peak voltage $V_{Rmax}(V)$ of the reference waveform from the reference value storage unit 141 or the like. For example, $V_{Rmax}(V)$ may be calculated from past measurement results that are actually obtained, or may be an arbitrarily set value.

In step S252, the moving direction estimation unit 123 sets a second order function $f(x)=y=ax^2+b$ (a<0). Since the intercept b represents the peak voltage (V) of the pulse wave signal obtained at the ideal position, the second order function is expressed as $y=ax^2+V_{Rmax}$.

In step S253, the moving direction estimation unit 123 obtains a peak voltage $V_1(V)$ of the pulse wave signal PS1 acquired using the antenna AT1. The data obtained for the antenna AT1 is expressed as $(x,y)=(x_1, y_1)=(x_1,V_1)$.

In step S254, the moving direction estimation unit 123 acquires a distance $\Delta x$ between the reception antenna element RA1 of the antenna AT1 and the reception antenna element RA2 of the antenna AT2 from a storing unit (not shown) or the like.

In step S255, the moving direction estimation unit 123 obtains a peak voltage $V_2(V)$ of the pulse wave signal PS2 acquired using the antenna AT2. The data obtained for the antenna AT2 is expressed as $(x,y)=(x_2, y_2)=(x_1+\Delta x,V_2)$.

In step S256, the moving direction estimation unit 123 substitutes the aforementioned two data items obtained for the pulse wave signals PS1 and PS2 into the second order function f(x), and solves the following two simultaneous equations to obtain the coefficient a (and an unknown $x_1$).

$$V_1=ax_1^2+V_{Rmax}$$

$$V_2=ax_2^2V_{Rmax}a(x_1+\Delta x)^2+V_{Rmax}$$

Since a and b are calculated as described above, in step S257, the moving direction estimation unit 123 obtains the formula $y=ax^2+b$ of the second order function f(x).

In step S258, the moving direction estimation unit 123 substitutes the peak voltage $V_2$ obtained for the antenna AT2 into the formula $y=ax^2+b$ to obtain the x coordinate ($x_2$). This is the distance from the reception antenna element RA2 of the antenna AT2 to the ideal position (the amount to move, the correction amount). More simply, $x_2$ may be obtained as $x_2=x_1+\Delta x$ from $x_1$ calculated by solving the simultaneous equations in step S256.

In step S259, the moving direction estimation unit 123 acquires a direction in which to move (correction direction). For example, the method described with respect to Example 2-2 can be adopted. Thereafter, the process returns to step S212 in FIG. 21. In FIG. 25, the second order function is used as the nonlinear approximation, but an arbitrary n-th order curve, such as a third order curve or a fourth order curve, can be used.

As shown in FIG. 26B, in the second order regression, two x-coordinates may exist for one voltage value. This prevents the correct correction direction and correction amount from being calculated, for example, when two pairs of antennas AT1 and AT2 are arranged across the reference position (radial artery 91). For example, even though the positions should actually correspond to points $P_1$ and $P_2'$ in FIG. 26B, they may be calculated as corresponding to points $P_1$ and $P_2$. However, it is considered that such a problem can be minimized by appropriately setting the distance between the antennas AT1 and AT2. For example, when two pairs of antennas are arranged so as to straddle the y-axis, at least one of the antennas satisfies the condition corresponding to the ideal position, and it is likely that measurement can be performed immediately. In addition, since it is assumed that the user performs alignment while slowly moving the blood pressure monitor 1, quick approximation by a simple process is preferable to accurate calculation in many cases.

Examples 3-1 and 3-2 have been described with respect to the operation of the blood pressure monitor 1 including two pairs of antennas, in which the relative distance between the antennas is known. However, for example, the methods of Examples 3-1 and 3-2 can be applied to a case where measurement is performed a plurality of times at different positions by the user moving the blood pressure monitor 1 as described in Example 2-1, as long as the distance between two points (corresponding to $\Delta x$) is known. In order to obtain the distance between the two points, for example, the strap of the blood pressure monitor 1 may be provided with a scale of 1 mm units, and the user may be instructed to move the strap in the movement direction and the movement amount between the measurement at the first time and the measurement at the second time. Since the manual operation of the user is added, the calculation accuracy of the correction amount decreases. However, high accuracy is not required for the purpose of easily and quickly providing a rough index at the time of alignment. Furthermore, it is conceivable for movement distance to be detected by various sensors. For example, an acceleration sensor, an ultrasonic sensor, a photoelectric sensor, a Doppler sensor, or a frequency modulated continuous wave (FMCW) radar may be used. Further, the antenna in the pulse sensor may be used as a radio wave sensor as it is.

As described above, an arbitrary method can be used as a method of determining whether or not the condition corresponding to the reference position is satisfied. The operations of steps S136 to S138 may be the same as or different from those of steps S132 to S134. Furthermore, as described above, in step S135, a series of operations may be repeated by switching only the antenna element used for reception or only the antenna element used for transmission.

(Effects and Advantages of Third Embodiment)

As described above in detail, in the third embodiment, the direction and amount of movement are calculated and output based on the features extracted from the pulse wave signals obtained by a plurality of measurements. Therefore, it is possible to determine whether or not the setting position of the blood pressure monitor 1 is appropriate with a simple and inexpensive configuration and without separately providing a complicated evaluation device; and possible, where the setting position is not appropriate, to obtain an index as to the direction and degree the blood pressure monitor 1 should be moved based on a plurality of measurement results.

In addition, the user checks the adjustment direction, for example, indicated by an arrow displayed on the display 50 and the estimated distance to the reference position, and then rotates the blood pressure monitor 1 in the circumferential direction of the wrist to search for a position suitable for measurement. Therefore, the setting position of the blood pressure monitor 1 with respect to the wrist can be more efficiently aligned, and the convenience of the user and the robustness of sensor setting are greatly improved. Furthermore, even if the accurate position of the radial artery 91 is not known, if at least the distance between the two points at which the pulse wave signals are acquired is known, the amount to move can be estimated by an approximate calculation using a relatively simple function. Thus, the calculation processing can be incorporated without imposing an excessive load on the processor. In addition, the user can ascertain a rough position of the radial artery 91 of the user, and the facilitation of subsequent attachment can be expected.

Modification (1) Example Including Antennas Arranged in Matrix

FIG. 27 shows a part of a functional configuration of a blood pressure monitor 1 including a sensor unit 2 in which a plurality of antennas are arranged in a matrix, and a relative positional relationship between a radial artery 91 and the antennas.

In FIG. 27, six pairs of antennas AT1, AT2, . . . , AT6 are arranged in a matrix in the sensor unit 2. The reflected waves received using the antennas AT1, AT2, . . . , AT6 are sent to the receiver circuitry RC1, RC2, . . . , RC6, respectively, where waveform signals are generated. The waveform signals are subjected to AD conversion, filtering, and the like by the pulse detectors 101-1, 101-2, . . . , 101-6, and then input to the feature extraction unit 121 as pulse wave signals. The processes for the respective reflected waves may be performed simultaneously or sequentially. In addition, after the measurement of the pulse wave and the determination of whether or not the condition corresponding to the reference position is satisfied are performed using one antenna, the process may proceed to the measurement and determination operation using the next antenna. Alternatively, the process may proceed to the determination operation after the pulse wave signals are acquired for all the antennas.

When a pulse wave signal satisfying the condition is confirmed for at least one antenna, measurement of biological information can be started using any one or more antennas among the antennas satisfying the conditions. At this time, a message indicating that the setting position of the blood pressure monitor 1 is appropriate may be output to the display 50 to notify the user, or information indicative of which antenna is used for measurement (for example, the position or identification number of the antenna) may be output to the display 50 or another external device.

On the other hand, when no pulse wave signal that satisfies the condition is acquired for any of the antennas, it is possible to determine the antenna for which the best result is obtained and the antenna for which the worst result is obtained, and to estimate and output the direction in which to move based on the determination result. Accordingly, it is possible to present movement adjustment to a more suitable setting position not only in the direction orthogonal to the running direction of the artery but also in the direction parallel tb the artery, so that the subsequent measurement becomes more reliable.

Also in the modification shown in FIG. 27, by combining the above-described embodiments and examples, it is possible to calculate and notify the correction amount in addition to the correction direction. Further, as described above, in the comparison with the condition corresponding to the reference position, not only the maximum amplitude but also various features of the pulse wave signal can be used. The arrangement of the antennas shown in FIG. 27 is a mere example, and the above-described method can be applied to a modification in which an arbitrary number of antennas are arranged in an arbitrary pattern.

(2) Example of System Including Blood Pressure Monitor 1

Figure 28:
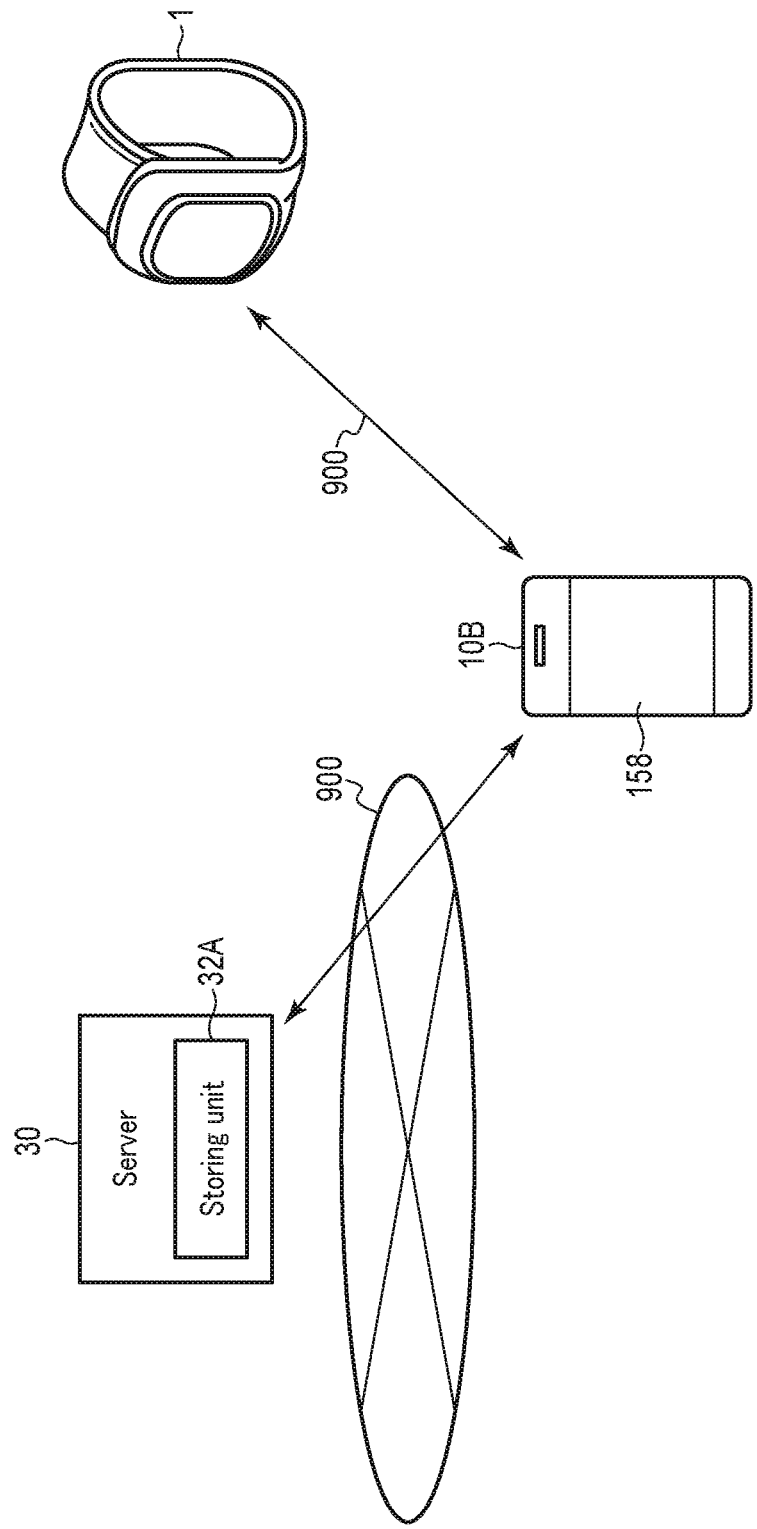
FIG. 28 is a schematic diagram of an example of a system including the blood pressure monitor illustrated in FIG. 3.

FIG. 28 is a diagram illustrating an example of a schematic configuration of a biological information management system including the blood pressure monitor 1 of the first to third embodiments described above. The blood pressure monitor 1 communicates with a server 30 or a portable terminal 10B, which is an external information processing apparatus, via a network 900. In the system of FIG. 28, the blood pressure monitor 1 communicates with the portable terminal 10B via a wireless interface employing a low-power wireless data transmission standard, such as a wireless LAN or Bluetooth (registered trademark), and the portable terminal 10B communicates with the server 30 via the Internet.

With such a configuration, for example, it is possible to determine, in the blood pressure monitor 1, the wearing position of the blood pressure monitor 1 with respect to the measurement ite, transfer the determination result from the blood pressure monitor 1 to the portable terminal 10B, and display the determination result on the display 158. As another example, a waveform signal or a pulse wave signal may be transmitted from the blood pressure monitor 1 to the portable terminal 10B, a determination regarding the attachment position of the blood pressure monitor 1 may be performed in the portable terminal 10B, and display information for adjusting the attachment position of the blood pressure monitor 1 may be displayed on the display 158 of the portable terminal 10B based on the determination result.

In the manner described above, the processing load in the blood pressure monitor 1 can be reduced, and the display information can be displayed on the display 158 of the portable terminal 10B having a larger size than the display device of the blood pressure monitor 1.

In addition, if the determination result of the attached state at the time of measurement is transmitted to the server 30 in association with the measurement data of the blood pressure, it is possible to determine the reliability whet evaluating the measurement data of the blood pressure in the server 30.

Therefore, a part or all of the processing described above as being executed by the processing unit 12 of the blood pressure monitor 1 may be executed by the processor of the portable terminal 10B by a program such as a mobile application operating on they portable terminal 10B.

(3) Further, in addition to the acquired pulse waves, the calculated blood pressure value, and the like, a message indicating whether the setting position of the blood pressure monitor 1 is appropriate or inappropriate may be created and output by the output unit 5 of the blood pressure monitor 1, and may be displayed on the display 50 of the blood pressure monitor 1 or transmitted to the portable terminal 10B and displayed on the display 158. Accordingly, the user can visually recognize a clearer display on a larger screen through an application program or the like that is operating on the portable terminal 10B. Furthermore, the message may be displayed on both the display 50 of the blood pressure monitor 1 and the display 158.

(4) In the above embodiments, the case where the pulse wave is measured at the radial artery 91 of the wrist has been described as an example; however, the pulse wave may be measured in other parts such as an upper arm, an ankle, a thigh, and a trunk.

(5) In addition, as each of the threshold values used in the above-described processing, a fixed value set in advance as an initial value may be used, or the threshold value may be automatically calculated from an average value when the pulse wave is normally acquired.

(6) The antenna pair in each of the embodiments described above may be replaced with a transmission/reception antenna. Therefore, the term "antenna" includes not only an antenna pair including a transmission antenna and a reception antenna, but also a transmission/reception antenna.

(7) If the polarity of the signal changes, the above detailed conditions can be reversed. Therefore, the detailed determination conditions and the regression formula described above can be variously modified according to the circuit design, the operating environment, and the like, and are no limited to the embodiments described above.

Although the embodiments of the present invention have been described in detail in the foregoing, the description is merely an example of the present invention in all of its aspects. Various improvements and modifications can be made without departing from the scope of the present invention. The following modifications can be made for example. In the following, the same reference numerals are used for the same constituent elements of the foregoing embodiment, and redundant descriptions are omitted as appropriate. The following modifications can be appropriately combined.

[Additional Descriptions]

A part or all of the above-described embodiments can be described as, but are not limited to, the following additional descriptions in addition to the claims:

(Additional Description 1)

A biological information measurement apparatus comprising a hardware processor and a memory, the apparatus being configured to:

transmit a radio wave toward a measurement site of a user;

receive a reflected wave of the radio wave reflected by the measurement site and output a waveform signal of the reflected wave;

execute, by the hardware processor, a program stored in the memory, thereby extracting information indicative of a feature of a waveform from the waveform signal; and determine whether a setting position of the biological information measurement apparatus with respect to the measurement site satisfies a condition corresponding to a preset reference position based on the extracted information indicative of the feature of the waveform.

(Additional Description 2)

A biological information measurement apparatus comprising a hardware processor and a memory, the apparatus being configured toe transmit a radio wave toward a measurement site of a user;

receive a reflected wave of the radio wave reflected by the measurement site and output a waveform signal of the reflected wave;

execute, by the hardware processor, a program stored in the memory, thereby extracting information indicative of a feature of a waveform from the waveform signal; and compare information indicative of a feature of a first waveform extracted by the feature extraction unit in a transmission operation of the radio wave and a reception operation of the reflected wave at a first time with information indicative of a feature of a second waveform extracted by the feature extraction unit in a transmission operation of the radio wave and a reception operation of the reflected wave at a second time, and to determine a correction direction of a setting position of the biological information measurement apparatus with respect to the measurement site based on the comparison result.

(Additional Description 3)

A biological information measurement apparatus comprising a hardware processor and a memory, the apparatus being configured to:

transmit radio waves toward a measurement site of a user through first and second antennas dispersedly arranged on a surface opposable to the measurement site, receive reflected waves of the radio waves reflected by the measurement site, and output waveform signals of the reflected waves;

execute, by the hardware processor, a program stored in the memory, thereby extracting information indicative of features of the waveforms from the waveform signals; and to compare information indicative of a feature of a first waveform extracted by the feature extraction unit in a transmission operation of the radio wave and a reception operation of the reflected wave through the first antenna with information indicative of a feature of a second waveform extracted by the feature extraction unit in a transmission operation of the radio wave and a reception operation of the reflected wave through the second antenna, and determine a correction direction of a setting position of the biological information measurement apparatus with respect to the measurement site based on the comparison result.

(Additional Description 4)

A biological information measurement method executed by an apparatus including a hardware processor and a memory storing a program that causes the hardware processor to execute, the method comprising:
- transmitting a radio wave toward a measurement site of a user;
- receiving a reflected wave of the radio wave reflected by the measurement site and outputting a waveform signal of the reflected wave;
- extracting, by the hardware processor, information indicative of a feature of a waveform from the waveform signal; and
- determining, by the hardware processor, whether a setting position of the biological information measurement apparatus with respect to the measurement site satisfies a condition corresponding to a preset reference position based on the extracted information indicative of the feature of the waveform.

(Additional Description 5)

A biological information measurement method executed by an apparatus including a hardware processor and a memory storing a program that causes the hardware processor to execute, the method comprising:
- transmitting a radio wave toward a measurement site of a user;
- receiving a reflected wave of the radio wave reflected by the measurement site and outputting a waveform signal of the reflected wave;
- extracting, by the hardware processor, information indicative of a feature of a waveform from the waveform signal; and
- comparing, by the hardware processor, information indicative of a feature of a first waveform extracted by the extracting in a transmission operation of the radio wave and a reception operation of the reflected wave at a first time with information indicative of a feature of a second waveform extracted by the extracting in a transmission operation of the radio wave and a reception operation of the reflected wave at a second time, and determining a correction direction of a setting position of the biological information measurement apparatus with respect to the measurement site based on the comparison result.

(Additional Description 6)

A biological information measurement method executed by an apparatus including a hardware processor and a memory storing a program that causes the hardware processor to execute, the method comprising:
- transmitting radio waves toward a measurement site of a user through first and second antennas dispersedly arranged on a surface opposable to the measurement site, receiving reflected waves of the radio waves reflected by the measurement site, and outputting waveform signals of the reflected waves;
- extracting, by the hardware processor, information indicative of features of waveforms from the waveform signals; and
- comparing, by the hardware processor, information indicative of a feature of a first waveform extracted by the extracting in a transmission operation of the radio wave and a reception operation of the reflected wave through the first antenna with information indicative of a feature of a second waveform extracted by the extracting in a transmission operation of the radio wave and a reception operation of the reflected wave through the second antenna, and determining a correction direction of a setting position of the biological information measurement apparatus with respect to the measurement site based on the comparison result.

(Additional Description 7)

A biological information measurement apparatus (1) for measuring biological information of a user, the apparatus comprising:
- a transmitter (3) configured to transmit a radio wave toward a measurement site of the user;
- a receiver (4) configured to receive a reflected wave of the radio wave reflected by the measurement site and output a waveform signal of the reflected wave;
- a feature extraction unit (121) configured to extract information indicative of a feature of a waveform from the waveform signal;
- a first determination unit (122) configured to determine whether a setting position of the biological information measurement apparatus with respect to the measurement site satisfies a condition corresponding to a preset reference position based on the extracted information indicative of the feature of the waveform; and
- an output unit (5) configured to output information indicative of a determination result through the first determination unit.

REFERENCE SIGNS LIST

1 . . . biological information measurement apparatus, wearable device, blood pressure monitor
2 . . . sensor unit
3 . . . transmitter
4 . . . receiver
5 . . . output unit
10 . . . main body
12 . . . processing unit
14 . . . storage unit
16 . . . input/output interface
17 . . . communication interface
20 . . . strap
30 . . . server
40 . . . transmission/reception unit
50 . . . display
52 . . . controller
90 . . . wrist
91 . . . radial artery
101 . . . pulse detector
111 . . . antenna control unit
121 . . . feature extraction unit
122 . . . determination unit
123 . . . moving direction estimation unit
141 . . . reference value storage unit
153 . . . display
10B . . . port e terminal
900 . . . network

The invention claimed is:

1. A biological information measurement apparatus for measuring biological information of a user, the apparatus comprising:
- a transmitter configured to transmit a radio wave toward a measurement site of the user, the measurement site being a radial artery of a human wrist;

a receiver configured to receive a reflected wave of the radio wave reflected by the measurement site and output a waveform signal of the reflected wave; and a control unit comprising a processor configured to perform operations comprising:

extracting information indicative of a feature of a waveform from the waveform signal;

determining whether a setting position of the biological information measurement apparatus with respect to the measurement site satisfies a condition corresponding to a preset reference position based on the extracted information indicative of the feature of the waveform to provide a determination result; and outputting information indicative of the determination result, wherein:

the processor of the control unit is configured to perform operations further comprising controlling a series of operations comprising operations by the transmitter and the receiver, the operation of extracting the information indicative of the feature of the waveform, and the operation of determining whether the setting position of the biological information measurement apparatus with respect to the measurement site satisfies the condition, the transmitter and the receiver are included in a pulse sensor measuring pulse waves in the radial artery of the human wrist and include a first antenna and a second antenna dispersedly arranged on a surface facing a surface of the measurement site, and transmit radio waves and receive reflected waves through the first and second antennas; and the processor of the control unit is configured to perform operations further comprising selecting the first antenna and causing the series of operations to be performed at a first time, and in response to determining that the setting position of the biological information measurement apparatus fails to satisfy the condition through the series of operations at the first time, selecting the second antenna and causing the series of operations to be performed at a second time.

2. The biological information measurement apparatus according to claim 1, wherein the processor of the control unit is configured to perform operations such that:

extracting information indicative of a feature of a waveform from the waveform signal comprises extracting information on an amplitude of the waveform signal as the feature of the waveform of the waveform signal; and determining whether the setting position of the biological information measurement apparatus with respect to the measurement site satisfies the condition corresponding to the preset reference position based on the extracted information indicative of the feature of the waveform comprises determining whether the amplitude of the waveform signal is within a preset first amplitude range corresponding to the reference position based on the extracted information on the amplitude of the waveform signal.

3. The biological information measurement apparatus according to claim 1, wherein the processor of the control unit is configured to perform operations such that:

extracting information indicative of a feature of a waveform from the waveform signal comprises extracting information on a shape of a waveform for each repetition section of the waveform signal as the feature of the waveform of the waveform signal, and determining whether the setting position of the biological information measurement apparatus with respect to the measurement site satisfies the condition corresponding to the preset reference position based on the extracted information indicative of the feature of the waveform comprises calculating a correlation value between the extracted shape of the waveform and a shape of a preset reference waveform corresponding to the reference position based on the extracted information on the shape of the waveform, and determines whether the correlation value is within a preset first correlation value range.

4. The biological information measurement apparatus according to claim 1, wherein the series of operations further comprises the operation of outputting information indicative of the determination result, the processor of the control unit is configured to perform operations such that causing the series of operations to be performed comprises, if it is determined that the setting position of the biological information measurement apparatus fails to satisfy the condition through the series of operations at the first time, causing the series of operations to be performed at a second time.

5. The biological information measurement apparatus according to claim 4, wherein if it is determined that the setting position of the biological information measurement apparatus fails to satisfy the condition through the series of operations at the first time, the processor of the control unit is configured to perform operations comprising causing the series of operations to be performed at the second time in response to any one of an elapse of a predetermined time after the determination, an input of a measurement instruction by the user, and a change in the setting position of the biological information measurement apparatus by a predetermined amount or more.

6. The biological information measurement apparatus according to claim 1, wherein:

the transmitter and the receiver include a first transmission antenna and first and second reception antennas dispersedly arranged on a surface opposable to the measurement site, and transmit radio waves and receive reflected waves through the first transmission antenna and the first and second reception antennas; and the processor of the control unit is configured to perform operations further comprising selecting the first transmission antenna and the first reception antenna and causing the series of operations to be performed at a first time, and in response to determining that the setting position of the biological information measurement apparatus fails to satisfy the condition through the series of operations at the first time, selecting the first transmission antenna and the second reception antenna and causing the series of operations to be performed at a second time.

7. A biological information measurement apparatus for measuring biological information of a user, the apparatus comprising:

a transmitter configured to transmit a radio wave toward a measurement site of the user, the measurement site being a radial artery of a human wrist;

a receiver configured to receive a reflected wave of the radio wave reflected by the measurement site and output a waveform signal of the reflected wave;

the transmitter and the receiver which are included in a pulse sensor measuring pulse waves in the radial artery of the human wrist include a first antenna and a second antenna dispersedly arranged on a surface facing a surface of the measurement site, and transmit the radio wave and receive the reflected wave through the first and second antennas;
a control unit comprising a processor configured to perform operations comprising:
extracting information indicative of a feature of a waveform from the waveform signal;
comparing information indicative of an extracted feature of a first waveform in a transmission operation of the radio wave and a reception operation of the reflected wave at a first time with information indicative of an extracted feature of a second waveform in a transmission operation of the radio wave and a reception operation of the reflected wave at a second time, and determine a correction direction of a setting position of the biological information measurement apparatus with respect to the measurement site based on the comparison result; and
an output unit configured to output information indicative of the determined correction direction.

8. The biological information measurement apparatus according to claim 7, wherein the processor of the control unit is configured to perform operations such that:
comparing the information indicative of the extracted feature of the first waveform in the transmission operation of the radio wave and the reception operation of the reflected wave at the first time with the information indicative of the extracted feature of the second waveform in the transmission operation of the radio wave and the reception operation of the reflected wave at the second time, comprises calculating a correction amount of the setting position of the biological information measurement apparatus with respect to the measurement site based on the comparison result; and
outputting information indicative of the determined correction direction comprises outputting the calculated correction amount.

9. A biological information measurement apparatus for measuring biological information of a user, the apparatus comprising:
a transceiver including first and second antennas dispersedly arranged on a surface opposable to a measurement site of the user which is a radial artery of a human wrist, configured to transmit radio waves toward the measurement site and receive reflected waves of the radio waves reflected by the measurement site through the first and second antennas, and output waveform signals of the reflected waves, the transceiver being included in a pulse sensor measuring pulse waves in the radial artery of the human wrist;
a control unit comprising a processor configured to perform operations comprising:
extracting information indicative of features of waveforms from the waveform signals;
comparing information indicative of an extracted feature of a first waveform in a transmission operation of the radio wave and a reception operation of the reflected wave through the first antenna with information indicative of an extracted feature of a second waveform in a transmission operation of the radio wave and a reception operation of the reflected wave through the second antenna, and determine a correction direction of a setting position of the biological information measurement apparatus with respect to the measurement site based on the comparison result; and
outputting information indicative of the determined correction direction.

10. A biological information measurement apparatus for measuring biological information of a user, the apparatus comprising:
a transceiver including a first transmission antenna and first and second reception antennas dispersedly arranged on a surface opposable to a measurement site of the user which is a radial artery of a human wrist, configured to transmit radio waves toward the measurement site and receive reflected waves of the radio waves reflected by the measurement site through the first transmission antennas and the first and second reception antennas, and output waveform signals of the reflected waves, the transceiver being included in a pulse sensor measuring pulse waves in the radial artery of the human wrist;
a control unit comprising a processor configured to perform operations comprising:
extracting information indicative of features of waveforms from the waveform signals;
comparing information indicative of an extracted feature of a first waveform in a transmission operation of the radio wave through the first transmission antenna and a reception operation of the reflected wave through the first reception antenna with information indicative of an extracted feature of a second waveform in a transmission operation of the radio wave through the first transmission antenna and a reception operation of the reflected wave through the second reception antenna, and determine a correction direction of a setting position of the biological information measurement apparatus with respect to the measurement site based on a comparison result; and
outputting information indicative of the determined correction direction.

11. The biological information measurement apparatus according to claim 9, wherein the processor of the control unit is configured to perform operations such that:
comparing the information indicative of the feature of the first waveform with the information indicative of the feature of the second waveform comprises calculating a correction amount of the setting position of the biological information measurement apparatus with respect to the measurement site based on the comparison result; and
outputting information indicative of the determined correction direction comprises outputting the calculated correction amount.

12. The biological information measurement apparatus according to claim 8, wherein the processor of the control unit is configured to perform operations such that calculating the correction amount of the setting position comprises calculating the correction amount by linear approximation based on the information indicative of the feature of the first waveform and the information indicative of the feature of the second waveform.

13. The biological information measurement apparatus according to claim 8, wherein the processor of the control unit is configured to perform operations such that calculating the correction amount of the setting position comprises calculating the correction amount by nonlinear approximation based on the information indicative of the feature of the first waveform and the information indicative of the feature of the second waveform.

14. The biological information measurement apparatus according to claim 9, wherein the processor of the control unit is configured to perform operations such that outputting information indicative of the determined correction direction comprises outputting a user notification of the information indicative of the determination result through the first determination unit or the correction direction determined by the second determination unit by at least one of text, an image, sound, vibration, and lighting or blinking of light.

15. A biological information measurement method executed by a biological information measurement apparatus for measuring biological information of a user, the method comprising:

transmitting a radio wave toward a measurement site of the user to measure pulse waves in a radial artery of a human wrist, the measurement site being the radial artery of the human wrist;

receiving a reflected wave of the radio wave reflected by the measurement site and outputting a waveform signal of the reflected wave to measure pulse waves in the radial artery of the human wrist;

extracting information indicative of a feature of a waveform from the waveform signal;

determining whether a setting position of the biological information measurement apparatus with respect to the measurement site satisfies a condition corresponding to a preset reference position based on the extracted information indicative of the feature of the waveform;

outputting information indicative of a determination result determined by the determining; and controlling a series of operations of the transmitting, the receiving, the extracting, and the determining, wherein:

the transmitting and the receiving include transmitting radio waves and receiving reflected waves through a first antenna and a second antenna dispersedly arranged on a surface facing a surface of the measurement site, and the controlling includes selecting the first antenna and causing the series of operations to be performed at a first time, and in response to determining that the setting position of the biological information measurement apparatus fails to satisfy the condition through the series of operations at the first time, selecting the second antenna and causing the series of operations to be performed at a second time.

16. A biological information measurement method executed by a biological information measurement apparatus for measuring biological information of a user, the method comprising:

transmitting a radio wave toward a measurement site of the user to measure pulse waves in a radial artery of a human wrist, the measurement site being the radial artery of the human wrist;

receiving a reflected wave of the radio wave reflected by the measurement site and outputting a waveform signal of the reflected wave to measure pulse waves in the radial artery of the human wrist;

the transmitting and receiving comprise transmitting and receiving through a first antenna and a second antenna dispersedly arranged on a surface facing a surface of the measurement site;

extracting information indicative of a feature of a waveform from the waveform signal;

comparing information indicative of a feature of a first waveform extracted by the extracting in a transmission operation of the radio wave and a reception operation of the reflected wave at a first time with information indicative of a feature of a second waveform extracted by the extracting in a transmission operation of the radio wave and a reception operation of the reflected wave at a second time, and determining a correction direction of a setting position of the biological information measurement apparatus with respect to the measurement site based on the comparison result; and outputting information indicative of the determined correction direction.

17. A biological information measurement method executed by a biological information measurement apparatus for measuring biological information of a user, the method comprising:

transmitting radio waves toward a measurement site of the user through first and second antennas dispersedly arranged on a surface opposable to the measurement site, receiving reflected waves of the radio waves reflected by the measurement site, and outputting waveform signals of the reflected waves, the transmitting and the receiving are performed to measure pulse waves in a radial artery of a human wrist, the measurement site being the radial artery of the human wrist;

extracting information indicative of features of waveforms from the waveform signals;

comparing information indicative of a feature of a first waveform extracted by the extracting in a transmission operation of the radio wave and a reception operation of the reflected wave through the first antenna, and information indicative of a feature of a second waveform extracted by the extracting in a transmission operation of the radio wave and a reception operation of the reflected wave through the second antenna, and determining a correction direction of a setting position of the biological information measurement apparatus with respect to the measurement site based on the comparison result; and outputting information indicative of the determined correction direction.

18. A biological information measurement method executed by a biological information measurement apparatus for measuring biological information of a user, the method comprising:

transmitting radio waves toward a measurement site of the user through a first transmission antenna and first and second reception antennas dispersedly arranged on a surface opposable to the measurement site, receiving reflected waves of the radio waves reflected by the measurement site; and outputting waveform signals of the reflected waves, the transmitting and the receiving are performed to measure pulse waves in a radial artery of a human wrist, the measurement site being the radial artery of the human wrist;

extracting information indicative of features of waveforms from the waveform signals;

comparing information indicative of a feature of a first waveform extracted by the extracting in a transmission operation of the radio wave through the first transmission antenna and a reception operation of the reflected wave through the first reception antenna, and information indicative of a feature of a second waveform extracted by the extracting in a transmission operation of the radio wave through the first transmission antenna and a reception operation of the reflected wave through the second reception antenna, and determining a correction direction of a setting position of the biological information measurement apparatus with respect to the measurement site based on the comparison result; and outputting information indicative of the determined correction direction.

19. A non-transitory computer readable medium storing a computer program for causing a computer to perform operations comprising:

transmitting a radio wave toward a measurement site of the user to measure pulse waves in a radial artery of a human wrist, the measurement site being a radial artery of the human wrist;

receiving a reflected wave of the radio wave reflected by the measurement site and outputting a waveform signal of the reflected wave to measure pulse waves in the radial artery of the human wrist;

extracting information indicative of a feature of a waveform from the waveform signal;

determining whether a setting position of the biological information measurement apparatus with respect to the measurement site satisfies a condition corresponding to a preset reference position based on the extracted information indicative of the feature of the waveform;

outputting information indicative of a determination result determined by the determining; and controlling a series of operations of the transmitting, the receiving, the extracting, and the determining, wherein:

the transmitting and the receiving include transmitting radio waves and receiving reflected waves through a first antenna and a second antenna dispersedly arranged on a surface facing a surface of the measurement site, and the controlling includes selecting the first antenna and causing the series of operations to be performed at a first time, and in response to determining that the setting position of the biological information measurement apparatus fails to satisfy the condition through the series of operations at the first time, selecting the second antenna and causing the series of operations to be performed at a second time.

* * * * *